United States Patent
Too et al.

(10) Patent No.: US 10,100,331 B2
(45) Date of Patent: Oct. 16, 2018

(54) REAGENT FOR GENE-DRUG THERAPEUTICS

(71) Applicants: Agency for Science, Technology and Research, Singapore (SG); National University of Singapore, Singapore (SG)

(72) Inventors: Heng-Phon Too, Singapore (SG); Yoon Khei Ho, Singapore (SG); Lihan Zhou, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/439,330

(22) PCT Filed: Oct. 29, 2013

(86) PCT No.: PCT/SG2013/000464
§ 371 (c)(1),
(2) Date: Apr. 29, 2015

(87) PCT Pub. No.: WO2014/070111
PCT Pub. Date: May 8, 2014

(65) Prior Publication Data
US 2015/0361449 A1    Dec. 17, 2015

Related U.S. Application Data

(60) Provisional application No. 61/719,908, filed on Oct. 29, 2012.

(51) Int. Cl.
| | | |
|---|---|---|
| C12N 15/87 | (2006.01) | |
| C12N 15/85 | (2006.01) | |
| C12N 5/00 | (2006.01) | |
| A61K 31/7084 | (2006.01) | |
| A61K 48/00 | (2006.01) | |
| A61K 31/711 | (2006.01) | |
| A61K 47/34 | (2017.01) | |
| A61K 9/127 | (2006.01) | |
| A61K 39/00 | (2006.01) | |

(52) U.S. Cl.
CPC ............ *C12N 15/85* (2013.01); *A61K 9/1272* (2013.01); *A61K 31/711* (2013.01); *A61K 39/0011* (2013.01); *A61K 47/34* (2013.01); *A61K 48/00* (2013.01); *C12N 15/87* (2013.01); *A61K 2039/5152* (2013.01); *A61K 2039/5156* (2013.01); *A61K 2039/55522* (2013.01)

(58) Field of Classification Search
None
See application file for complete search history.

(56) References Cited

U.S. PATENT DOCUMENTS

| | | | | |
|---|---|---|---|---|
| 8,486,990 | B2* | 7/2013 | Napper | A61K 31/403 514/411 |
| 2005/0075268 | A1* | 4/2005 | Berg | A61K 39/0011 514/1 |
| 2010/0022637 | A1* | 1/2010 | Stockwell | C07D 307/68 514/459 |
| 2012/0046346 | A1* | 2/2012 | Rossi | C12N 15/111 514/44 R |
| 2012/0225115 | A1* | 9/2012 | Au | A61K 31/704 424/450 |

FOREIGN PATENT DOCUMENTS

| | | |
|---|---|---|
| JP | 2003535832 A | 12/2003 |
| JP | 2007289162 A | 11/2007 |
| JP | 2008504827 A | 2/2008 |
| KR | 20120047346 A1 | 5/2012 |
| WO | WO-01/93836 A2 | 12/2001 |
| WO | WO-2006/007712 A1 | 1/2006 |
| WO | WO 2006007712 * | 1/2006 |
| WO | WO-2008/103431 A2 | 8/2008 |
| WO | WO-2011/097181 A2 | 8/2011 |
| WO | WO-2013/052053 A1 | 4/2013 |
| WO | WO-2013/155572 A1 | 10/2013 |
| WO | WO-2014/070111 A1 | 5/2014 |

OTHER PUBLICATIONS

Roche, PC-12 Customer Transfectin Protocol, 2012, pp. 1-2, https://shop.roche.com/wcsstore/RASCatalogAssetStore/Articles/CustomerProtocol_X-tremeGENE%209_PC-12.pdf.*
Brewer, G. J., et al., "Optimized Survival of Hippocampal Neurons in B27-Supplemented Neurobasal™, a New Serum-free Medium Combination", *Journal of Neuroscience Research*, 35(5), (1993), 567-576.
Lorenz, Matthew A., et al., "Reducing Time and Increasing Sensitivity in Sample Preparation for Adherent Mammalian Cell Metabolomics", *Anal Chem.*, 83(9), (2011), 3406-3414.
Mishra, Swaroop, et al., "PEGylation significantly affects cellular uptake and intracellular trafficking of non-viral gene delivery particles", *European Journal of Cell Biology*, 83(3), (2004), 97-111.
Ozpolat, B., et al., "Nanomedicine based approaches for the delivery of siRNA in cancer", *Journal of Internal Medicine*, 267, (2010), 44-53.
Wightman, Lionel, et al., "Different behavior of branched and linear polyethylenimine for gene delivery in vitro and in vivo", *J Gene Med.*, 3(4), (Jul. 2001), 362-372.

(Continued)

*Primary Examiner* — Maria Marvich
(74) *Attorney, Agent, or Firm* — Schwegman Lundberg & Woessner, P.A.

(57) ABSTRACT

The present invention relates to a composition for transfecting a cell with a genetic material comprising a first agent capable of directing the genetic material away from the acidic compartments in the cell and a second agent capable of stabilizing the microtubule or a network thereof. The invention also relates to the use of the composition in the manufacture of a medicament for treating a disease, a method for delivering a genetic material into a cell and a kit.

18 Claims, 58 Drawing Sheets

Specification includes a Sequence Listing.

(56) References Cited

OTHER PUBLICATIONS

Yoong, Li F., et al., "GDNF-induced cell signaling and neurite outgrowths are differentially mediated by GFRalpha1 isoforms", Mol Cell Neurosci., 41(4), (2009), 464-473.

Zhang, Yang, et al., "DC-Chol/DOPE cationic liposomes: A comparative study of the influence factors on plasmid pDNA and siRNA gene delivery", *International Journal of Pharmaceutics*, 390(2), (2010), 198-207.

Zhou, Lihan, et al., "Mitochondrial Localized STAT3 Is Involved in NGF Induced Neurite Outgrowth", *PLoS One 6*(6): e21680, (2011), 13 pgs.

Zong-Wei, Wu, et al., "Recent progress in copolymer-mediated siRNA delivery", *Journal of Drug Targeting*, 20(7), (Aug. 2012), 551-560.

Hasegawa, S., et al., "Microtubule Involvement in the Intracellular Dynamics for Gene Transfection Mediated by Cationic Liposomes", Gene Therapy (2001) 8, 1669-1673, (Aug. 24, 2001), 1669-1673.

Wong, Ho Lun, et al., "Paclitaxel Tumor-Priming Enhances siRNA Delivery and Transfection in 3-Dimensional Tumor Cultures", Mol. Pharmaceutics 2011, 8, 833-849, (Mar. 21, 2011), 833-849.

Xu, Zhenghong, et al., "The characteristics and performance of a multifunctional nanoassembly system for the co-delivery of docetaxel and iSur-pDNA in a mouse hepatocellular carcinoma model", Biomaterials 31 (2010) 916-922, (Oct. 20, 2009), 916-922.

\* cited by examiner

Combinatorial drug-gene therapeutics a.
Native

RA b.
% of cells with intracellular pDNA

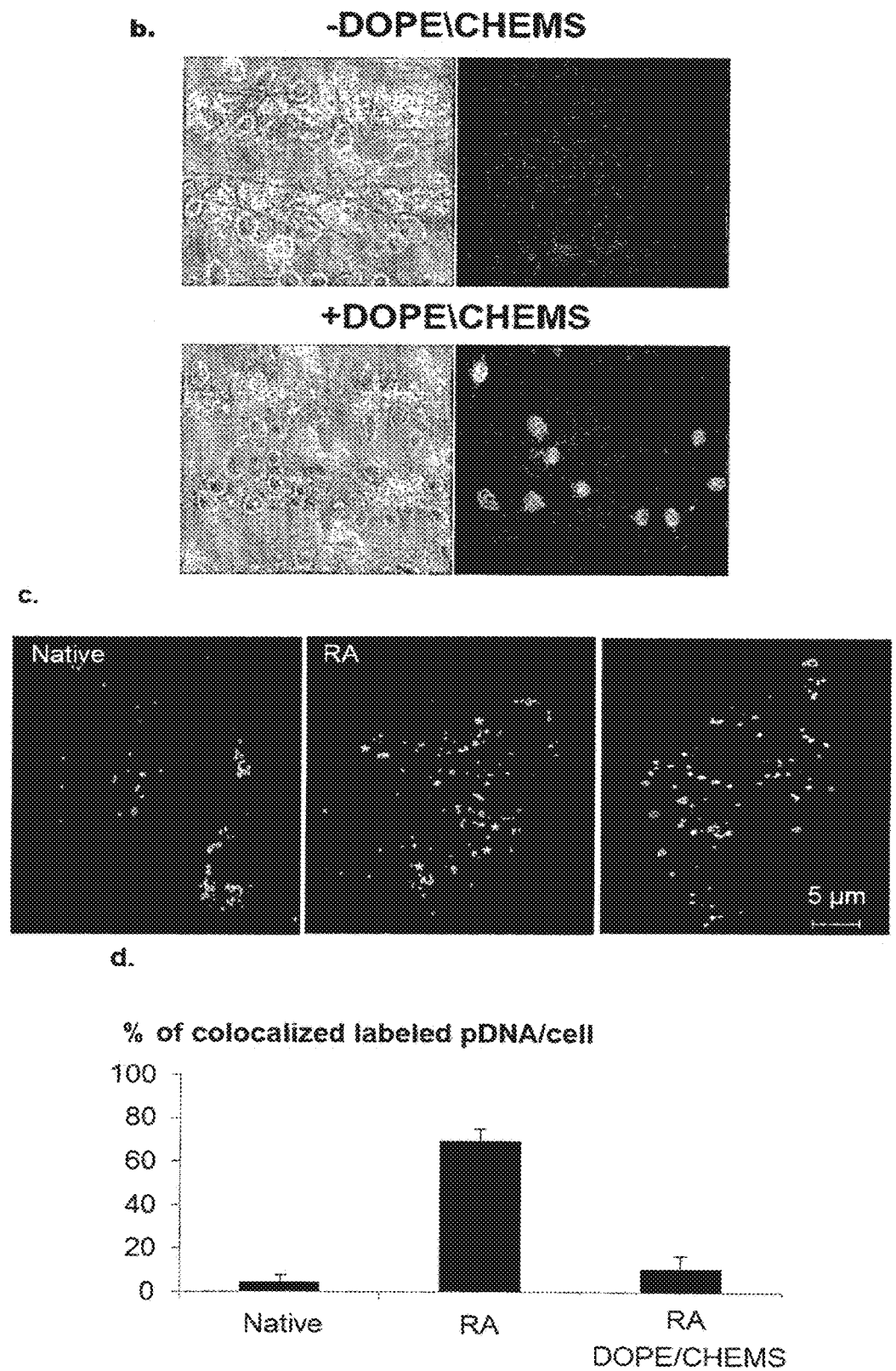

a.

b.

a.
Native

FSK a.

b.

b. Glycolysis/Glucogenesis c. Glycogen metabolism d. Nucleotide metabolism e. Phospholipid Biosynthesis f. Tryptophan metabolism

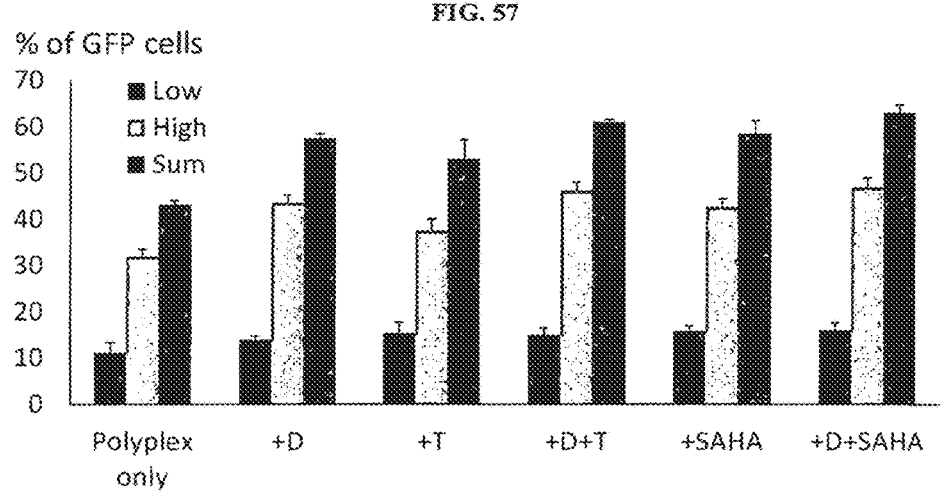
FIG. 57
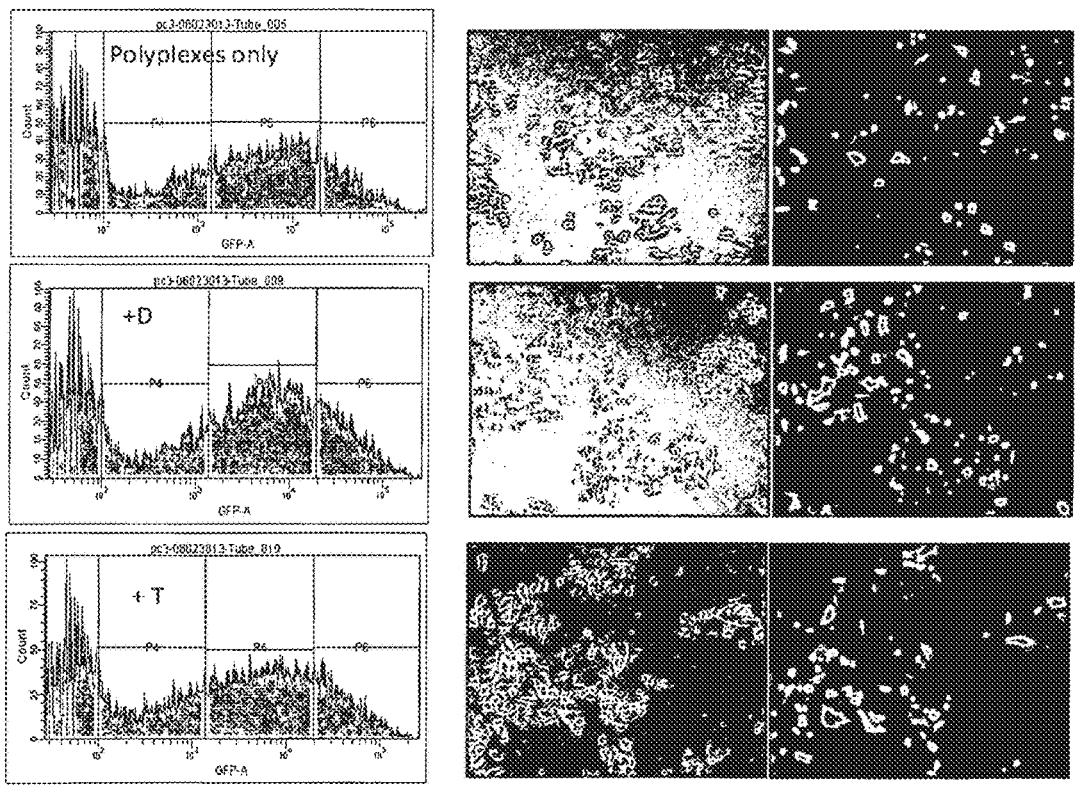

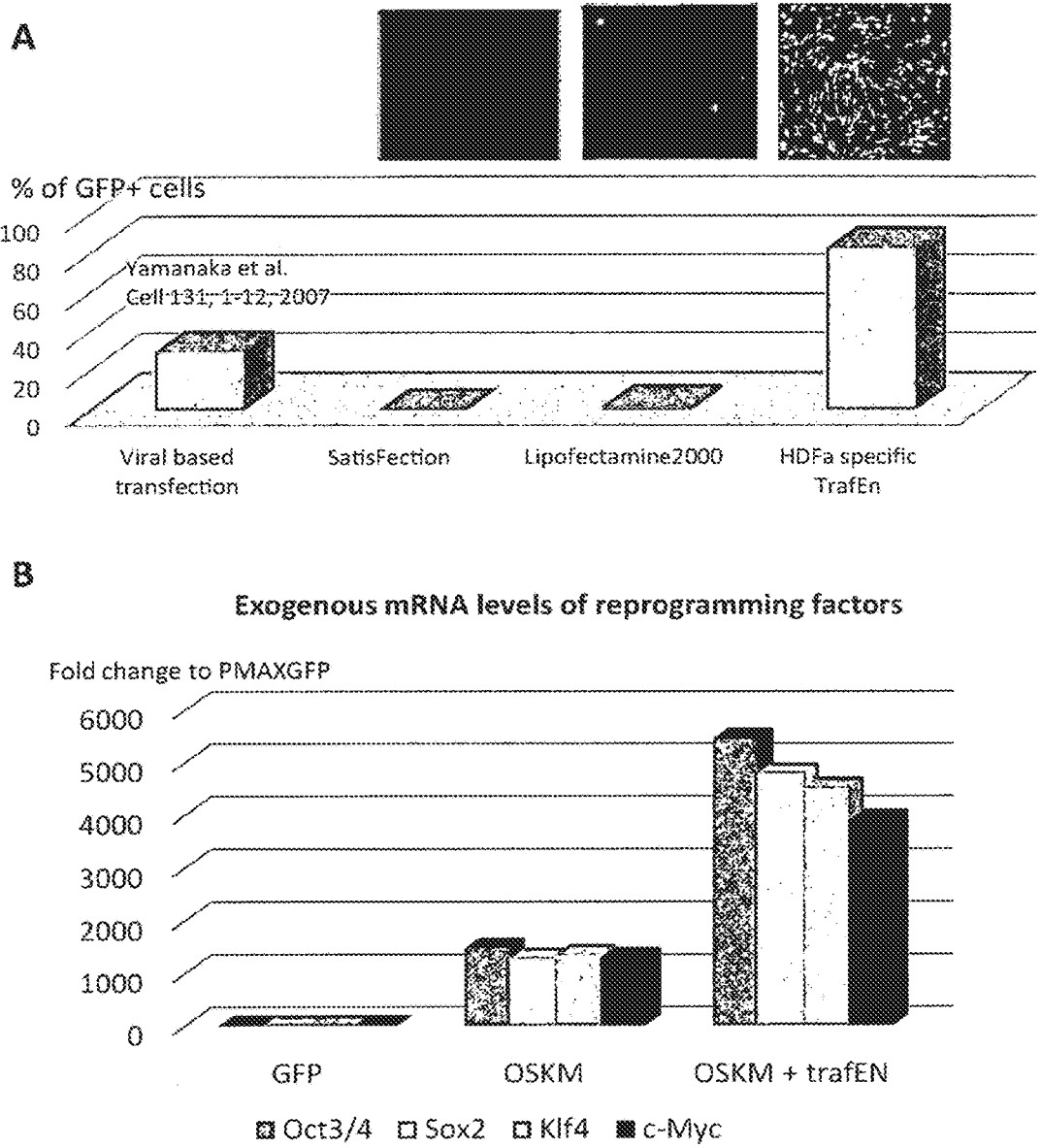

Fold change of Klf4 to control

REAGENT FOR GENE-DRUG THERAPEUTICS

CROSS-REFERENCE TO RELATED APPLICATIONS

This application is a U.S. national stage application filed under 35 U.S.C. § 371 from International Application Serial No. PCT/SG2013/000464, which was filed 29 Oct. 2013, and published as WO 2014/070111 on 08 May 2014, and which claims the benefit of priority of US provisional application No. 61/719,908 filed Oct. 29, 2012, which applications and publication are incorporated by reference as if reproduced herein and made a part hereof in their entirety, and the benefit of priority of each of which is claimed herein.

FIELD OF THE INVENTION

The present disclosure relates to composition for transfecting a cell with a genetic material. In particular, the invention relates to transfecting a cell using comprising a first agent capable of directing the genetic material away from the acidic compartments in the cell and a second agent capable of stabilizing the microtubule or a network thereof.

BACKGROUND OF THE INVENTION

Gene delivery of pDNA, antisense oligonucleotides and shRNA offers the potential for the treatment of devastating disorders including neurodegenerative diseases and spinal cord injuries, for which there are currently few treatment options. However, nucleic acid-based therapeutics is still in the early stages of development as a new category of biologics. The efficacy of gene delivery requires delivery of these molecules to the interior of the cell, presenting significant challenges for delivery strategies. Given the disadvantages associated with clinical application of viral carriers, as existing non-viral carriers transfect differentiated neurons poorly, non-viral gene delivery serves as an attractive alternative due to reduced immunogenicity, the ability to accommodate large size of transgenes, improved safety, and ease of manufacturing.

Polyethylenimine (LPEI), an off-the-shelf transfection agent, has been used to transfect a variety of cell types, including neurons in vivo and in vitro. It is thought that LPEI condenses DNA into nanoparticles, along with the cationic property of LPEI, facilitates entry of these vectors into cells by binding to negatively charged heparan sulfate proteoglycans on the cell surface. Following internalization, LPEI/DNA nanocomplexes are thought to be transported to the perinuclear region of cells. LPEI is then hypothesized to escape endosomes through a "proton-sponge effect", releasing the DNA from the polymer and the DNA subsequently taken up into the nucleus.

Recent efforts to increase transfection efficiency and cell viability of differentiated neuron by optimizing protocols using LPEI have met with limited success. Attempts have been made to identify underlying mechanisms limiting high transfection efficiency in non-neuronal cells, primary neurons and neuronal cell-lines. Poor transfection of non-dividing, post-mitotic cells including neuronal cells is often thought to be due to the presumed inability of the pDNA in nuclear translocation. In addition, internalization and intracellular barriers were thought to restrict transfection in differentiated neuronal cell. By increasing uptake, more neuronal cells were found to express transgene, but only marginally (from 2% to 6% of total cell population). To date, the goal of attaining high transfection efficiency in differentiated neuron using non-viral carriers remains elusive and efforts to produce even more novel polymers with such properties continues.

Despite significant improvements in diagnosis and innovations in the treatment for various devastating diseases, such as cancer, autoimmune disease, and neurodegenerative disease, effective treatment of these disorders still presents major challenges. Presently, low transfection and delivery efficiencies limit the application of drug-gene therapeutics. It is this unmet need that requires the development of methods to enhance gene delivery ex vivo and in vivo and the subsequent development of galenics using this technology.

Accordingly, it is an aim of the present disclosure to ameliorate the above-mentioned disadvantages and provide an improving transfection efficiency.

SUMMARY OF THE INVENTION

In a first aspect, the present invention provides a composition for transfecting a cell with a genetic material comprising a first agent capable of directing the genetic material away from an acidic compartment in the cell and a second agent capable of stabilizing the microtubule or a network thereof.

In a second aspect, the present invention provides a method of delivering a genetic material into a cell comprising the step of administering the genetic material with a composition.

In a third aspect, the present invention provide a use of a composition in the manufacture of a medicament for treating a disease, selected from a group consisting of cancer, SMA, bone cancers, leukemia, blood cancers, sickle cell disease, Wiskott-Aldrich Syndrome, HIV, genetic disease, diabetes, cardiac disease and neurodegenerative diseases In a fourth aspect, there is provided a composition comprising a first agent, as described herein, and a second agent, as described herein.

In a fifth aspect, the present invention provides a kit according comprising a composition as described herein and instructions for use.

BRIEF DESCRIPTION OF THE DRAWINGS

The invention will be better understood with reference to the detailed description when considered in conjunction with the non-limiting examples and the accompanying drawings, in which.

TBA, such as chemotherapeutic taxanes, binds to tubulin while inhibition of HDAC6 and Sirtuin2 prevents deacetylations of microtubules; leading to microtubule stabilization. (B) depicts the possible effects of histone deacetylation inhibitors (HDACi). These appear to ease the pathological conditions of heart failure via possible multiple mechanisms, including derepression of protective genes and inhibition of the expression of pro-inflammatory genes. Other non-transcriptional effects of HDACi may include the enhancement of acetylation of sacromeric proteins and the inhibition of pathways for autophagy and apoptosis.

Figure 2:
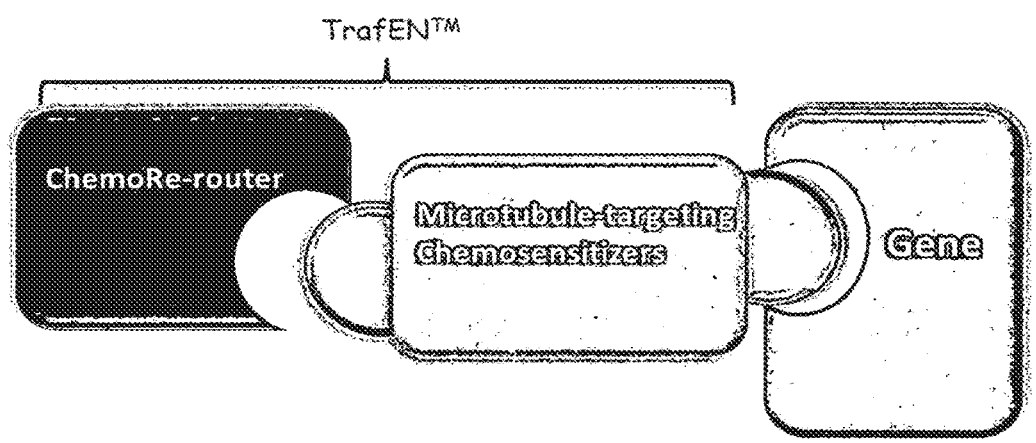
FIG. 2 shows a schematic of the composition of TrafEn™, which contains an optimized mix of chemoRe-router and microtubule targeting chemosensitizer. TrafEn™ is shown to enhance transfection efficiency and synergize\ with the gene product to achieve beneficial therapeutic effects.
Figure 4:
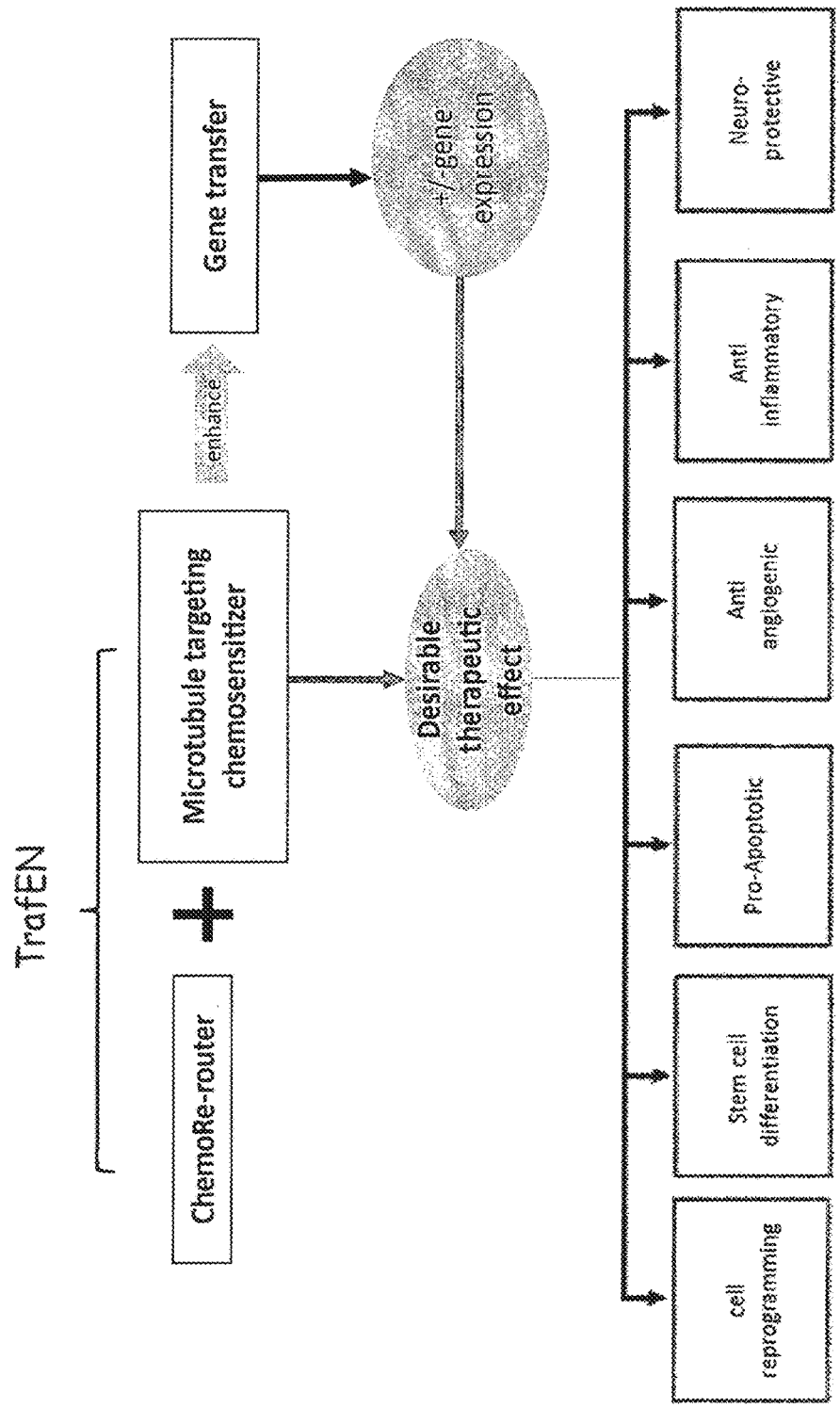

FIG. 4 shows a schematic depicting the synergistic effect of TrafEn™ and its use as a novel gene-drug therapy combinatorial therapeutic. As described previously in FIG. 2, the components that make up TrafEn™ are a microtubule targeting chemosensitizer and a chemoRe-router. Both these components interact to aid and enhance a gene transfer process, which could result in an up- or down-regulation of gene expression of a targeted gene. This regulation of gene expression, together with the chemosensitizer, may result in a desired therapeutic effect, which could be, but is not limited to, cell reprogramming, stem cell differentiation, pro-apoptotic effect, anti-angiogenic effect, anti-inflammatory effect and/or a neuroprotective effect.

Figure 5:
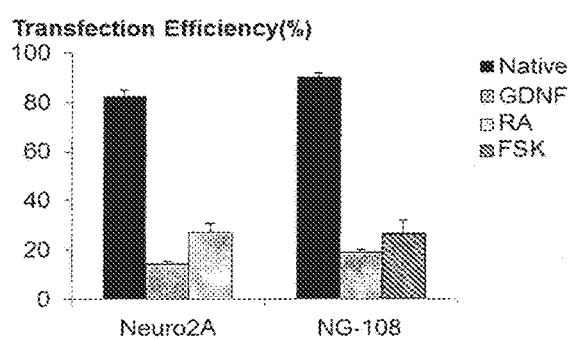
Figure 5:
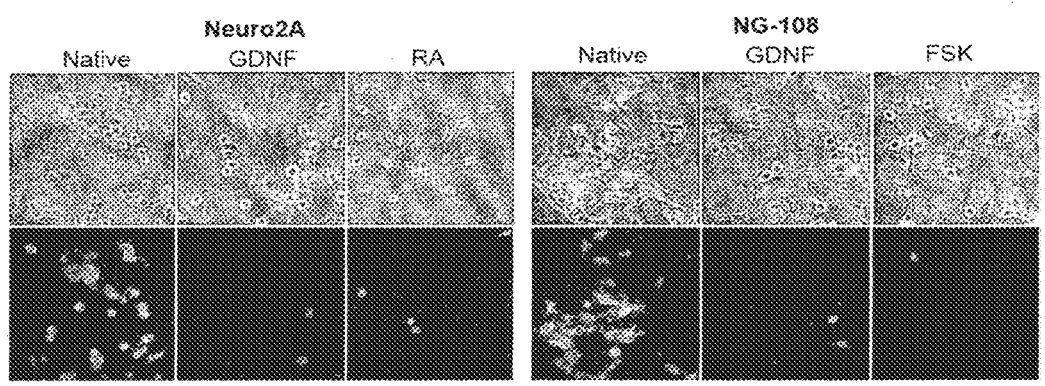
Figure 5:
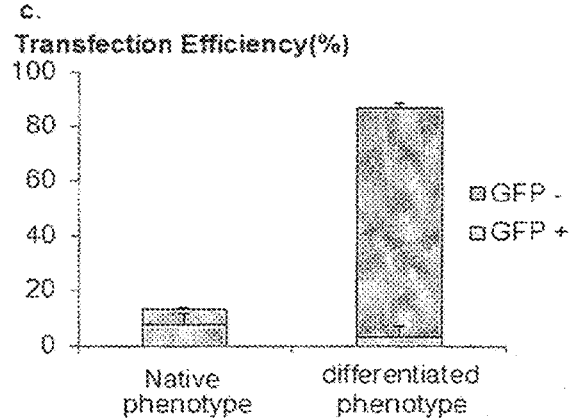

FIG. 5 shows data that aggregated polyplex transfected native, but not differentiated neuronal cells efficiently. A. Cells were differentiated by 50 ng/ml of GDNF, 10 μM of all trans Retinoic acid (RA), or 10 μM Forskolin (FSK) for 48 h prior to transfection. Native and differentiated cells were transfected with polyplex (N/P=20) using mild centrifugation. Percentage of cells expressing green fluorescence protein (EGFP) was quantified by FACS 48 h post transfection. B. Representative fluorescent images (bottom rows), acquired 48 h post transfection. C. Percentages of EGFP positive (+) and negative (−) Neuro2A cells (native and differentiated phenotypes) treated with 10 μM RA were determined by counting fluorescent and bright field images. Cells bearing neurites twice the cell body length were considered as differentiated phenotype. The data shown were the mean±s.e.m., n=4.

Figure 6:
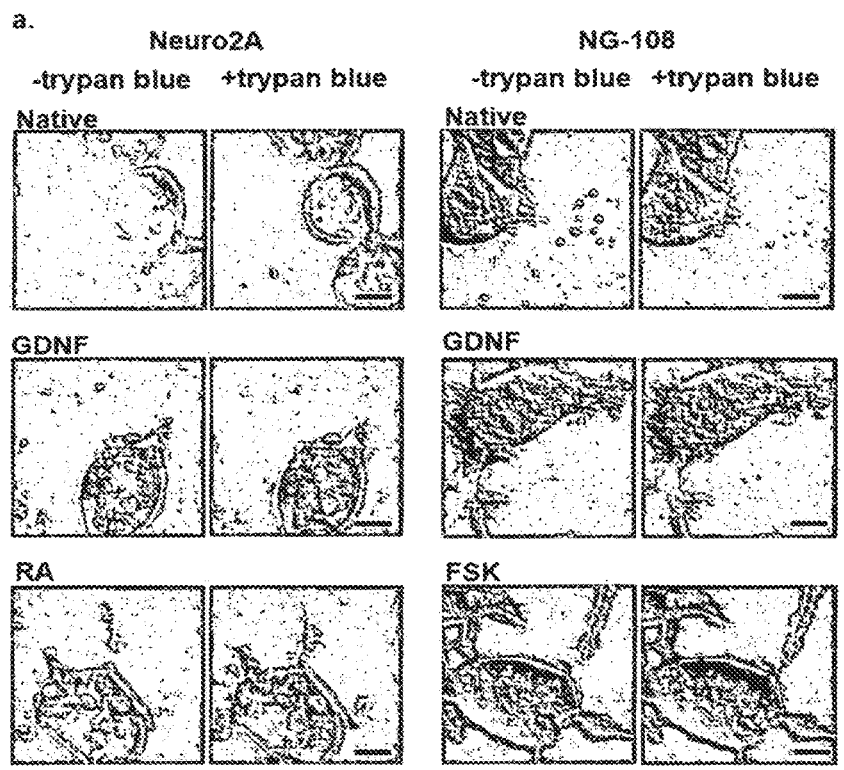
Figure 6:
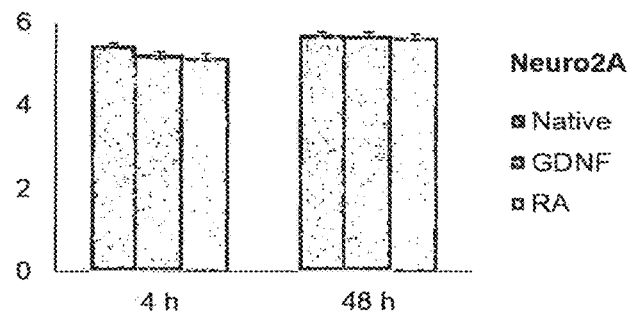
Figure 6:
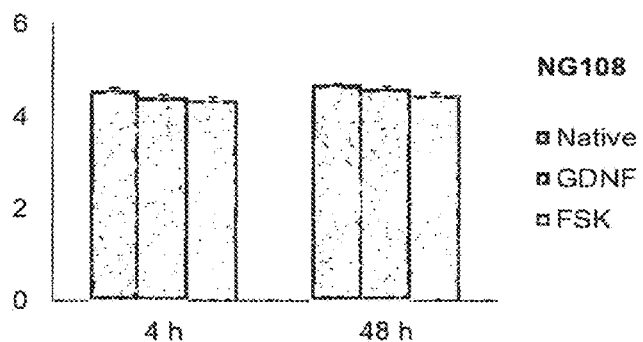

FIG. 6 shows micrographs and histograms showing that the internalization of polyplex was unaffected after differentiation. A. Native and differentiated Neuro2A and NG-108 cells were transfected with Rhodamine-pDNA polyplex (N/P=20) using mild centrifugation procedure. After 4 h incubation, cells images were taken before and after quenching with 0.4% trypan blue. Bar represents 10 μm. B. At various time points post transfection by polyplex (N/P=20), cells were treated with pAA/DNAse to remove extracellular pDNA. Cells were trypsinized and treated with pAA/urea lysis buffer before quantification of internalized DNA by qPCR. The data shown were the mean±s.e.m., n=3.

Figure 7:
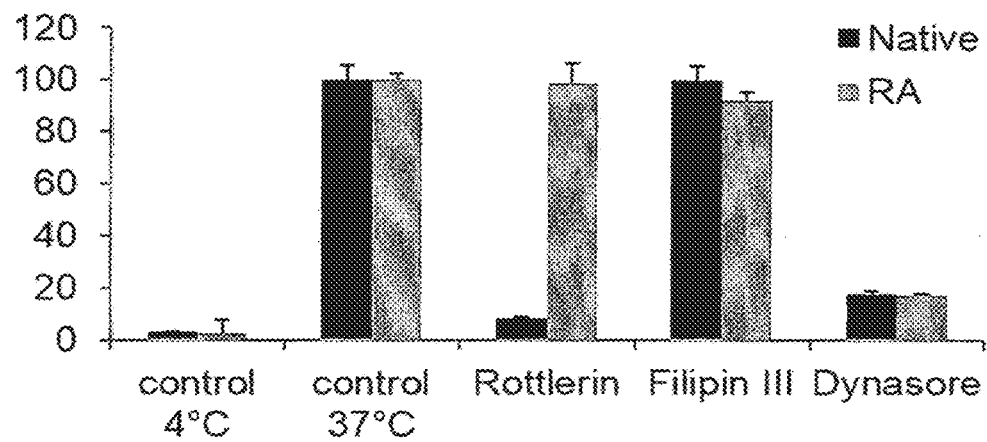
Figure 7:
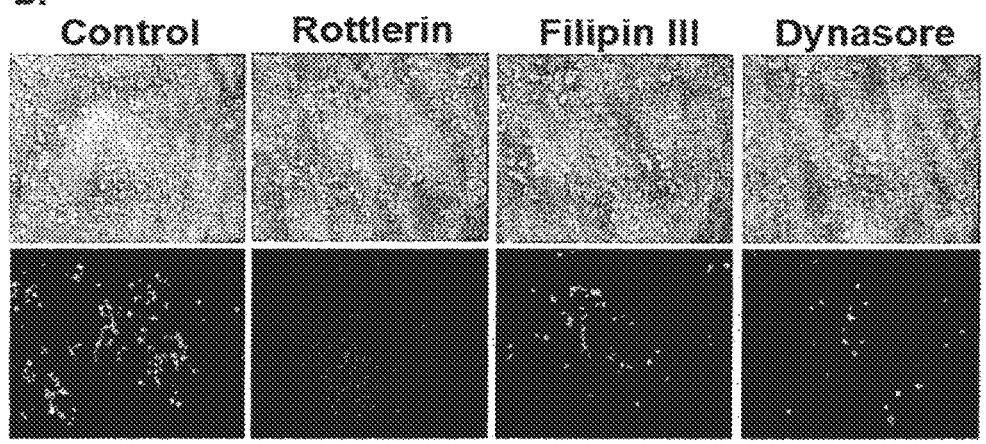
Figure 7:
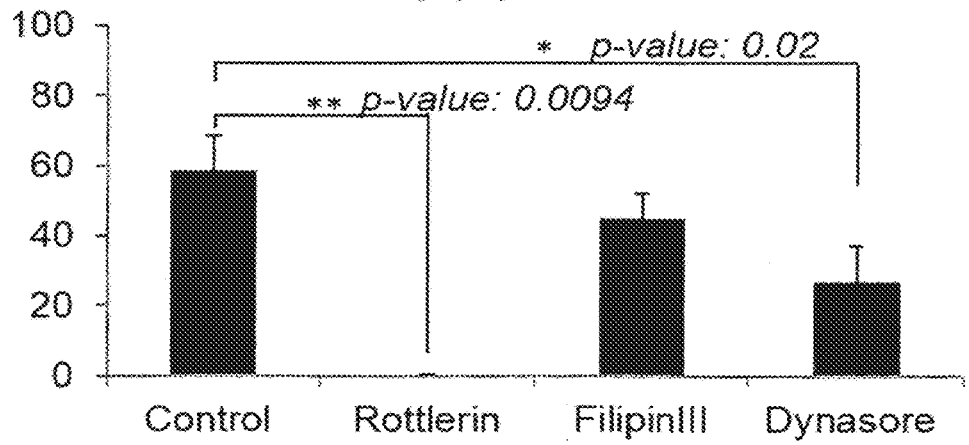

FIG. 7 shows data showing that PKC was involved in the uptake of polyplex in native but not differentiated neuronal cells. A. Native and differentiated (10 μM RA) Neuro2a was treated with 2.5 μg/ml rottlerin, 5 μg/ml Filipin III or 30 μg/ml Dynasore for 45 min prior transfection. DMSO/0.5% FBS was used as control for treatment. After transfection with polyplex (N/P=20), cells were incubated at 4° C. or 37° C. for 4 h. Extracellular pDNA was removed by pAA/DNAse and cells were trypsinized. Then, samples were treated with pAA/urea lysis buffer and the absolute copy number of pDNA was quantified by qPCR. In similar experiments, native Neuro2A cells were incubated at 37° C. for 24 h post transfection. B. Representative fluorescent images (bottom rows), acquired 48 h post transfection. C. Percentage of cells expressing EGFP was counted. Significant differences in transfection efficiencies were calculated using the two tailed student's t-test. The data shown were the mean±s.e.m., n=4. *, $p<0.05$; **, $p<0.005$.

Figure 8:
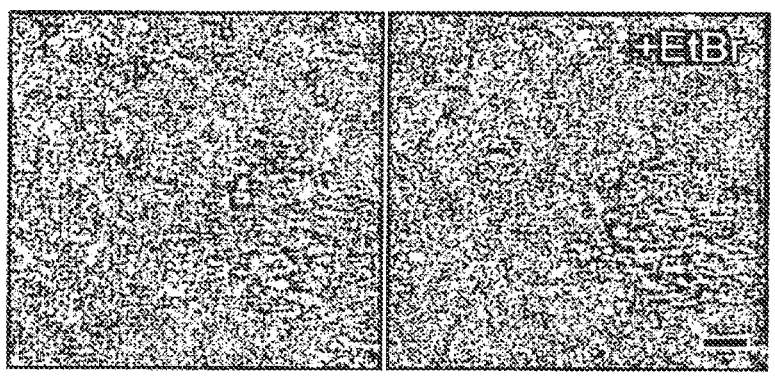
Figure 8:
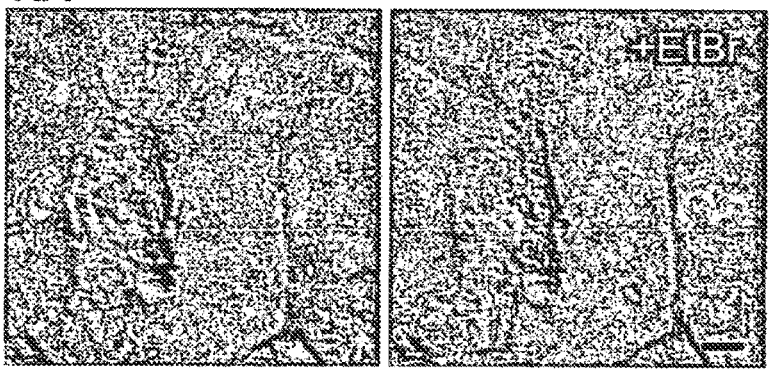
Figure 8:
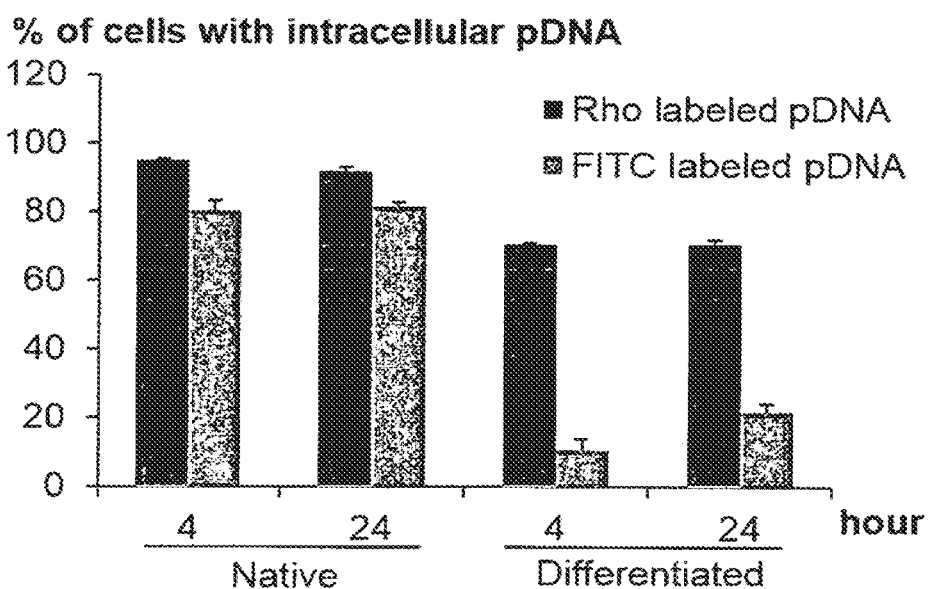
Figure 8:
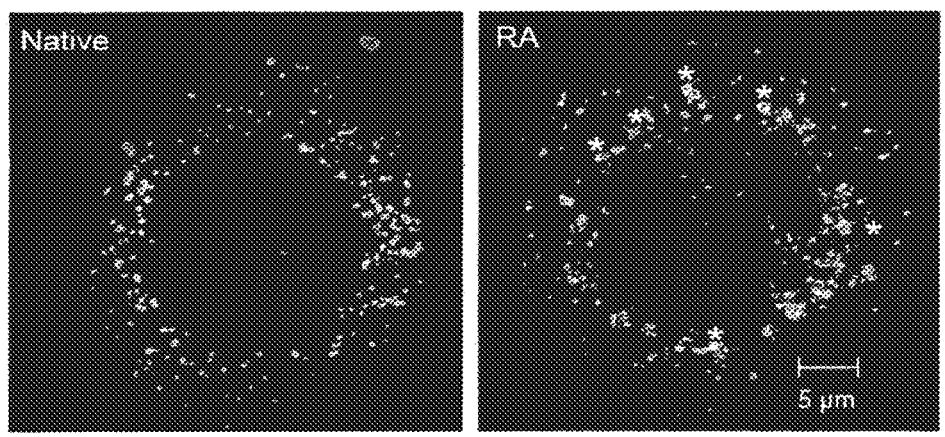
Figure 8:
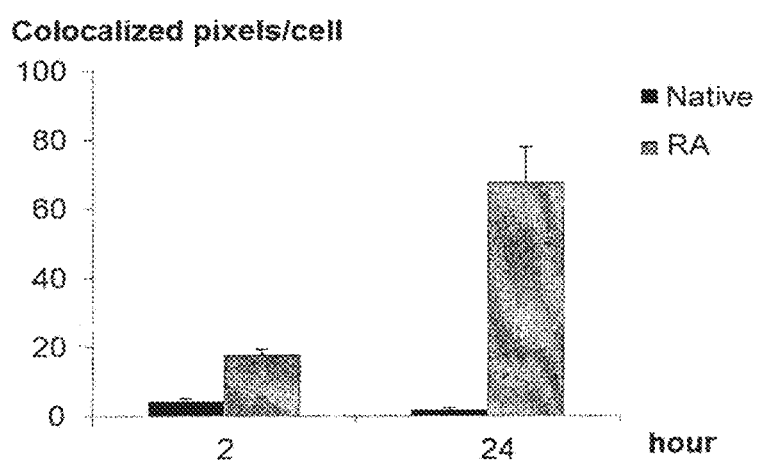

FIG. 8 shows micrograph images and column graphs, showing that polyplex localized differentially in native and differentiated neuronal cells. A. Native and differentiated (10 μM RA) Neuro2A cells were transfected using LPEI/FITC-pDNA (N/P=20) with centrifugation transfection procedure. Quenching reagent EtBr (20 μg/ml) was added 4 h post transfection. Cell images were taken before and after quenching by EtBr. Bar represents 5 μm. B. Cells were transfected by pre-complexed LPEI/FITC- or Rhodamine-pDNA at N/P=20. Percentage of cells associated with labeled pDNA was acquired after quenching of extracellular fluorescence with EtBr or trypan blue, at 4 or 24 h post transfection. Ratios of FITC/Rhodamine (FITC/Rho) in native and differentiated Neuro2A cells were calculated. C. Four hour after transfection of native and differentiated Neuro2A with LPEI/Rhodamine-pDNA (N/P=20), culture media was removed and replenished with 1×PBS containing 50 nM Lysotracker green DND-26 and the incubation continued for 5 min before visualization using confocal microscopy. Images of single cell were captured at 100× magnification. Asterisks indicated co-localization of polyplex with the labelled compartments. D. Co-localized pixels of Rhodamine with lysotracker green DND-26 was analysed. The data shown were the mean±s.e.m (n=20).

Figure 9:
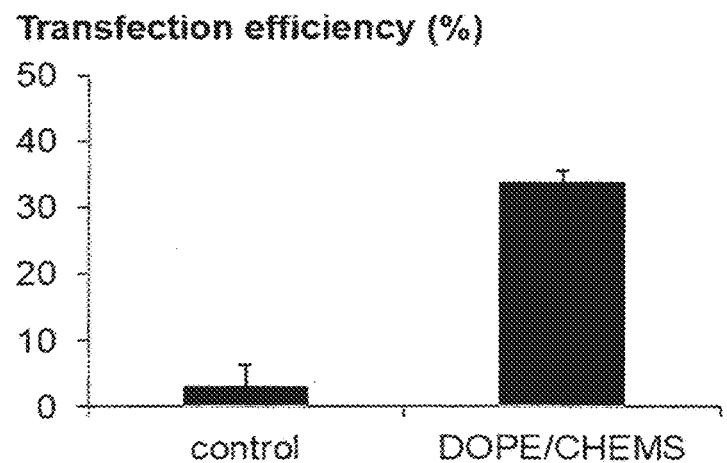

FIG. 9 visualises data showing that endosomal escape of polyplex, facilitated by DOPE/CHEMS, greatly enhanced transfection. A. Neuro2A cells differentiated with RA were transfected by LPEI/pDNA at N/P=20 with centrifugation transfection procedure. Pre-complexed DOPE/CHEMS (9:2 molar ratio) in HEPES was added to the culture medium immediately post transfection. Transfection efficiency was analysed by counting fluorescent and bright field images 24 h later. Percentage of EGFP positive cells bearing neurites twice the cell body length was presented as group mean±s.e.m (n=4). B. Representative images captured at the end of incubation were presented. C. Native and differentiated Neuro2A cells were transfected by LPEI/Rhodamine-pDNA (N/P=20). Then, acidic compartment was labelled with lysotracker green at 4 h post transfection. Images of single cell were captured at 100× magnification and D. the co-localized pixels were analysed. Data were presented as group mean±s.e.m (n=20).

Figure 10:
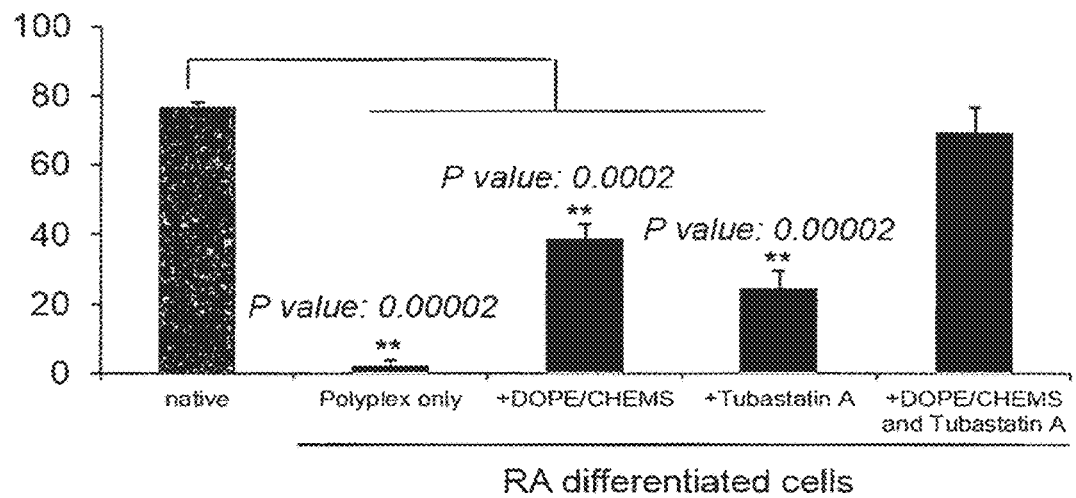
Figure 10:
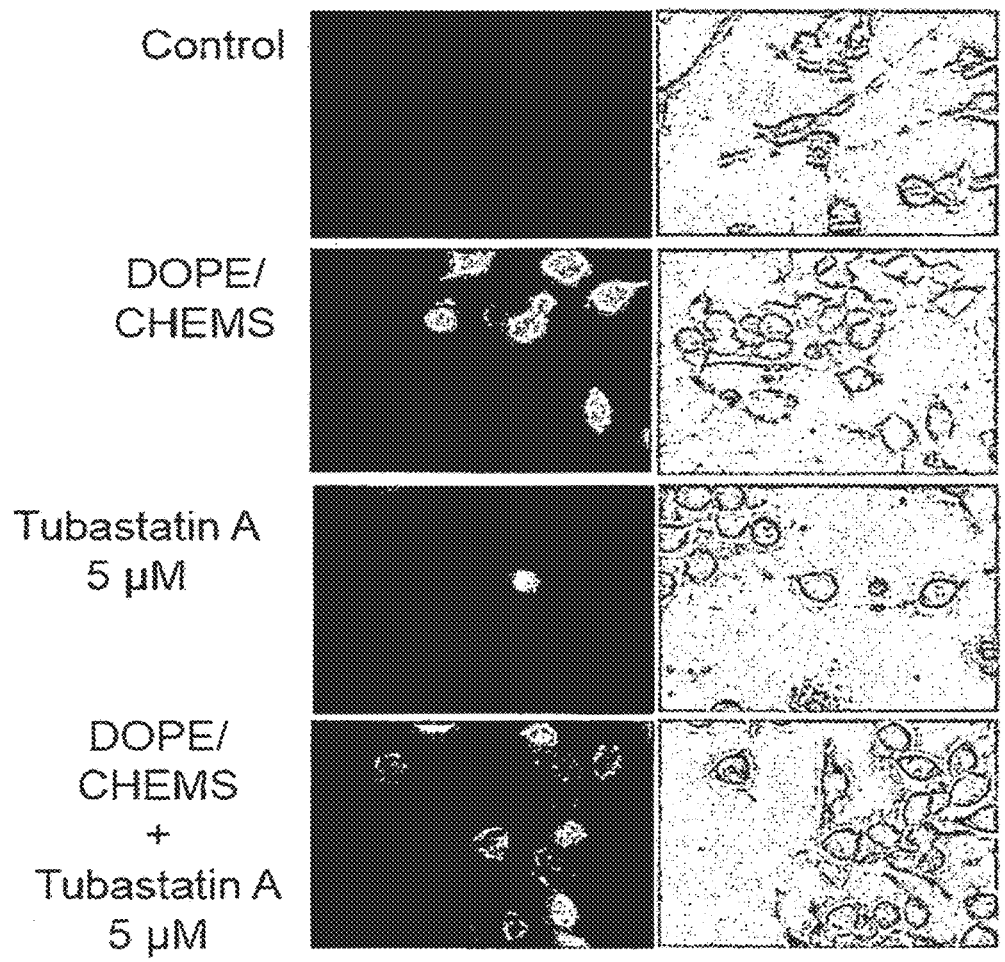
Figure 10:
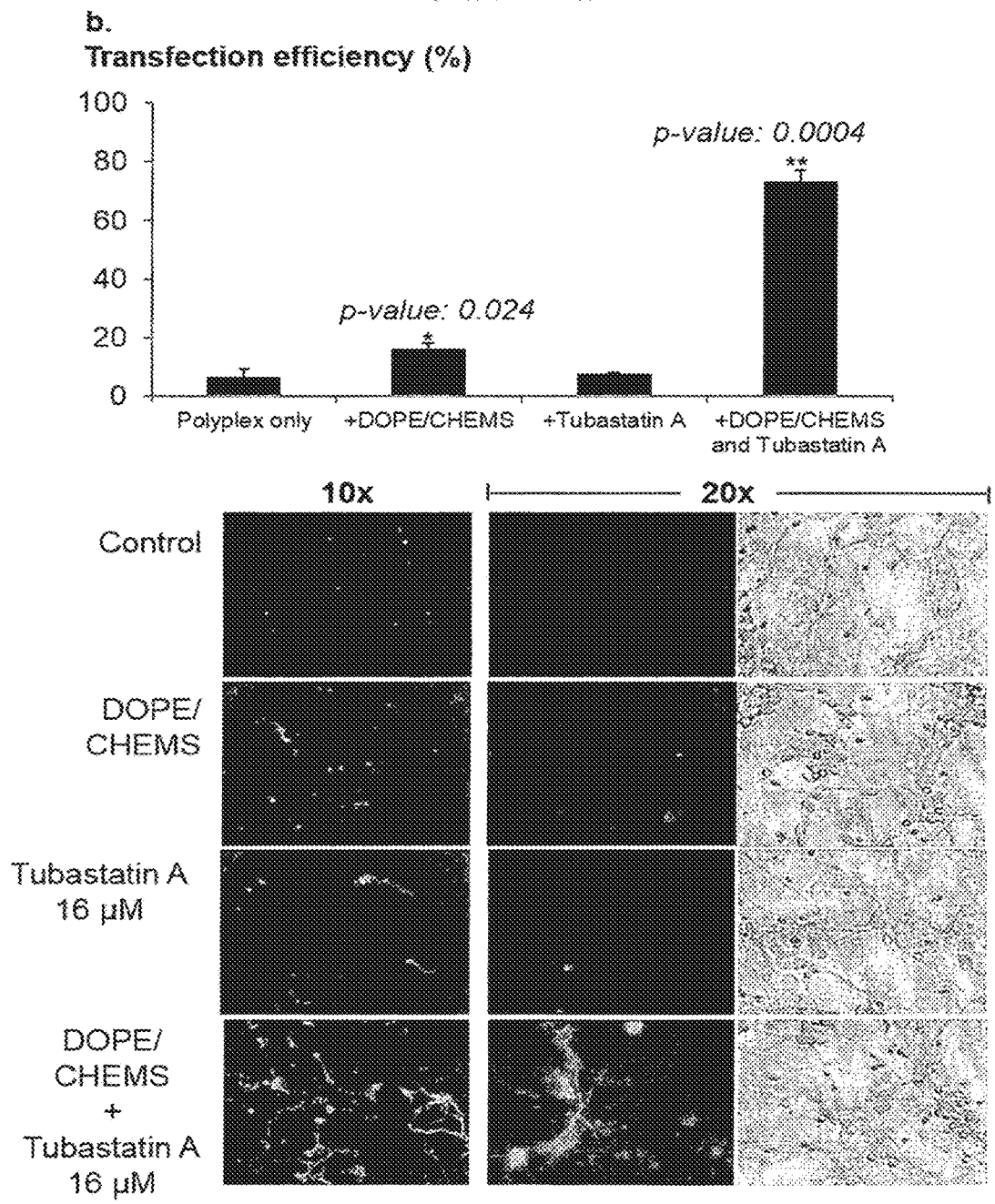

FIG. 10 shows histograms and micrographs, showing data that enhanced trafficking following endosomal escape of polyplex greatly improved transfection. Native and differentiated (10 μM RA) Neuro2A cells or primary cortical neurons (DIV 3) were transfected with LPEI/pDNA (N/P=20) using centrifugation transfection procedure. A. For differentiated Neuro2A, in the presence/absence of DOPE/CHEMS, Tubastatin A (5 μM) was added 1 h post transfection and further incubated for 24 h. For native Neuro2A (black bar), the whole cell population was counted. For differentiated Neuro2A (grey bar), cells bearing neurites twice the cell body length were counted. Data presented as mean±s.e.m (n=4). Representative images (20× magnification) of transfected differentiated cells (left panel). B. Primary cortical neurons were initially exposed to the polyplex and subsequently with neurobasal media containing the various combinations of DOPE/CHEMS and Tubastatin A (16 μM). The treatment was terminated 24 h later and the cells were incubated for a further 48 h in fresh neurobasal media. Transfection efficiency was quantified by FACS and represented as mean±s.d (n=3). Representative images (20× magnification) were shown. Significant differences in transfection efficiencies were calculated using the two tailed student's t-test. *, p<0.05; **, p<0.005.

Figure 11:
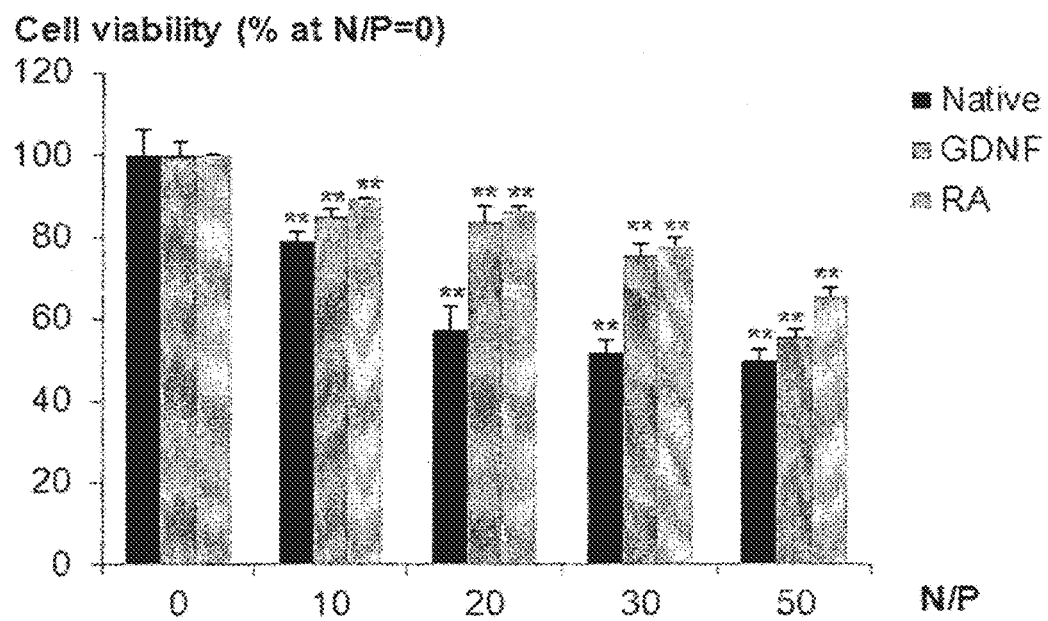
Figure 11:
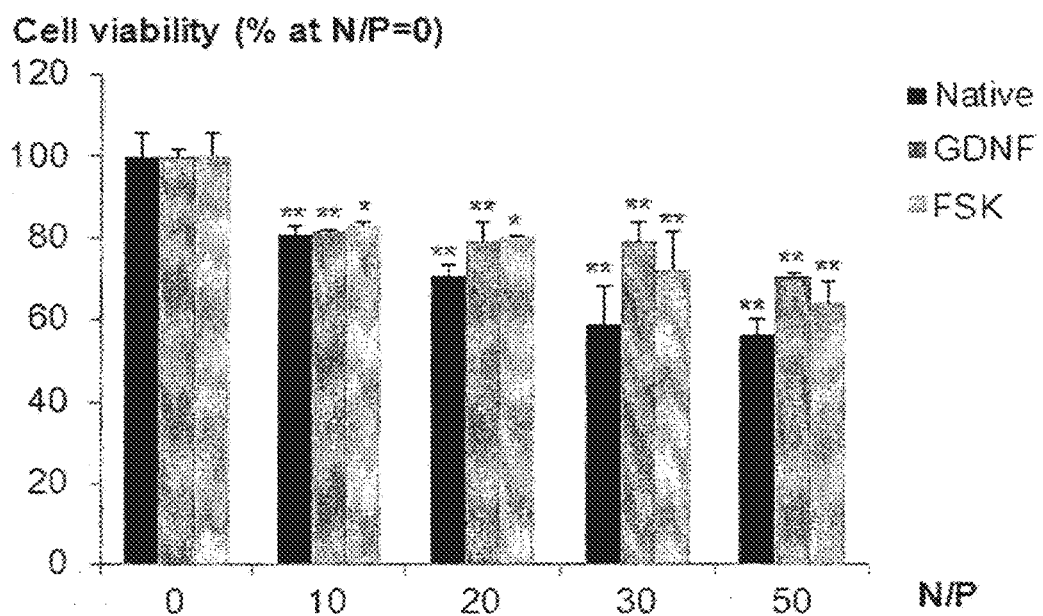

FIG. 11 shows histograms visualising that increasing N/P ratios reduced cell viability. Native and differentiated A. Neuro2A and B. NG-108 cells were transfected with pIRES-EGFP-EV71 complexed with LPEI at various N/P ratios. In a bolus transfection, the cells were exposed to transfection mixture for 4 h. Cell viability was measured by MTS assay after 48 h incubation in fresh media. Data points were expressed as a percentage of control (N/P=0) and group mean±s.e.m. (n=6). Significant differences in cell viabilities against control (N/P=0) were calculated using the two tailed student's t-test. *, p<0.05; **, p<0.005.

Figure 12:
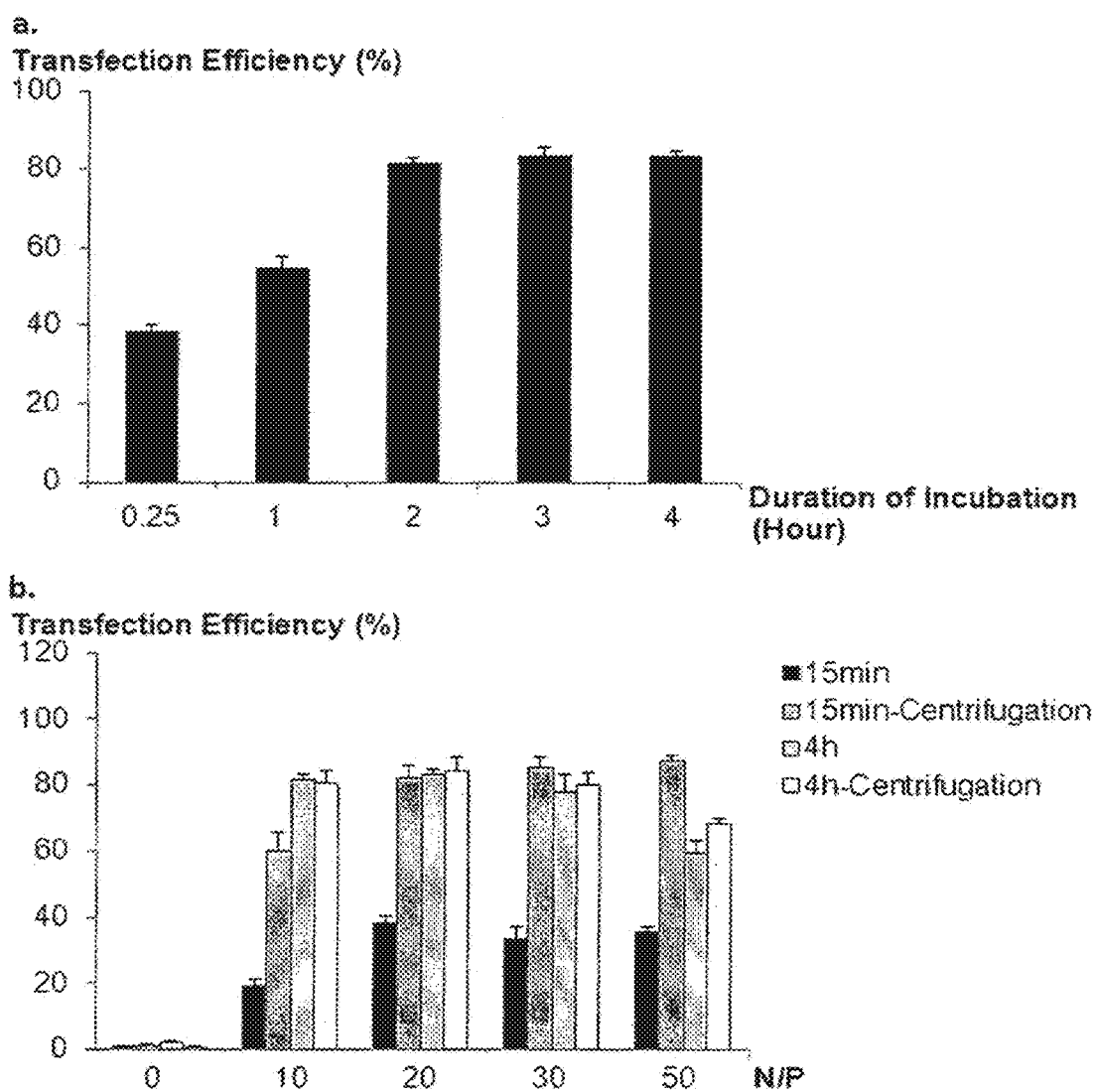

FIG. 12 shows histograms depicting that mild centrifugation improved transfection efficiency. Neuro2A cells were transfected with LPEI/pDNA using A. N/P=20 and B. various N/P ratios over different periods of time, with or without centrifugation at the end of incubation. Percentage of EGFP positive cells was quantified by FACS 48 h post transfection. The data shown are the mean±s.e.m., n=4.

Figure 13:
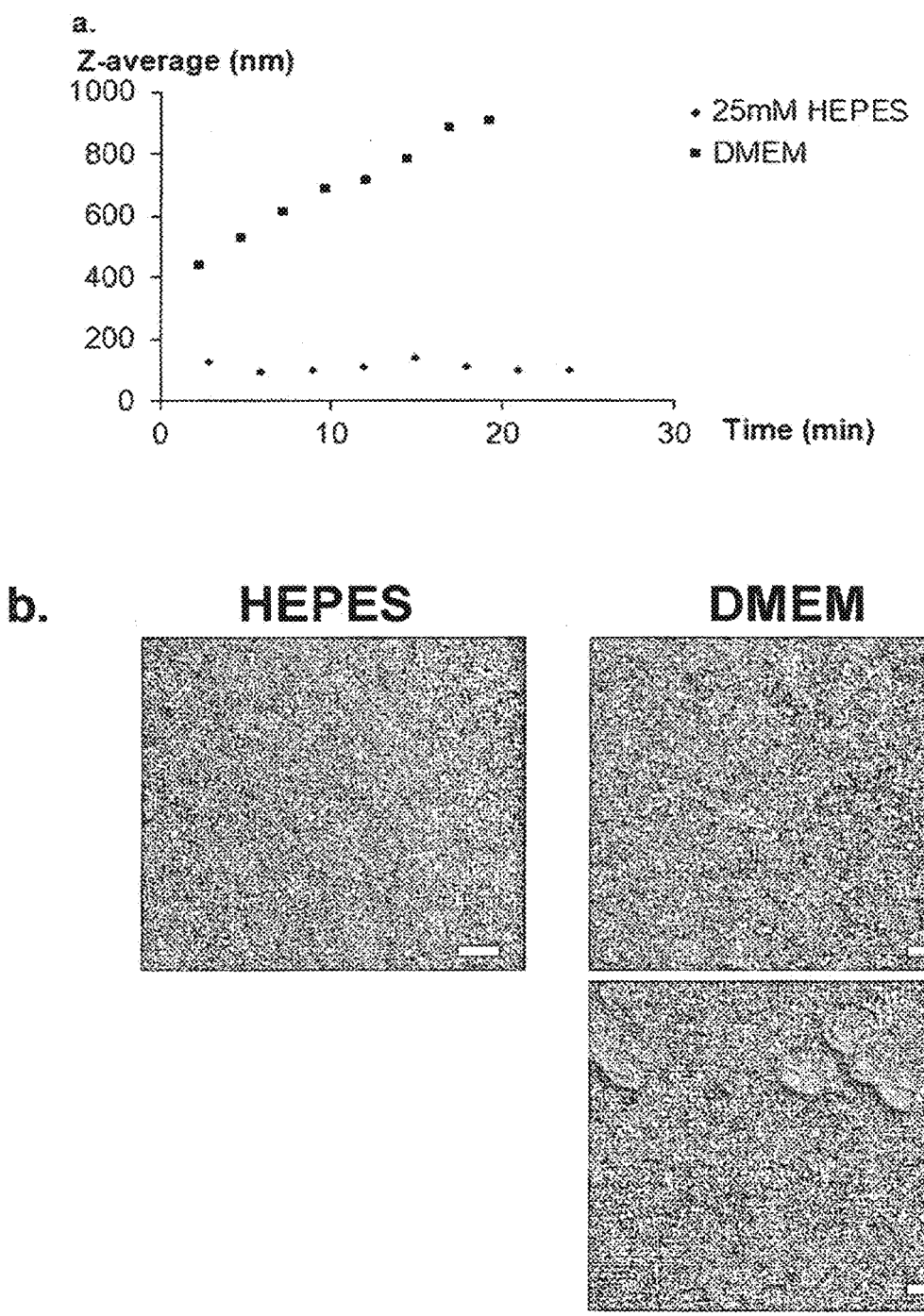

FIG. 13 shows, using a scatter plot and micrographs, that polyplexes aggregated and deposited in DMEM. A. Kinetic analysis of polyplex (N/P=20) size growth in HEPES or DMEM as measured by Dynamic Light Scattering over a period of 25 min. B. LPEI/FITC-pDNA (N/P=20) was prepared and incubated in either HEPES or, DMEM for 15 min. In the absence or presence of Neuro2A cells, the transfection mixtures were centrifuged. Representative merged images of DIC and fluorescence were presented. Bars represent 10 µM.

Figure 14:
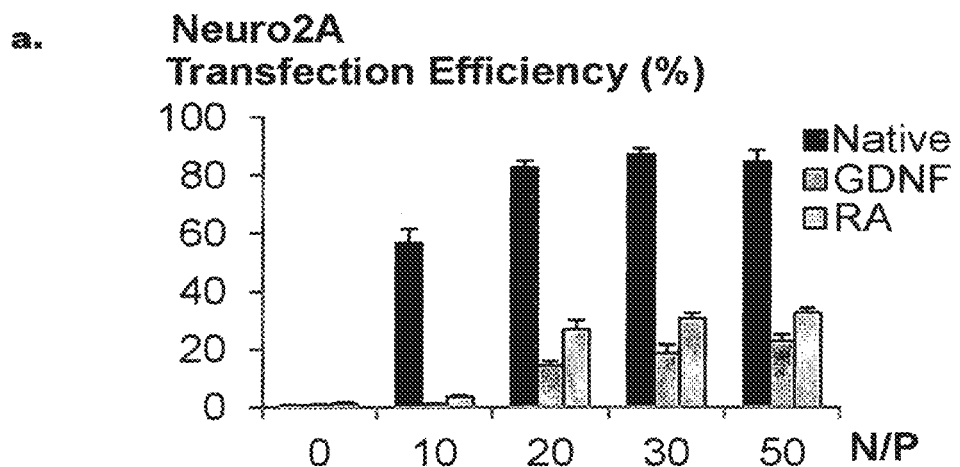
Figure 14:
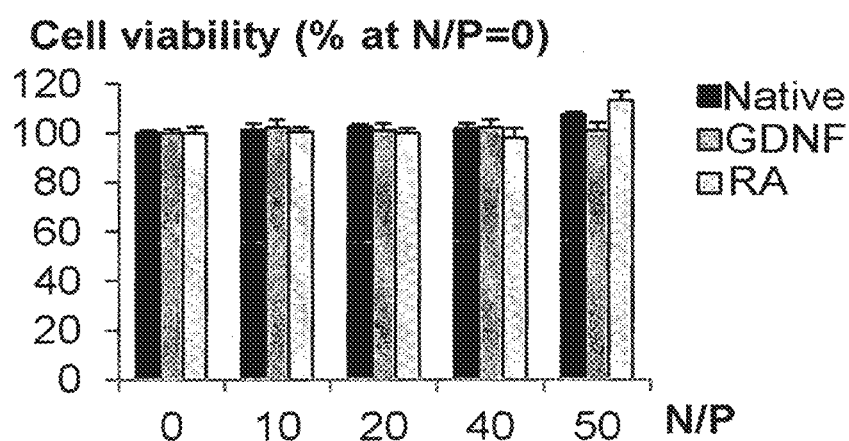
Figure 14:
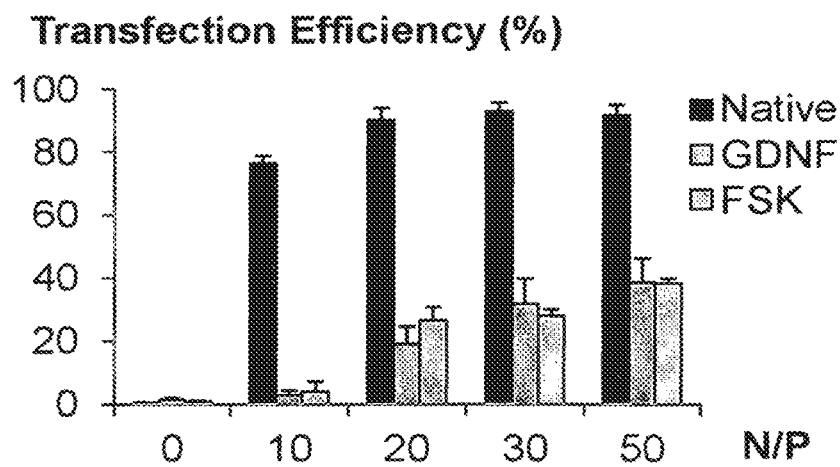
Figure 14:
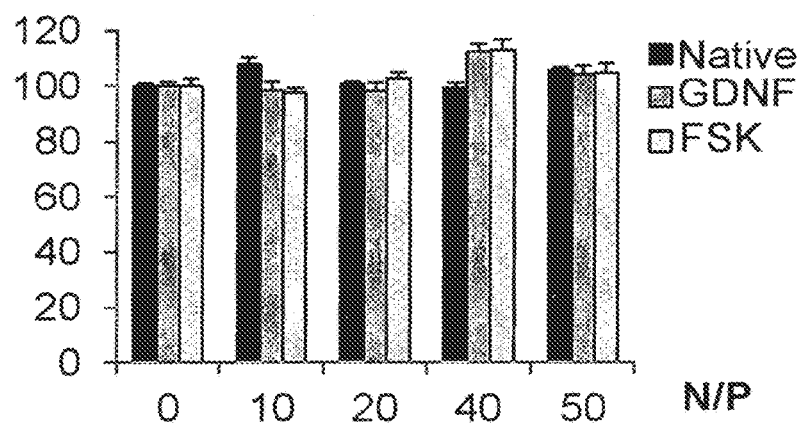

FIG. 14 shows micrograph depicting data that mild centrifugation and short incubation durations resulted in high transfection efficiency at low toxicity. Native and differentiated A. Neuro2A and B. NG-108 cells were transfected with LPEI/pDNA at various N/P ratios using the centrifugation transfection procedure. Cell viability and transfection efficiency was measured 48 h post transfection using cell viability assay and FACS, respectively. Transfection efficiencies and cell viability shown were the mean±s.e.m. (n=4) and mean±s.e.m. (n=6) respectively.

Figure 15:
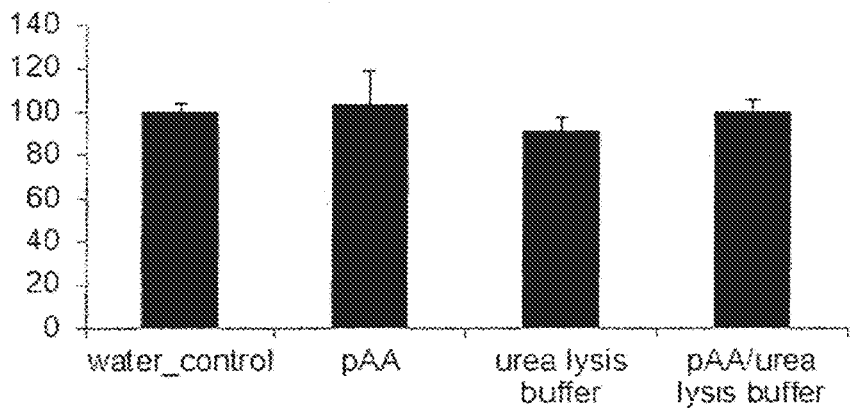
Figure 15:
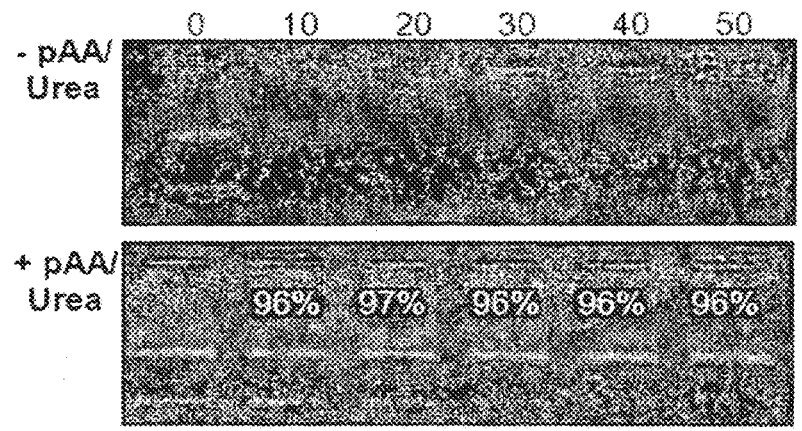
Figure 15:
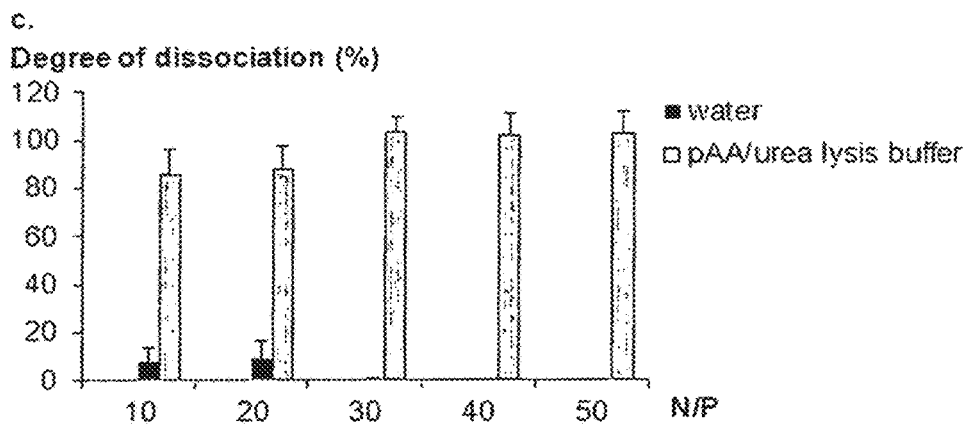

FIG. 15 shows column graphs and an image of a gel electrophoresis that pAA/urea lysis buffer efficiently dissociated polyplexes. A. Plasmid ($10^6$ copies) in different solutions (water, pAA, urea lysis buffer and pAA/urea lysis buffer) was quantified by qPCR and normalized to control (pDNA in water). The lysis solution used did not affect the amplification efficiency of qPCR. LPEI/pDNA at different N/P ratios was treated with pAA/urea lysis buffer or water at 95° C. for 30 min. Subsequently, samples were analysed by B. gel retardation assay and C. qPCR. Data shown were mean±s.e.m. (n=3).

Figure 16:
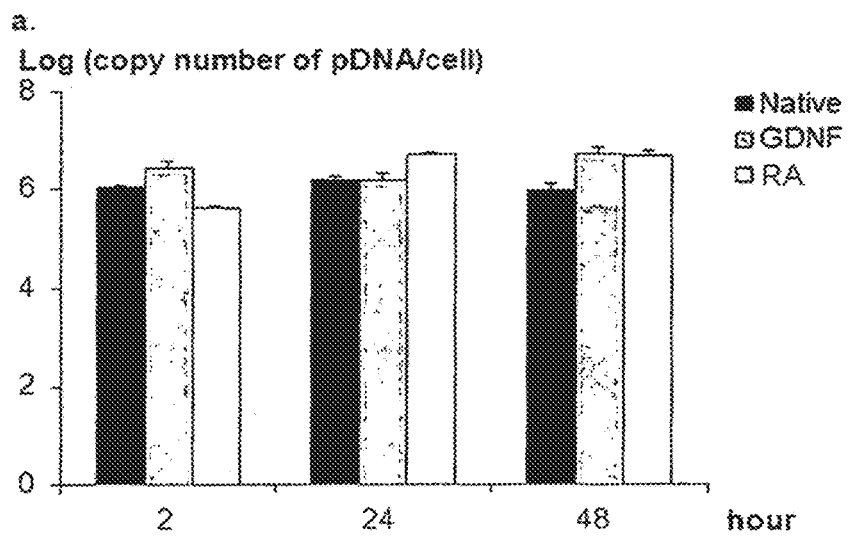
Figure 16:
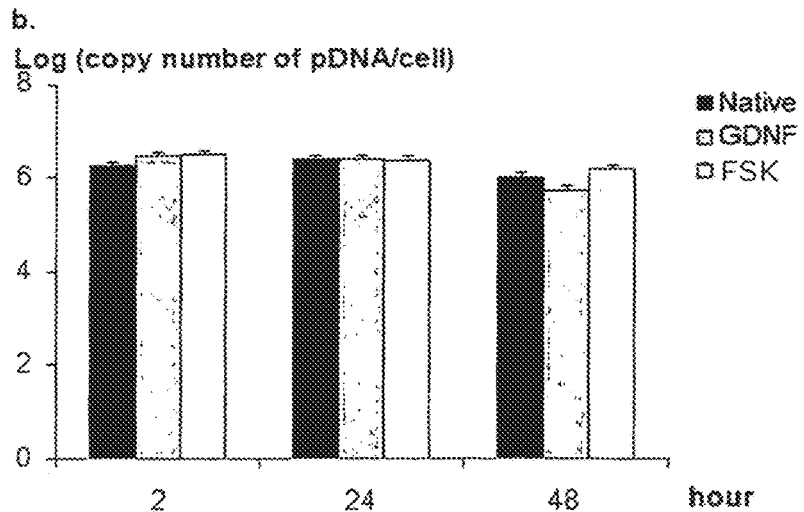

FIG. 16 shows histograms showing that the cellular binding of polyplexes was not affected after neuronal differentiation. A. Neuro2A and B. NG-108 were transfected by LPEI/pDNA (N/P=20) via centrifugation transfection procedure. Cells were harvested at different time points post transfection and treated with pAA/urea lysis buffer. Absolute copy number of pDNA associated with cells was quantified using realtime qPCR. The data shown were the mean±s.e.m., n=3.

Figure 17:
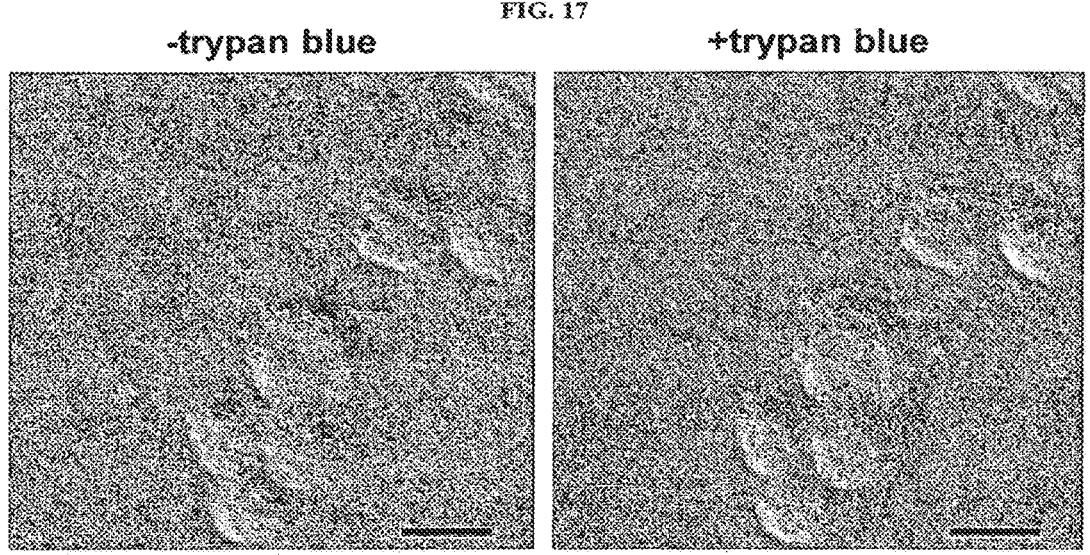

FIG. 17 shows bright field images that trypan blue efficiently quenched surface bound LPEI-Rho labelled DNA complexes. LPEI/Rhodamine-pDNA complexes (N/P=20) were first deposited onto Neuro2A cells. Next, transfection mixture was replaced with iced cold complete media and further incubated for 4 h at 4° C. Then, trypan blue was added. Cell images were taken before and after quenching by 0.4% trypan blue. As internalization is inhibited at 4° C., the surface bound fluorescent labelled DNA was efficiently quenched. Bar represents 20 µm.

Figure 18:
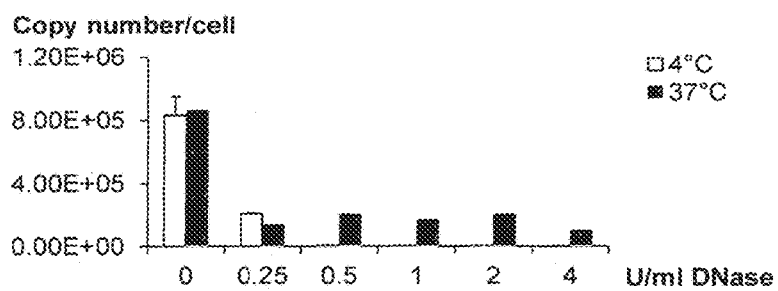
Figure 18:
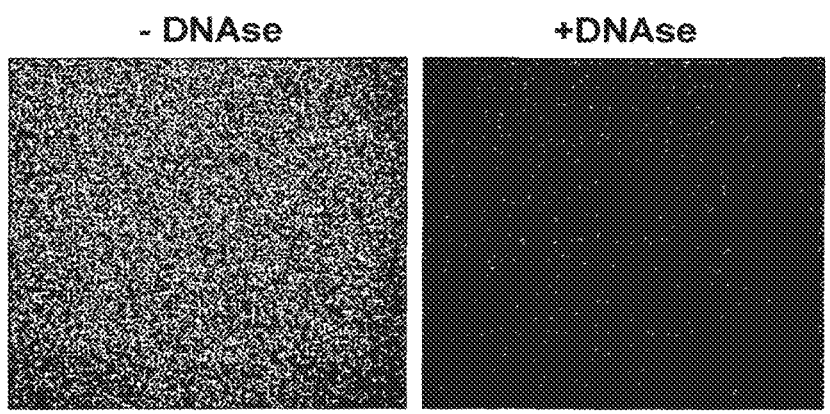

FIG. 18 Data shown as column graphs and fluorescent images show that DNAse efficiently removed surface bound polyplexes. A. LPEI/pDNA (N/P=20) pre-complexed in DMEM was deposited on Neuro2A cells after centrifugation. Cells were incubated at 4° C. or 37° C. for 4 h and treated with pAA/DNase in DMEM to remove extracellular pDNA. Two hours later, cells were harvested by trypsinization and treated with pAA/urea lysis buffer before quantification of internalized pDNA using qPCR. The data shown were the mean±s.e.m., n=4. B. After deposition of polyplexes, wells were washed once with PBS and replenished with (DMEM with or without pAA/DNAse). Surface bound polyplexes were visualized by Sybr Green I staining in 1×PBS and incubated for 5 min. After 1× wash with PBS, images were captured at 10× magnification. Representative images were shown.

Figure 19:
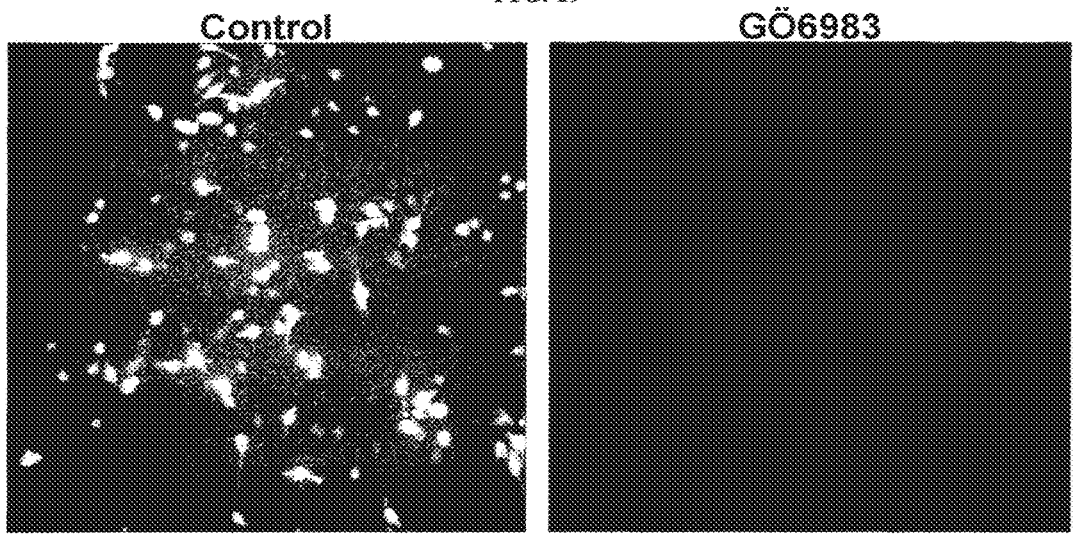

FIG. 19 shows fluorescent images showing that PKC inhibitor substantially reduced transfection. Neuro2A cells were treated with GÖ6983 (2 µM) for 45 min prior transfection. Transfection mixture (LPEI/pDNA at N/P=20) was replaced with DMEM containing 0.5% FBS and GÖ6983 (2 µM). Representative images (acquired 24 h post transfection) were shown.

Figure 20:
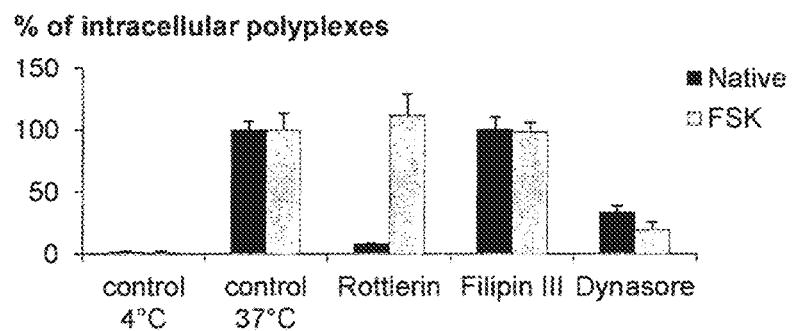
Figure 20:
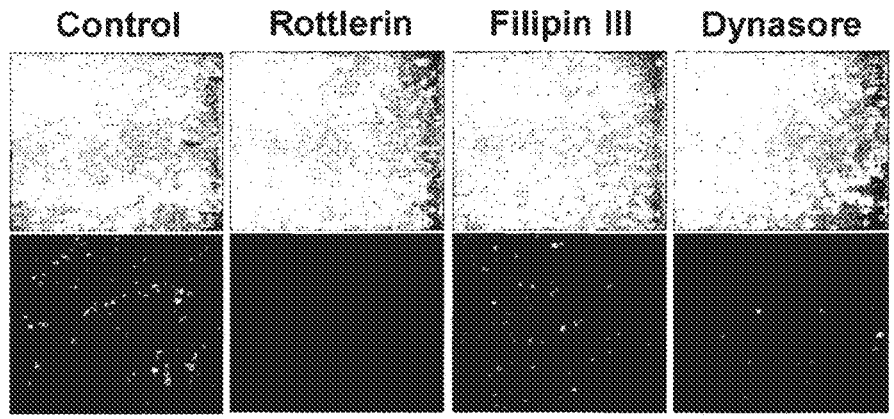
Figure 20:
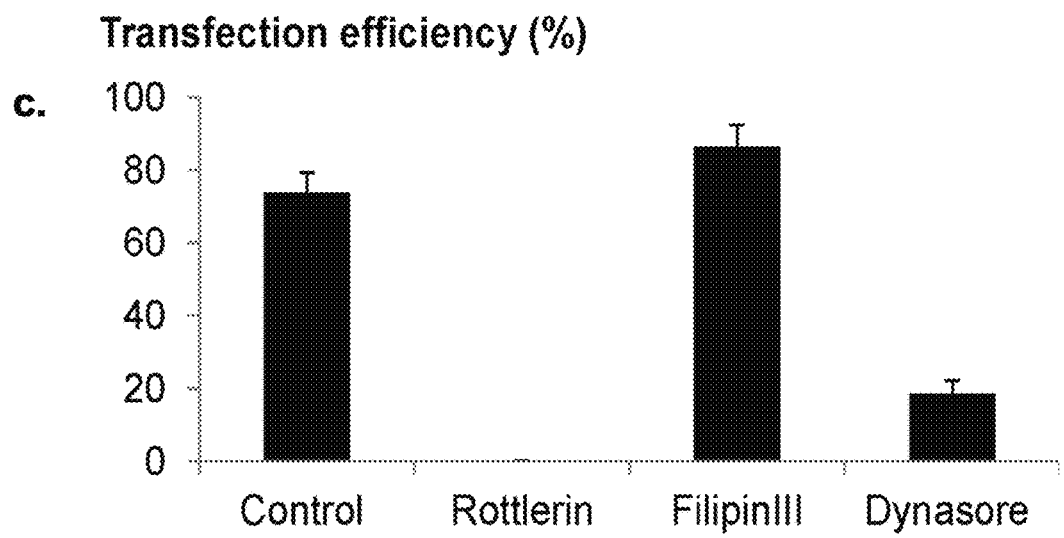

FIG. 20 visualises data, here as histograms and fluorescent images that shows that PKC involved in the uptake of polyplexes in native but not differentiated neuronal cells. A. Native and differentiated (10 µM FSK) NG-108 was treated with rottlerin, Filipin III or Dynasore for 45 min prior transfection. DMSO/0.5% FBS was used as control for treatment. After transfection (LPEi/pDNA at N/P=20), cells were incubated at 4° C. or 37° C. for 4 h. Extracellular pDNA was removed by pAA/DNAse and cells were trypsinized. Then, samples were treated with pAA/urea lysis buffer and absolute copy number of pDNA was quantified by qPCR. In similar experiments, native NG-108 cells were incubated at 37° C. for 24 h post transfection. B. Representative images were shown and C. percentage of cells expressed EGFP was acquired through manual cell count. The data shown were the mean±s.e.m., n=4.

Figure 21:
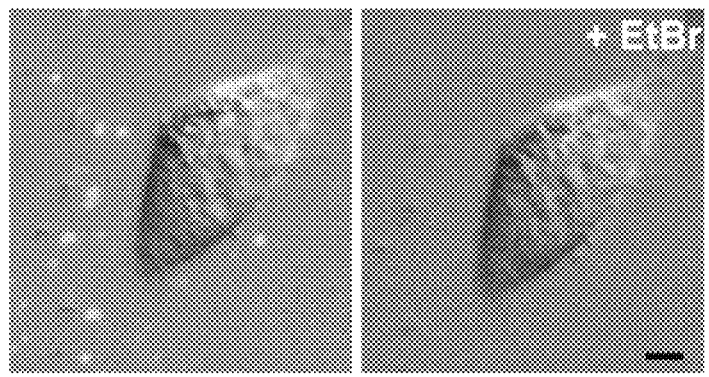
Figure 21:
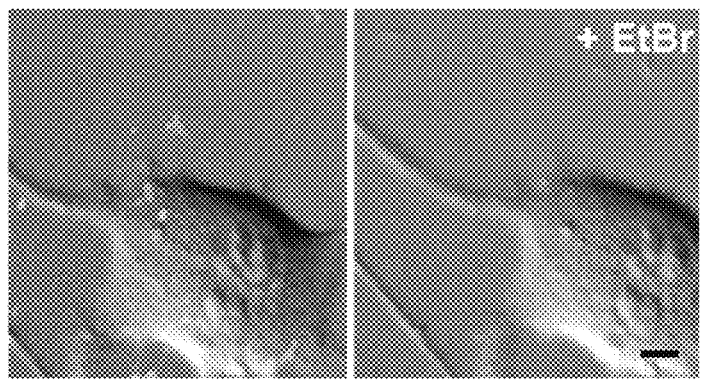
Figure 21:
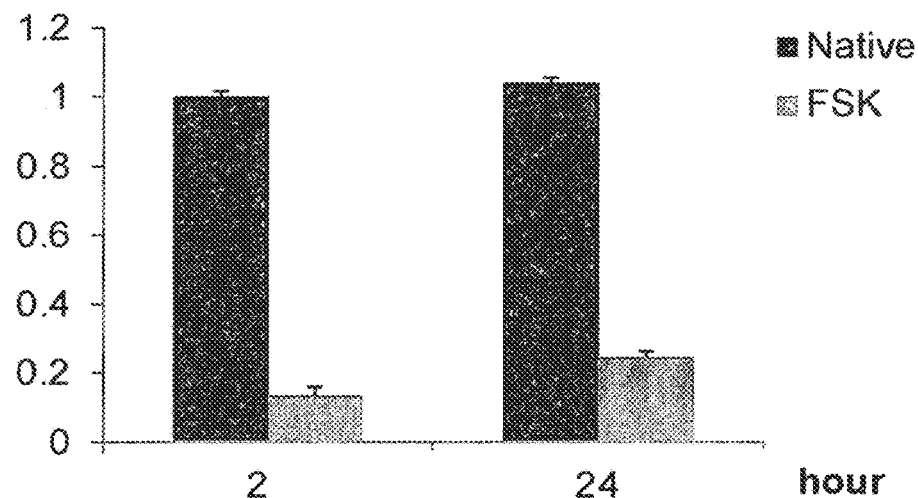

FIG. 21 shows micrographs images depicting that the fluorescence of FITC-pDNA was quenched in differentiated, but not native neuronal cells. A. Native and differentiated (10 µM FSK) NG-108 cells were transfected by LPEI/FITC-pDNA (N/P=20). Quenching reagent, EtBr (20 µg/ml), was added 4 h post transfection. Cell images were taken before and after quenching by EtBr. Bar represents 5 µm. B. Cells were transfected by pre-complexed LPEi/FITC- or Rhodamine-pDNA. Percentage of cells associated with labelled pDNA was acquired after quenching of extracellular fluorescence with EtBr or trypan blue, at 4 or 24 h post transfection. Ratio of FITC/Rho in native and differentiated NG-108 cells was calculated. The data shown were the mean±s.e.m., n=20.

Figure 22:
Figure 22:
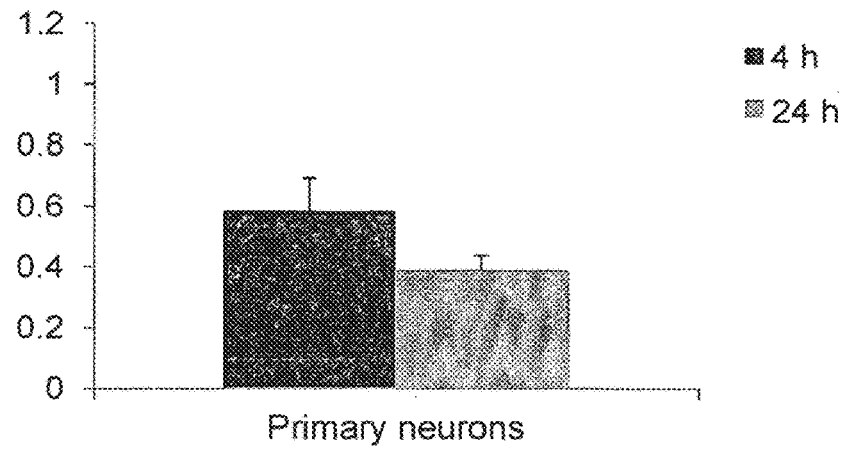

FIG. 22 shows data depicting that the fluorescence of FITC-pDNA was quenched in primary cortical neurons. A. Primary cortical neurons were transfected by LPEI/FITC-pDNA (N/P=20). Quenching reagent, EtBr (20 µg/ml), was added 4 h post transfection. Cell images were taken before and after quenching by EtBr. Bar represents 5 µm. B. Cells were transfected by pre-complexed LPEI/FITC- or Rhodamine-pDNA. Percentage of cells associated with labelled pDNA was acquired after quenching of extracellular fluorescence with EtBr or trypan blue, at 4 or 24 h post transfection. Ratio of FITC/Rho in primary cortical neurons was calculated. The data shown were the mean±s.e.m., n=20.

Figure 23:
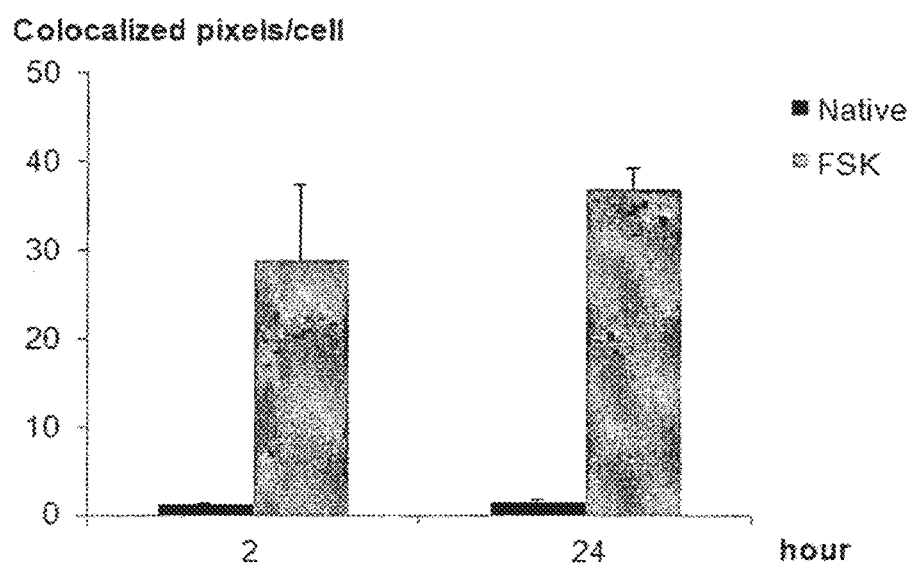

FIG. 23 shows histograms showing that polyplexes localized differentially in native and differentiated neuronal cells. LPEI/Rhodamine-pDNA (N/P=20) were used to transfect native or differentiated (10 µM FSK) NG-108 cells with centrifugation transfection procedure. Four hours later, culture media was removed and replenished with 1×PBS containing 50 nM Lysotracker green DND-26 and the incubation continued for 5 min before observation by confocal microscopy. Images of single cell were captured at 100× magnification. Co-localized pixels of Rhodamine with lysotracker green DND-26 was analysed. The data shown were the mean±s.e.m., n=20.

Figure 24:
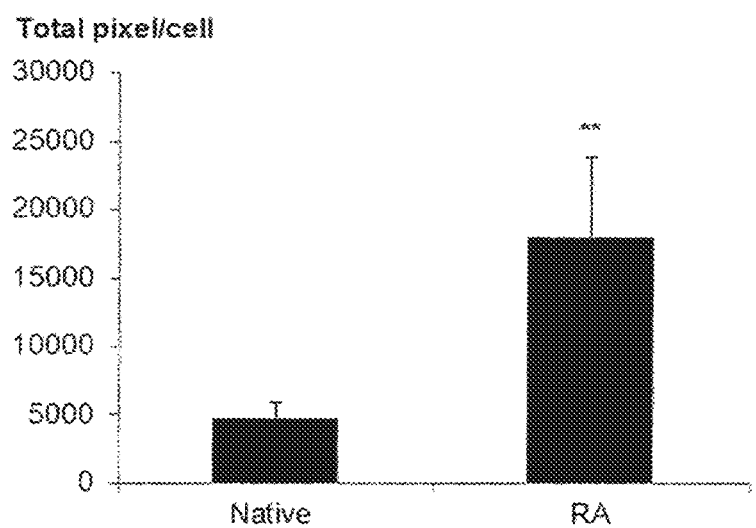

FIG. 24 shows histograms visualising the amount of acidic compartment increased after neuronal differentiation. Native and differentiated (10 µM RA) Neuro2A was incubated in PBS containing Lysotracker Green. Total pixel of labelled acidic compartment was obtained by summing pixels of Z-stack images (whole cell). Significant differences in total pixels/cell were calculated using the two tailed student's t-test. The data shown were the mean±s.e.m., n=20 for each phenotype. **, P<0.005.

Figure 25:
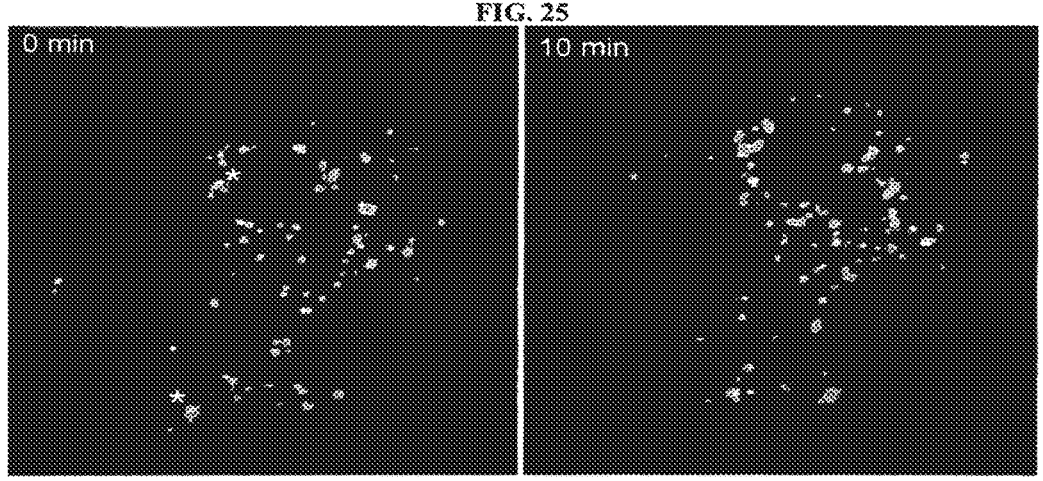

FIG. 25 shows micrograph images, depicting that the endosomal release of labeled pDNA happened after addition of DOPE/CHEMS. Differentiated Neuro2A cells were transfected with LEPI/Rhodamine-pDNA complexes (N/P=20), and further incubated for 4 h. Then, lysotracker green and DOPE/CHEMS were added and images were taken continuously for 20 min. Real-time tracking demonstrated release of polyplexes (indicated by asterisks) from the acidic compartments. Measurement bar represents 5 µm.

Figure 26:
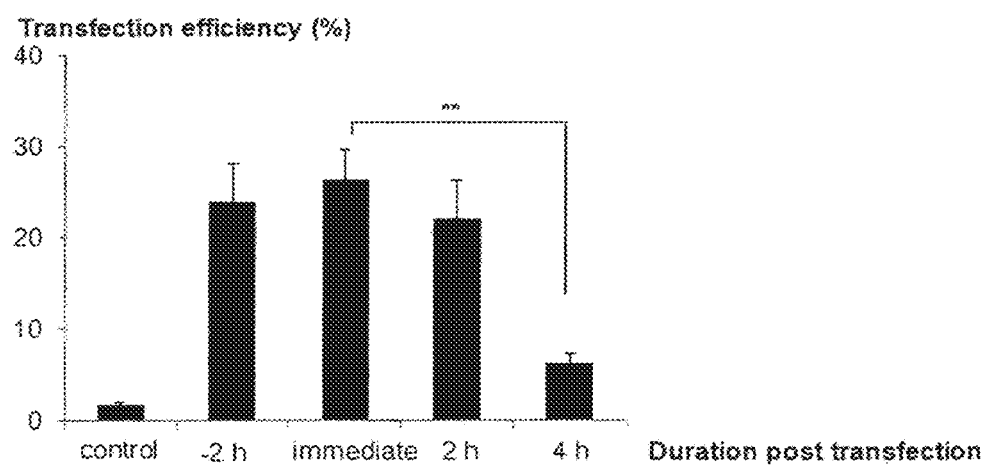

FIG. 26 shows histograms, depicting the effect of DOPE/CHEMS being time-dependent. LPEI/pDNA (N/P=20) was used to transfect differentiated (10 µM RA) Neuro2A cells. DOPE/CHEMS was added at different time point post transfection. Transfection efficiency was acquired by counting fluorescent and bright field images for EGFP+ cells after 24 h of incubation. Percentage of EGFP positive cells bearing neurites twice the cell body length was presented as mean±s.e.m (n=4). Significant differences in transfection efficiencies were calculated using the two tailed student's t-test. **, p<0.005.

Figure 27:
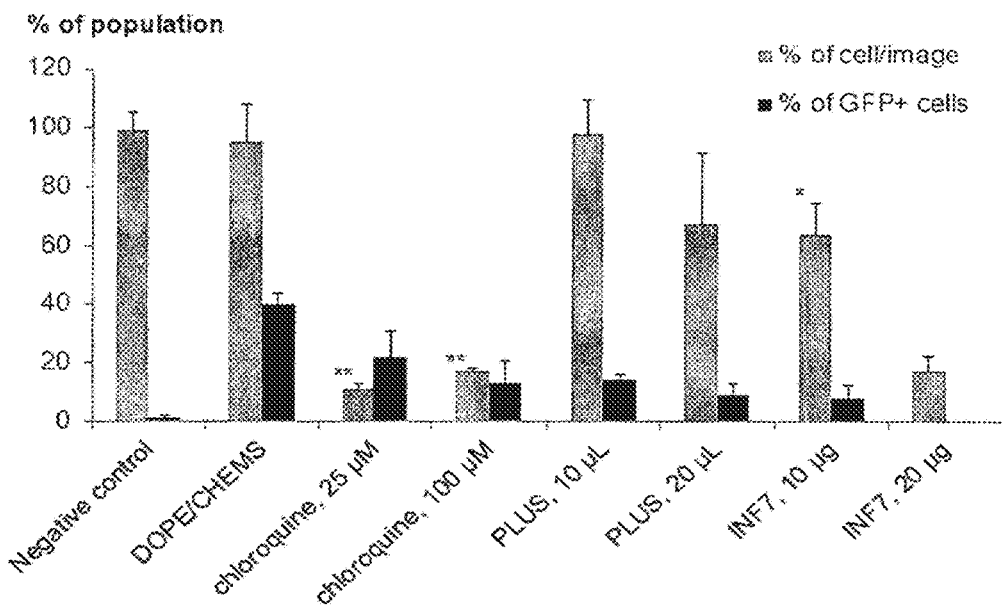

FIG. 27 shows column graphs, the data of which indicates that commercial reagents did not show cumulative enhancement of transfection. Pre-complexed LPEI/pDNA (N/P=20) was used to transfect differentiated (10 µM RA) Neuro2A cells. Chloroquine (25 µM or 100 µM), PLUS reagent (10 µL or 20 µL) or INF7 fusogenic peptide (10 µg or 20 µg) was added post-transfection. Transfection efficiency and cell viability was acquired by counting fluorescent and bright field images for EGFP+ cells after 48 h of incubation. Percentage of EGFP positive cells bearing neurites twice the cell body length was presented as mean±s.e.m (n=3). Significant differences in cell viability (% of cell/image) against control (polyplexes only) were calculated using the two tailed student's t-test. *, p<0.05, **, p<0.005.

Figure 28:
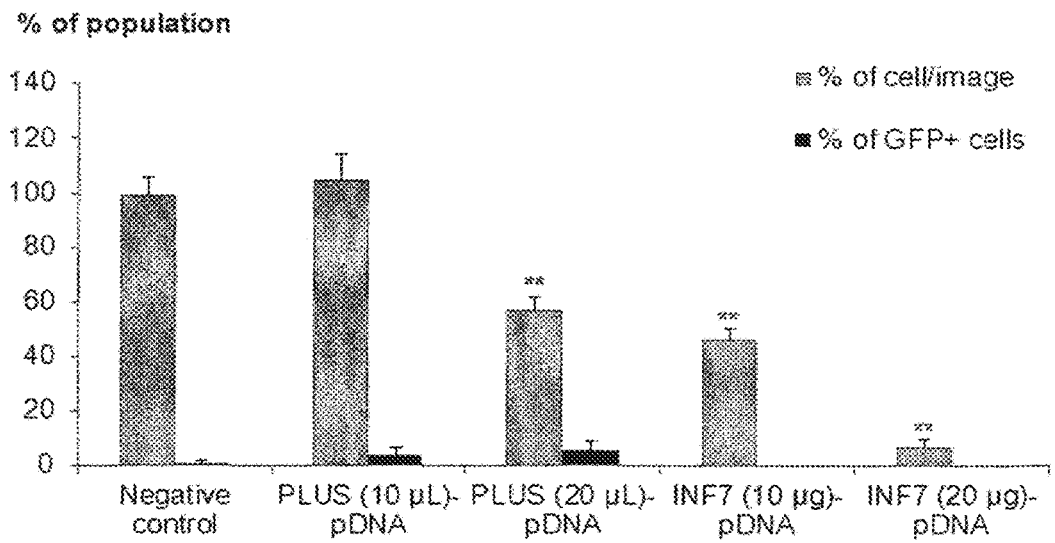

FIG. 28 shows column graphs, showing that LPEI/fusogenic reagent-pDNA complexes did not yield a significant improvement of transfection. Plasmid DNA (2 µg) was incubated with PLUS reagent (10 µL or 20 µL) or INF7 fusogenic peptide (10 µg or 20 µg) for 15 min prior to complexation with LPEI (N/P=20). The polyplexes were then used to transfect differentiated (10 µM RA) Neuro2A cells. Transfection efficiency and cell viability was acquired by counting fluorescent and bright field images for EGFP+ cells after 48 h of incubation. Percentage of EGFP positive cells bearing neurites twice the cell body length was presented as mean±s.e.m (n=3). Significant differences in cell viability against control were calculated using the two tailed student's t-test. **, p<0.005.

Figure 29:
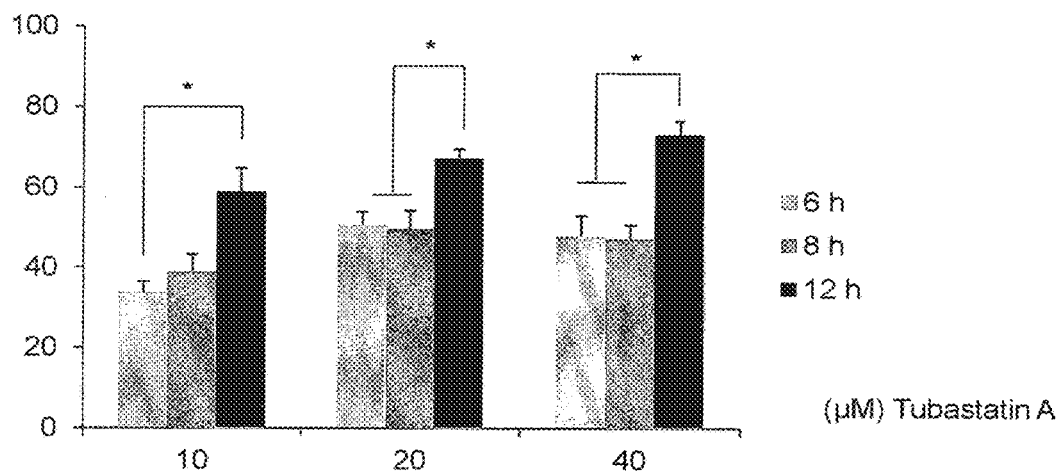

FIG. 29 shows, as column graphs, that a minimal duration of incubation with DOPE/CHEMS and Tubastatin A is required for high transfection efficiency. LPEI/pDNA (N/P=20) were used to transfect of differentiated Neuro2A (stimulated by 20 µM RA). Cells were treated with DOPE/CHEMS and Tubastatin A (5, 10 or 20 µM) for 6, 8 or 12 h. Chemicals were removed by replacement with complete media and cells were further incubated for 48 h. Transfection efficiency was acquired by counting fluorescent and bright field images for EGFP+ cells. Data presented group mean±s.e.m (n=3). Significant differences in transfection efficiencies were calculated using the two tailed student's t-test. *, p<0.05.

Figure 30:
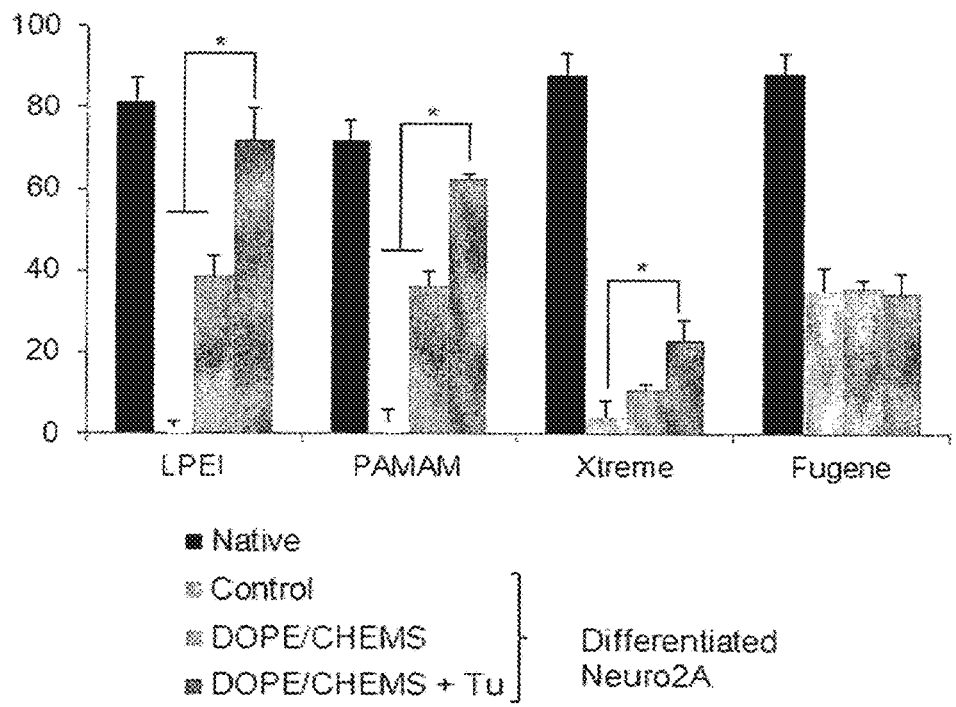

FIG. 30 shows histograms depicting the data that DOPE/CHEMS and Tubastatin A enhanced transfection efficiency was mediated by some but not all cationic carriers. LPEI/pDNA (N/P=20), PAMAM/pDNA (N/P=10), XTREMEGENE HP/pDNA (3 µL: 1 µg of pDNA) and Fugene HD (1.5 µL: 1 µg of pDNA) were used to transfection undifferentiated and differentiated Neuro2A (10 µM RA). Cells were treated with DOPE/CHEMS, Tubastatin A (10 µM) or DOPE/CHEMS and Tubastatin A (10 µM) for 12 h. Control indicates cells exposed to DNA complexes only. Chemicals were removed by replacement with complete media and cells were further incubated for 48 h. Transfection efficiency was acquired by counting fluorescent and bright field images for EGFP+ cells. Data presented group mean±s.d. (n =3). Significant differences in transfection efficiencies were calculated using the two tailed student's t-test. *, p<0.05.

Figure 31:
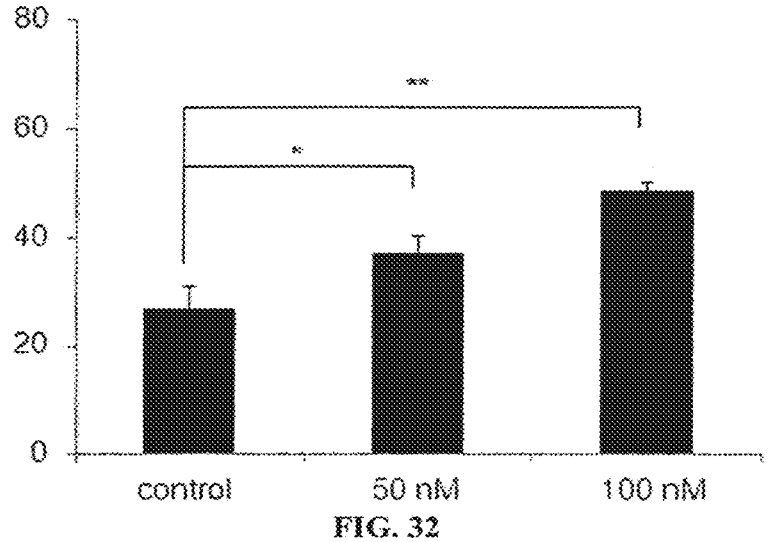

FIG. 31 shows a graph depicting the data that Trichostatin A enhanced transfection. LPEI/pDNA (N/P=20) were used for transfection of differentiated (10 µM RA) Neuro2A cells. In the presence of DOPE/CHEMS, Trichostatin A (50 and 100 nM) was added 1 h post transfection. Transfection efficiency was acquired 24 h later by counting fluorescent and bright field images for EGFP+ cells after 24 h of incubation. Percentage of EGFP positive cells bearing neurites twice the cell body length was presented as mean±s.e.m (n=3).

Figure 32:
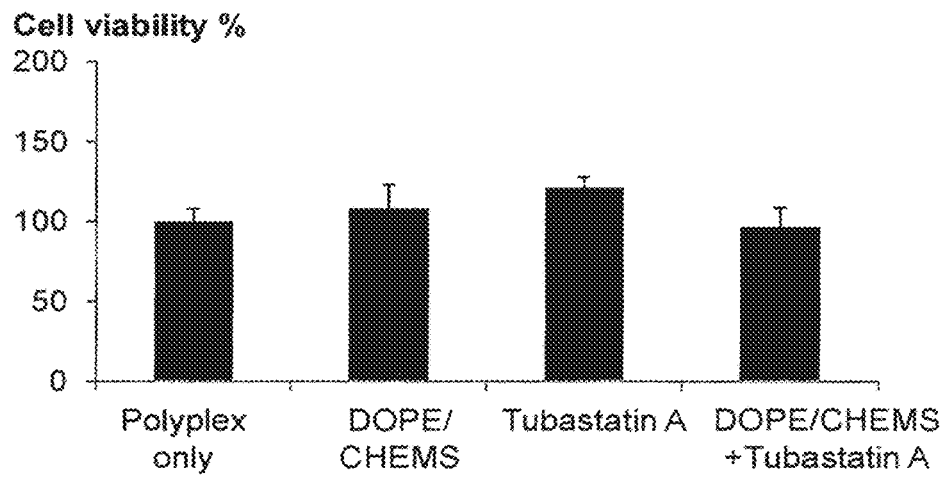
Figure 32:
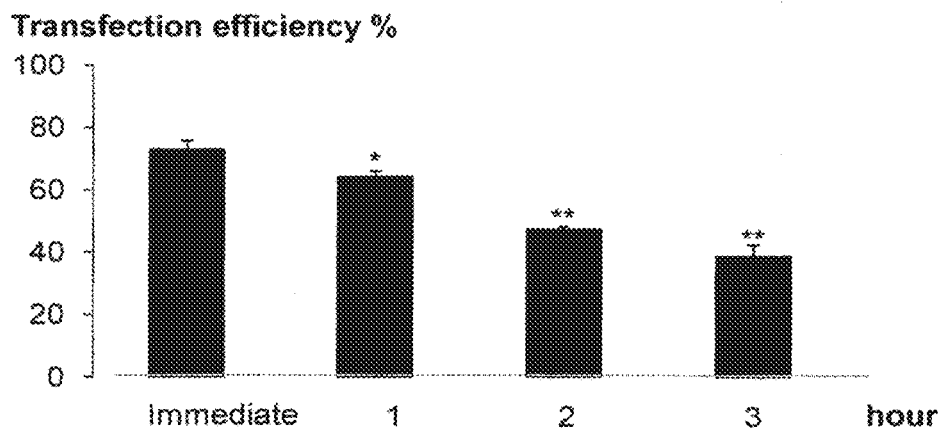

FIG. 32 shows histograms representing the data showing that DOPE/CHEMS and Tubastatin A led to high transfection efficiency and low toxicity in primary cortical neurons. LPEI/pDNA (N/P=20) were used to transfect of primary cortical neurons by centrifugation transfection procedure. Cells were incubated in neurobasal media containing DOPE/CHEMS and Tubastatin A (16 µM) for 24 h. Chemicals were removed by replacement with fresh neurobasal media and cells were further incubated for 24 h. A. Cell viability was obtained by counting total number of cells per bright field image and normalized by control (without DOPE/CHEMS and Tubastatin A). Data presented group mean±s.e.m (n=4). B. In the presence of DOPE/CHEMS, Tubastatin A (16 µM) was added to the primary cortical neurons culture immediately, 1, 2 and 3 h post transfections. Transfection efficiency was quantified by FACS analysis 48 h later and presented as mean±s.d (n=3). Significant differences in transfection efficiencies were calculated using the two tailed student's t-test. *, p<0.05; **, p<0.005.

Figure 33:
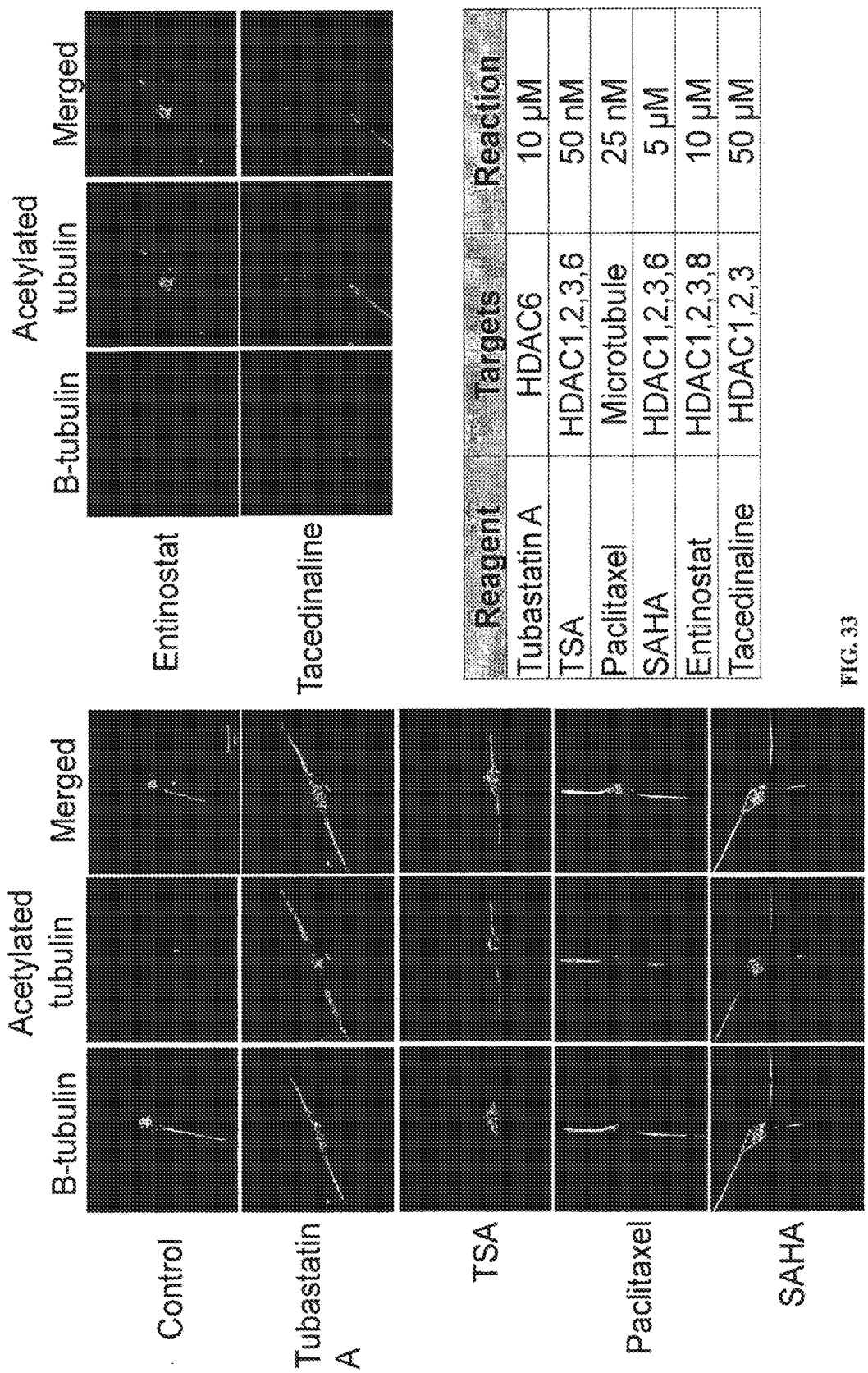

FIG. 33 shows micrographs of HDAC6 inhibition and that treatment with paclitaxel resulted in tubulin acetylation. Differentiated Neuro2A cells (pre-treated with 10 µM RA)

were exposed to HDAC inhibitors such as Tubastatin A (10 μM), TSA (50 nM), Paclitaxel (25 nM), SAHA (5 μM), Entinostat (10 μM), or Tacedinaline (50 μM) for 2 h. Then, cells were fixed with 4% formaldehyde and co-stained for acetylated α-tubulin and β-tubulin. Confocal images of the individual and merged channels are shown. Bar represents 20 μm. Further, a table is presented, showing the reagents and their respective targets, as well as the concentration at which the experiment was done.

Figure 34:
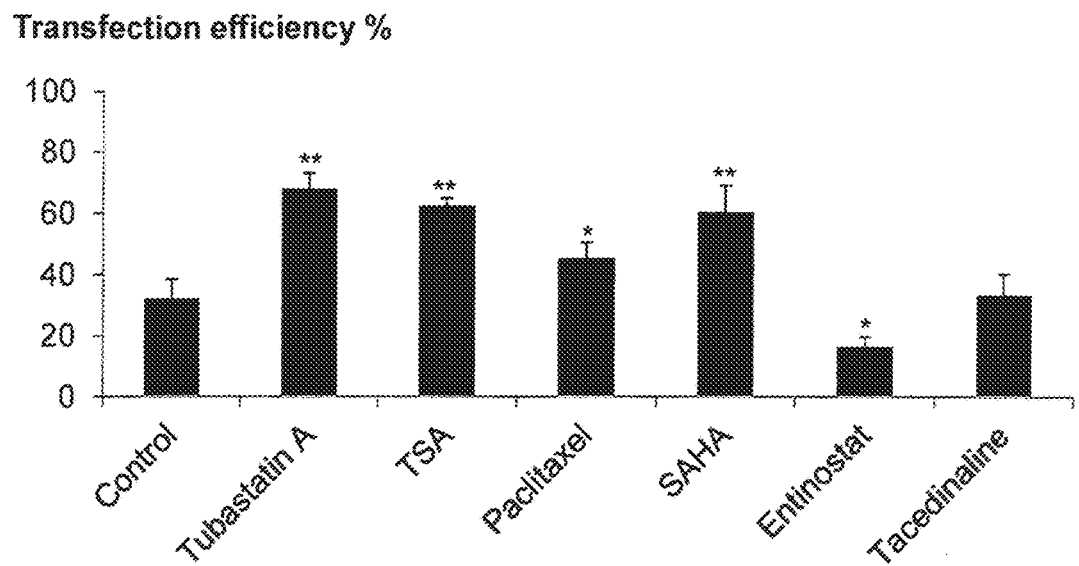

FIG. 34 presents data showing that treatment with DOPE/CHEMS and HDAC6 targeting inhibitors resulted in unprecedented transfection efficiency. LPEI/pDNA (N/P=20) were used to transfect of differentiated neuronal cells (10 μM RA) by centrifugation transfection procedure. Then, cells were exposed to DOPE/CHEMS and Tubastatin A (10 μM), TSA (50 nM), Paclitaxel (25 nM), SAHA (5 μM), Entinostat (10 μM), or Tacedinaline (50 μM) for 12 h. Cell exposed to DOPE/CHEMS served as control. Transfection efficiency was quantified by FACS analysis 48 h later and presented as mean±s.d (n=3). Significant differences in transfection efficiencies were calculated using the two tailed student's t-test. *, $p<0.05$; **, $p<0.005$.

Figure 35:
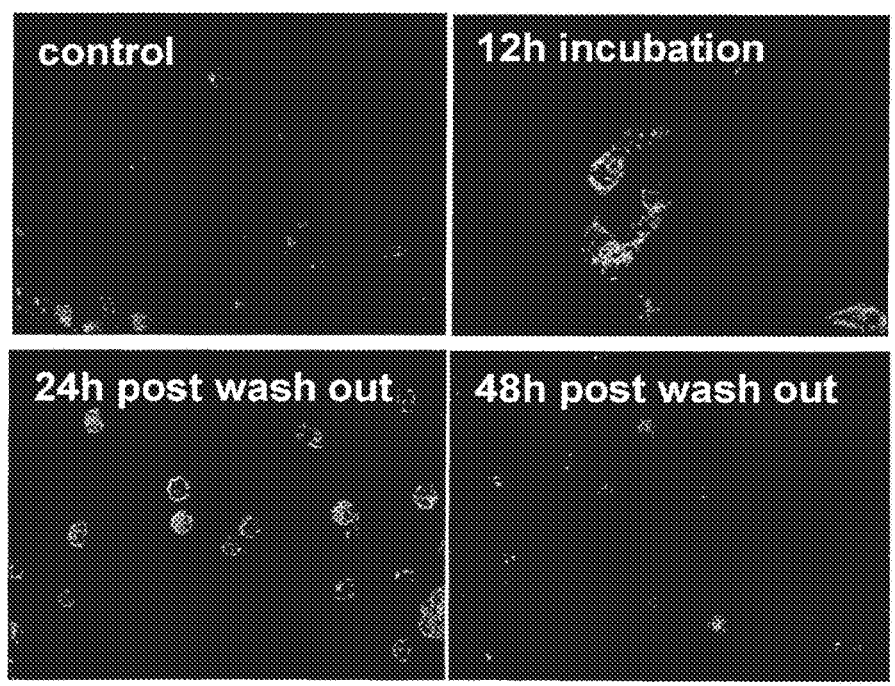

FIG. 35 depicts micrographs showing the transient effect of Tubastatin A on tubulin acetylation. Neuro2a cells were treated with Tubastatin A (10 μM) for 12 hours. Then, chemicals were removed by replacement with complete media and cells were further incubated for 48 h. At various time points, cells were fixed with 4% formaldehyde and stained for acetylated α-tubulin (Green) and nucleus (Hoechst stain, Blue). Representative images were shown. Bar represents 20 μm.

Figures 36, 37:
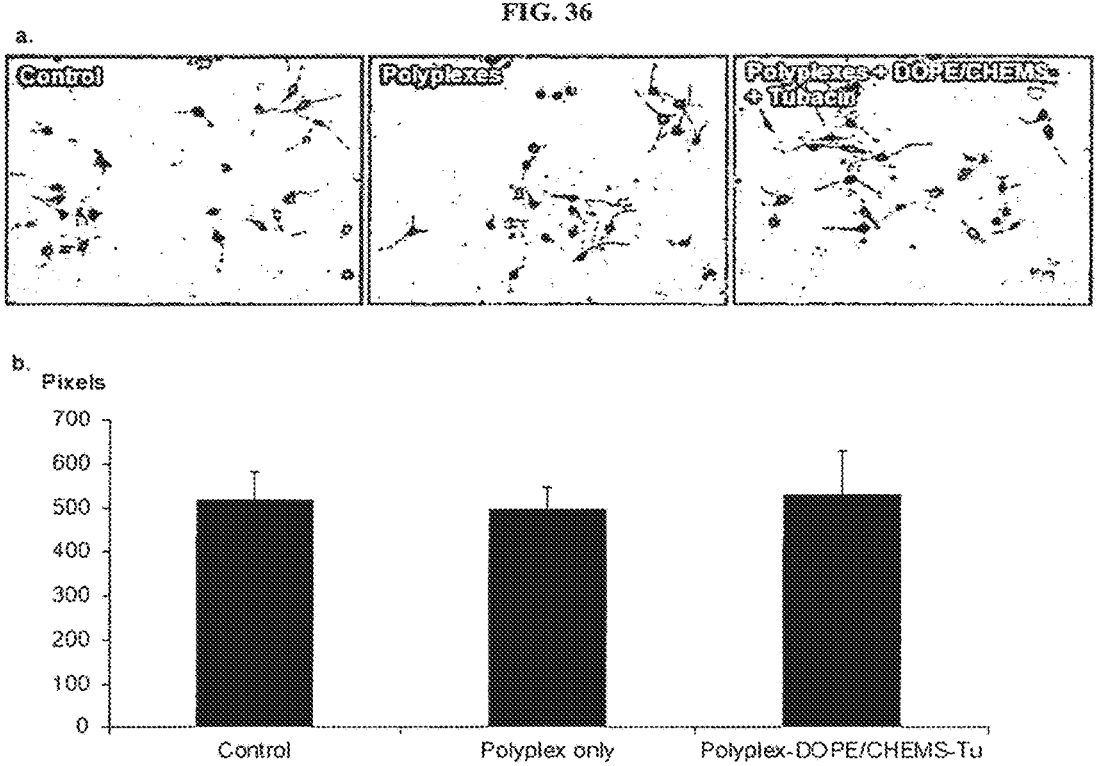
Figure 37:
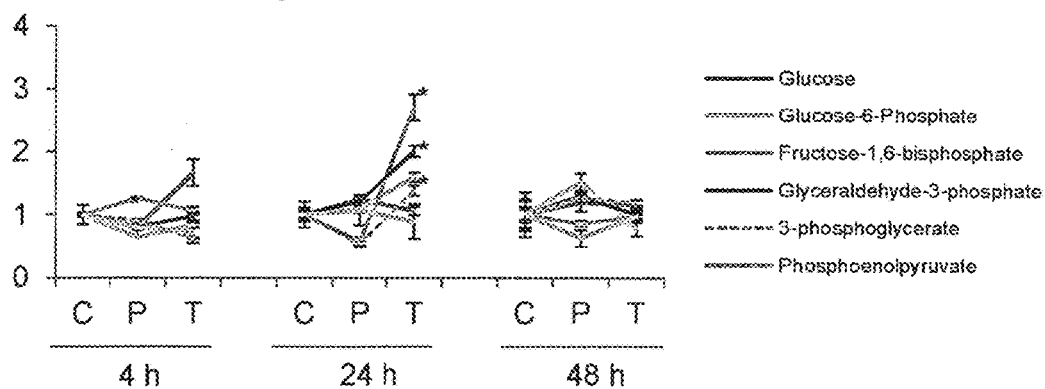
Figure 37:
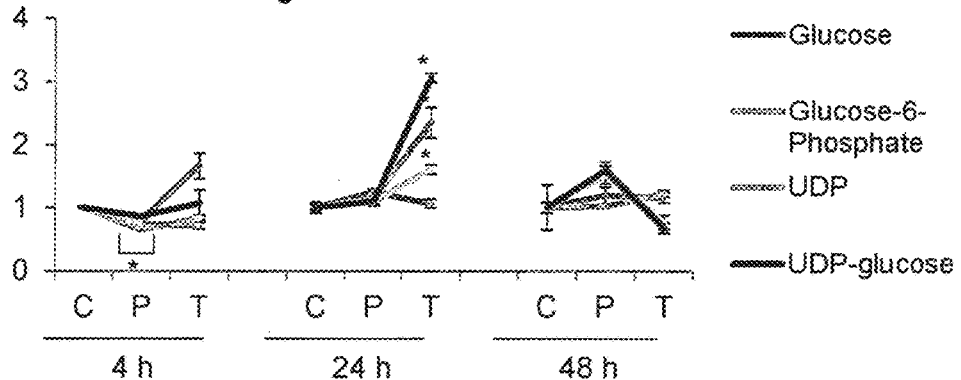
Figure 37:
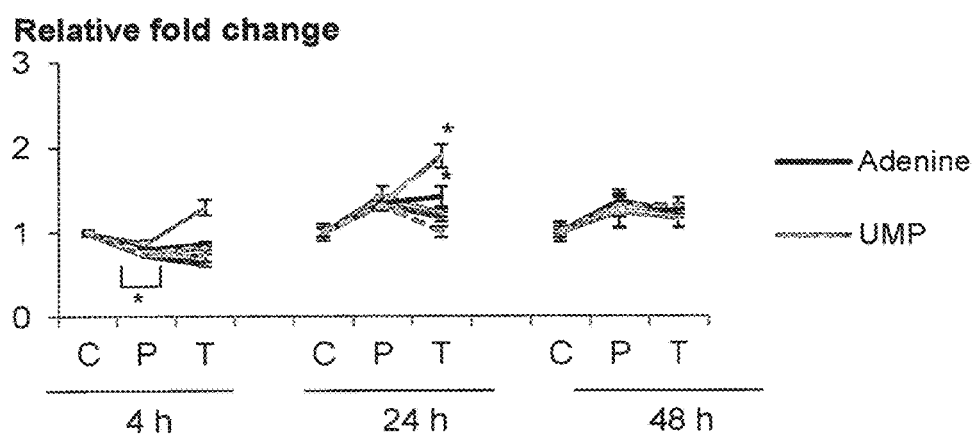
Figure 37:
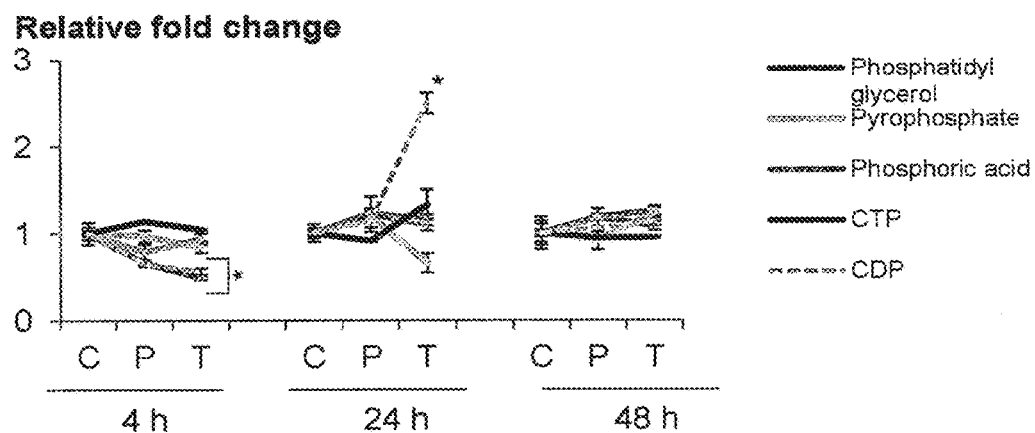
Figure 37:
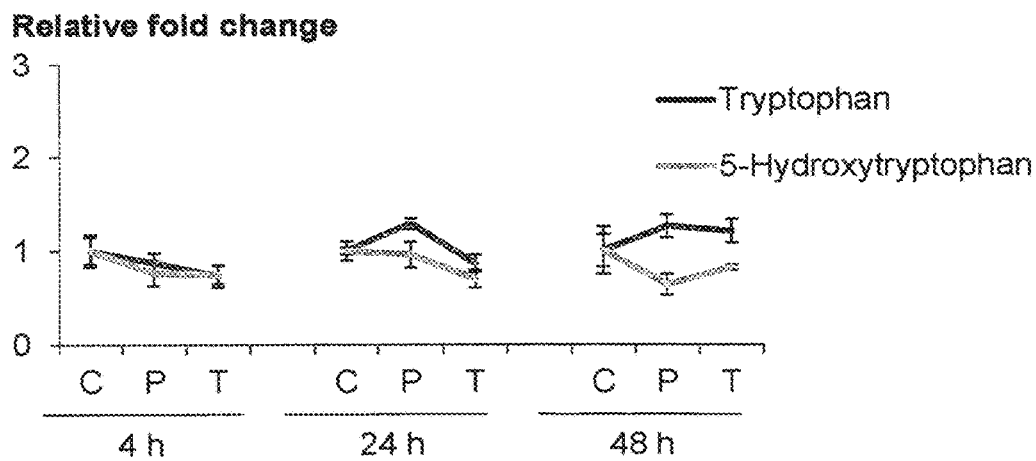

FIG. 36 shows data indicating that neurite outgrowth was not affected by LPEI mediated transfection. Neuro2A cells were transfected by LPEI-pDNA (N/P=20) in the presence or absence of DOPE/CHEMS and Tubastatin A (10 μM). Twelve hour post transfection, cell culture media was removed and replaced with DMEM containing 1% FBS. Six hours later, neuronal differentiation was stimulated by 10 μM RA/1% FBS/DMEM. After 48 h of incubation, cells were fixed with 4% formaldehyde and stained for nucleus (Hoechst stain, Blue) and imperial protein stain. A. shows micrographs of representative images. Bar represents 50 μm. B. shows a histogram showing the average neurite length, which was measured by HCA vision and presented as mean of pixel±s.e.m (n=80-100, biological quadruplicates).

FIG. 37 shows various line graphs, depicting the recovery of global metabolism after washout of DOPE/CHEMS and Tubastatin A. Neuro2A cells were transfected by LPEI-pDNA (N/P=20) in the presence or absence of DOPE/CHEMS and Tubastatin A (10 μM). Negative control indicates cells without treatment throughout the experiment. Twelve hour post-transfection, chemicals were removed by replacement with fresh complete media. Cells were then collected at 4, 24, and 48 h later and subjected to LC/MS analysis for various pathways including A. TCA cycle, B. Glycolysis, C. Glycogen metabolism, D. Nucleotide metabolism, E. Phospholipid synthesis and F. Tryptophan metabolism. At each time point, quantriplicates of negative control (C), cells exposed to polyplexes (P) and cells exposed to both polyplexes, DOPE/CHEMS and Tubastatin A (T) were collected. Relative fold change to negative control was obtained after normalization of each metabolite to the ATP readout, presented as mean±s.d. (n=4). Significant differences in the relative fold change were calculated using the two tailed student's t-test. *, $p<0.05$.

Figure 38:
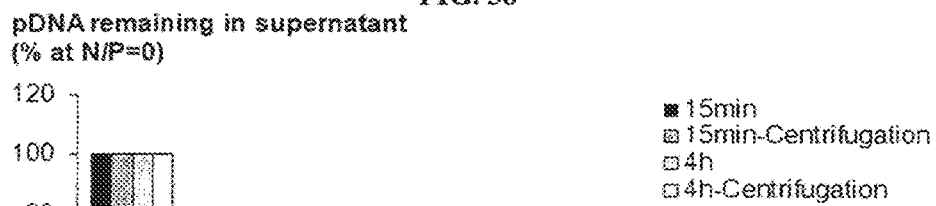

FIG. 38 shows a histogram visualising the data pertaining to polyplex sedimentation. LPEI/pDNA (various N/P ratios) was incubated in DMEM for 15 min or 4 h. At the end of incubation, some samples were centrifuged and all were subsequently treated with pAA/urea lysis buffer. The amount of pDNA in the supernatant was measured by qPCR (normalized to control where N/P=0). The data shown were the mean±s.e.m., n=3.

Figure 39:
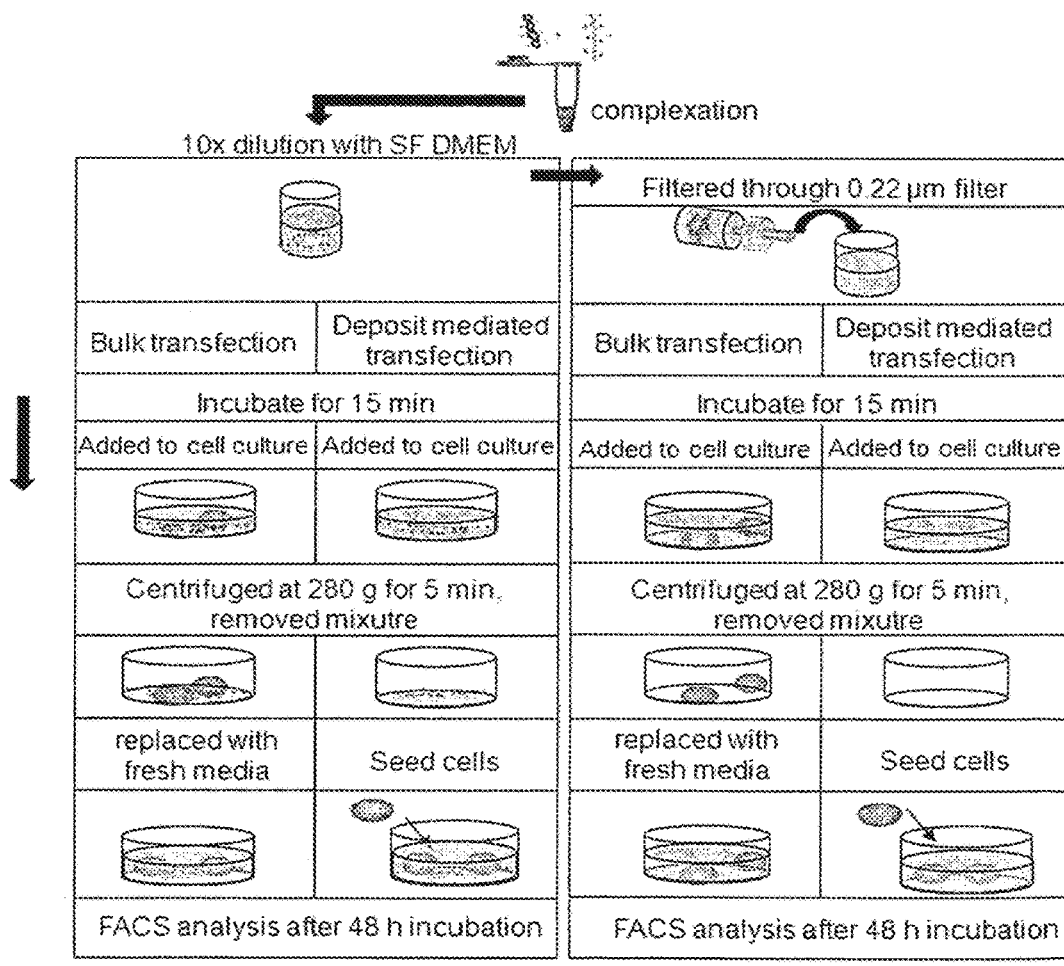

FIG. 39 shows a schematic of the experiment design used in testing the contribution of aggregated polyplexes to transfection. LPEI/pDNA (N/P=20) pre-complexed in DMEM (with or without filtration through 0.22 μm) was centrifuged in the presence or absence of Neuro2a cells. Transfection mixture was replaced by complete media and incubated for 48 h. Transfection efficiency was quantified by flow cytometry.

Figure 40:
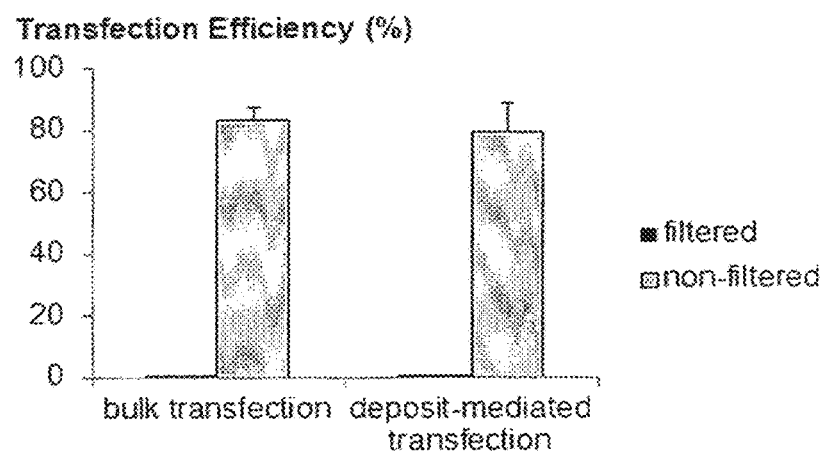
Figure 40:
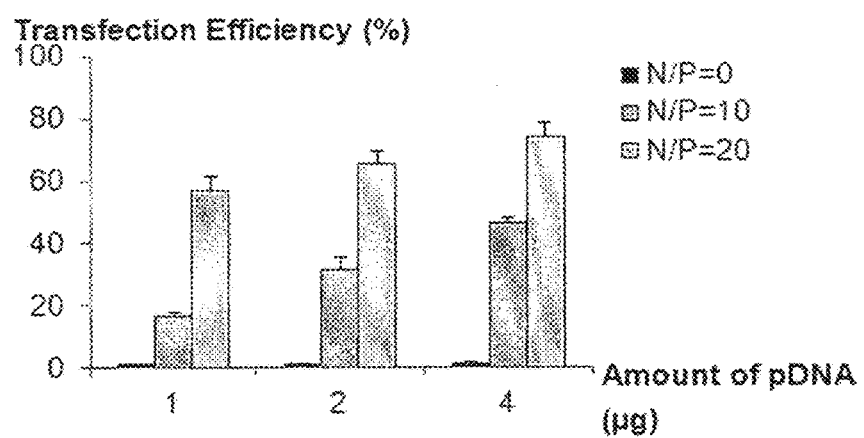

FIG. 40 shows column graphs depicting that aggregated polyplexes mediated efficient transfection. A. Neuro2A cells were transfected with LPEI/pDNA (N/P=20) pre-complexed in DMEM (with or without filtration) by bolus or deposited mediated transfection procedures. Transfection efficiency was quantified by FACS 48 h later. The data shown are the mean±s.d., n=3. B. Neuro2A cells were transfected by LPEI complexed with various amount of pDNA at N/P=0, 10, 20 via deposit mediated transfection procedure. Transfection efficiency was quantified by FACS after 48 h incubation. The data shown were the mean±s.e.m., n=3.

Figure 41:
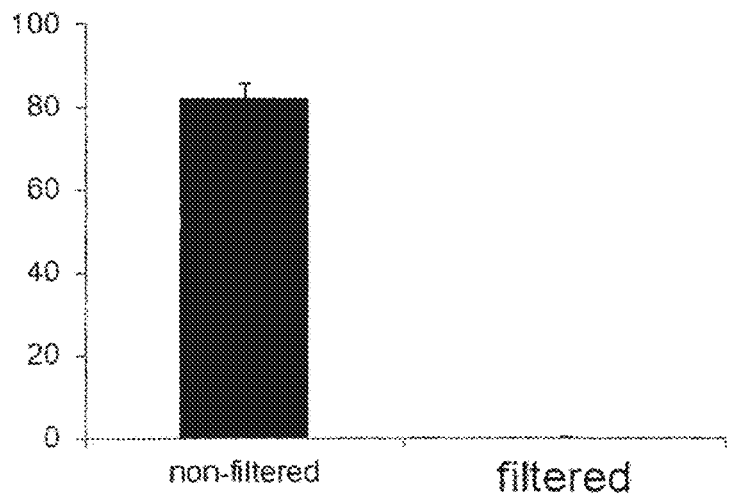
Figure 41:
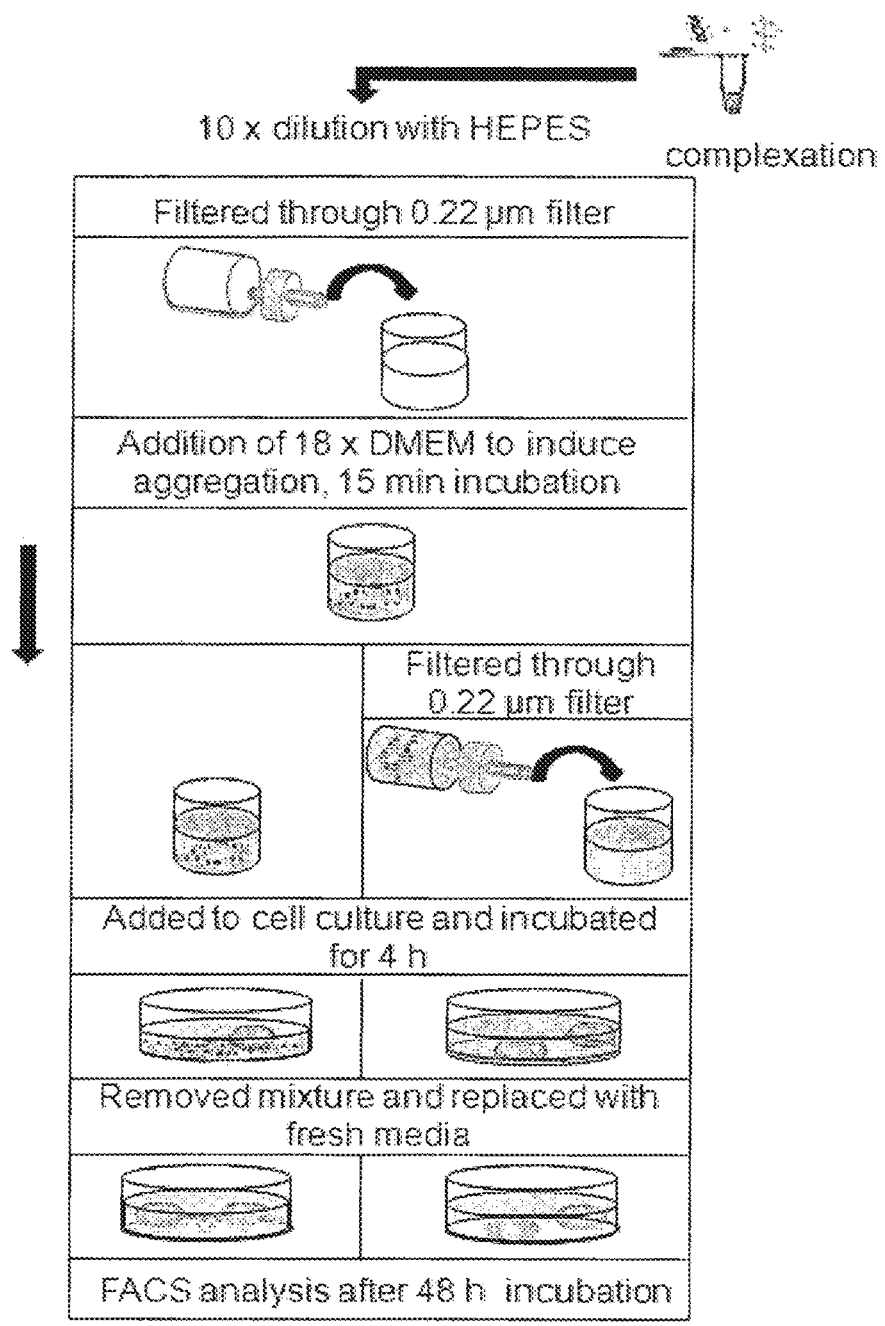

FIG. 41 shows a data that aggregated polyplexes were removed by 0.22 μM filter. LPEI/pDNA (N/P=20) pre-complexed in HEPES was filtered. After which, concentrated DMEM (18×) was added to the filtrate to a final concentration of 1×DMEM and incubated for 15 min. The mixture (filtered or non-filtered) was then added to plated Neuro2A cells and centrifuged. Cells were not transfected using filtrate (insert). Transfection efficiency was quantified by FACS 48 h later. The data shown were the mean±s.d., n=4. Furthermore, a schematic of the experimental design done is shown.

Figure 42:
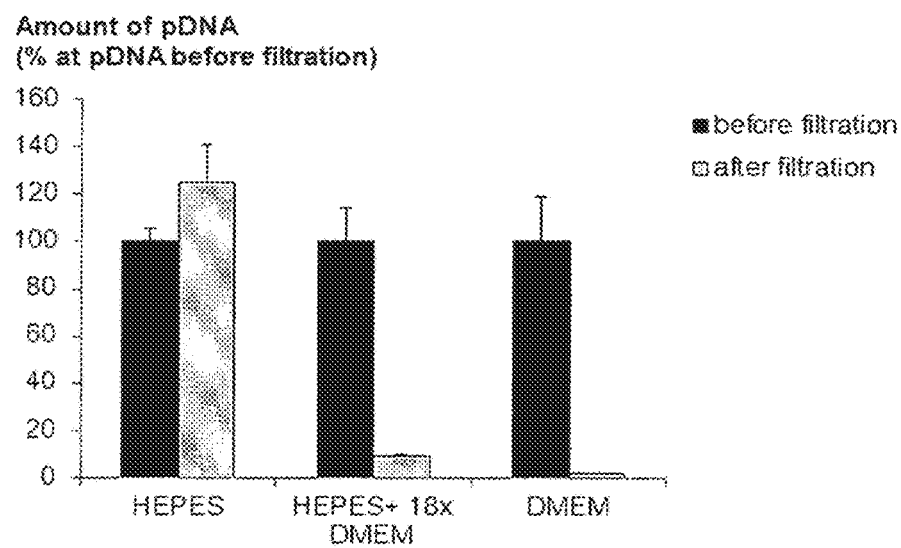

FIG. 42 shows data, in form of a histogram, indicating that LPEI/pDNA aggregated extensively DMEM. LPEI/pDNA (N/P=20) in 25 mM HEPES or DMEM and incubated for 15 min. Absolute copy number of pDNA, with or without filtration (HEPES or DMEM), and in HEPES that was added to 18×DMEM, with or without second step of filtration (HEPES+18×DMEM) were quantified by qPCR after treatment with pAA/urea lysis buffer. The data shown were the mean±s.e.m., n=3.

Figure 43:
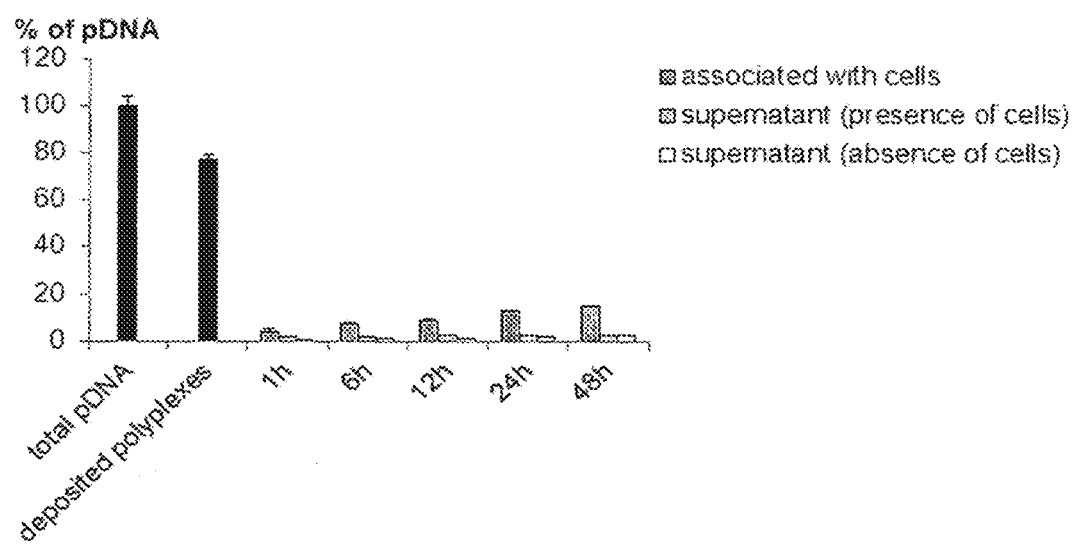

FIG. 43 shows a histogram, whereby the data indicates that the pDNA had not efficiently released from the surface bound aggregate. In the presence or absence of Neuro2A, transfection mixture of LPEI/pDNA (N/P=20) was centrifuged and replenished with complete media. At various time points, cells were harvested by trypsinization and supernatant collected. Samples were then treated with pAA/urea lysis buffer. The absolute copy number of pDNA was quantified by qPCR and normalized by control, N/P=0. The data shown were the mean±s.e.m., n=3.

Figure 44:
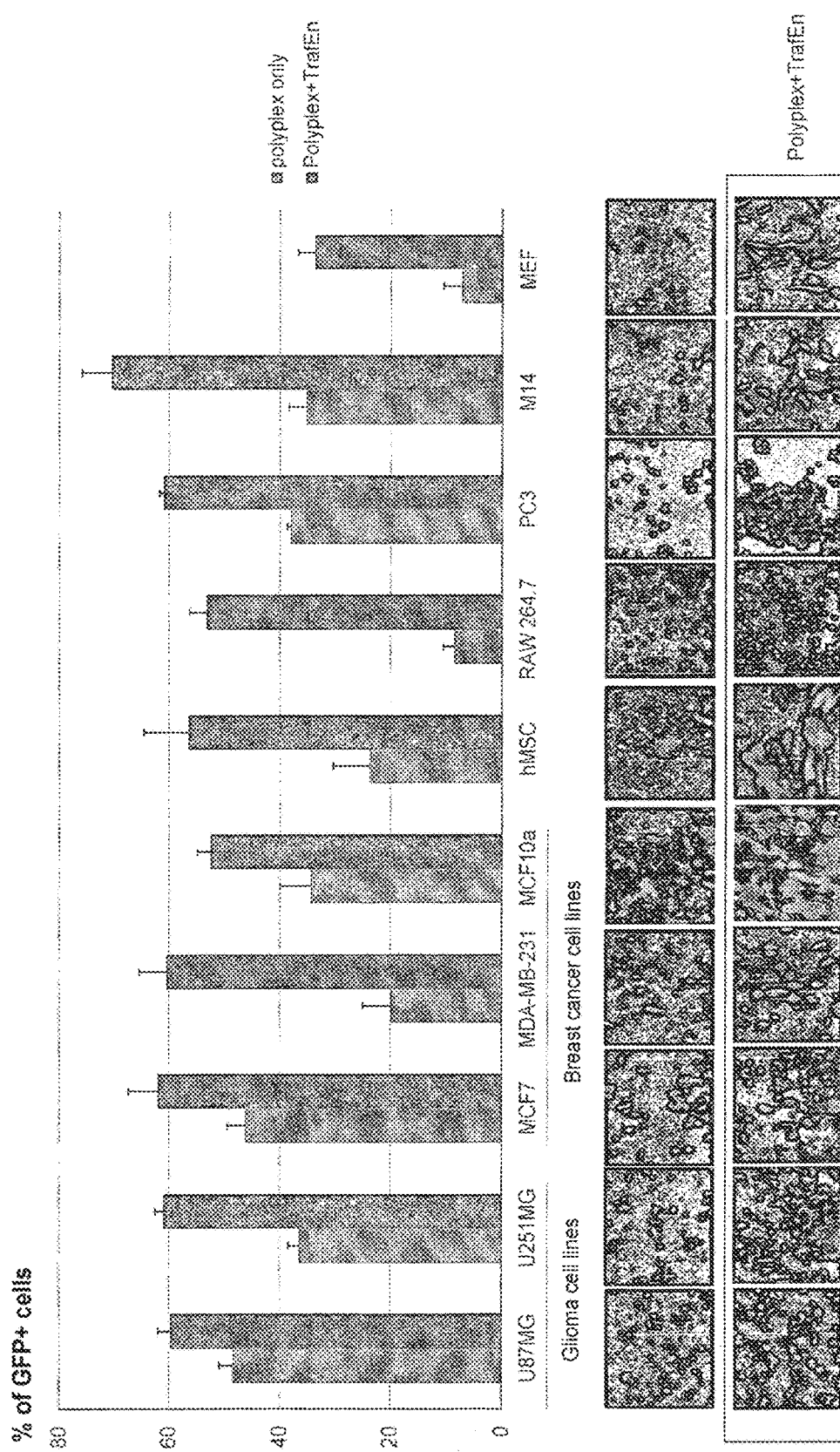

FIG. 44 demonstrates the effect of TrafEn™ in enhancing polymer-based transfection. This was tested on different cells and cell types, for example human glioma/breast cancer cell lines, human mesenchymal stem cells (hMSCs), murine Abelson leukemia virus induced tumour cells (RAW 264.7), human prostate cancer cells (PC3), human melanoma cells (M14) and mouse embryonic fibroblast cells (MEFs). Cells were transfected with PEIMAX/2 μg PMAXGFP (LONZA). After transfection, cells were incubated in culture media in the presence or absence of the TrafEn™ reagent. Forty-eight hours later, GFP+ cells were analysed by FACS analysis or semi-automated cell count using Image J. The histograms present percentage of GFP+ cells and error bar represent S.E.M of the biological triplicate and technical duplicates. Representative images are presented (Blue, Nucleus; Green, GFP).

Figure 45:
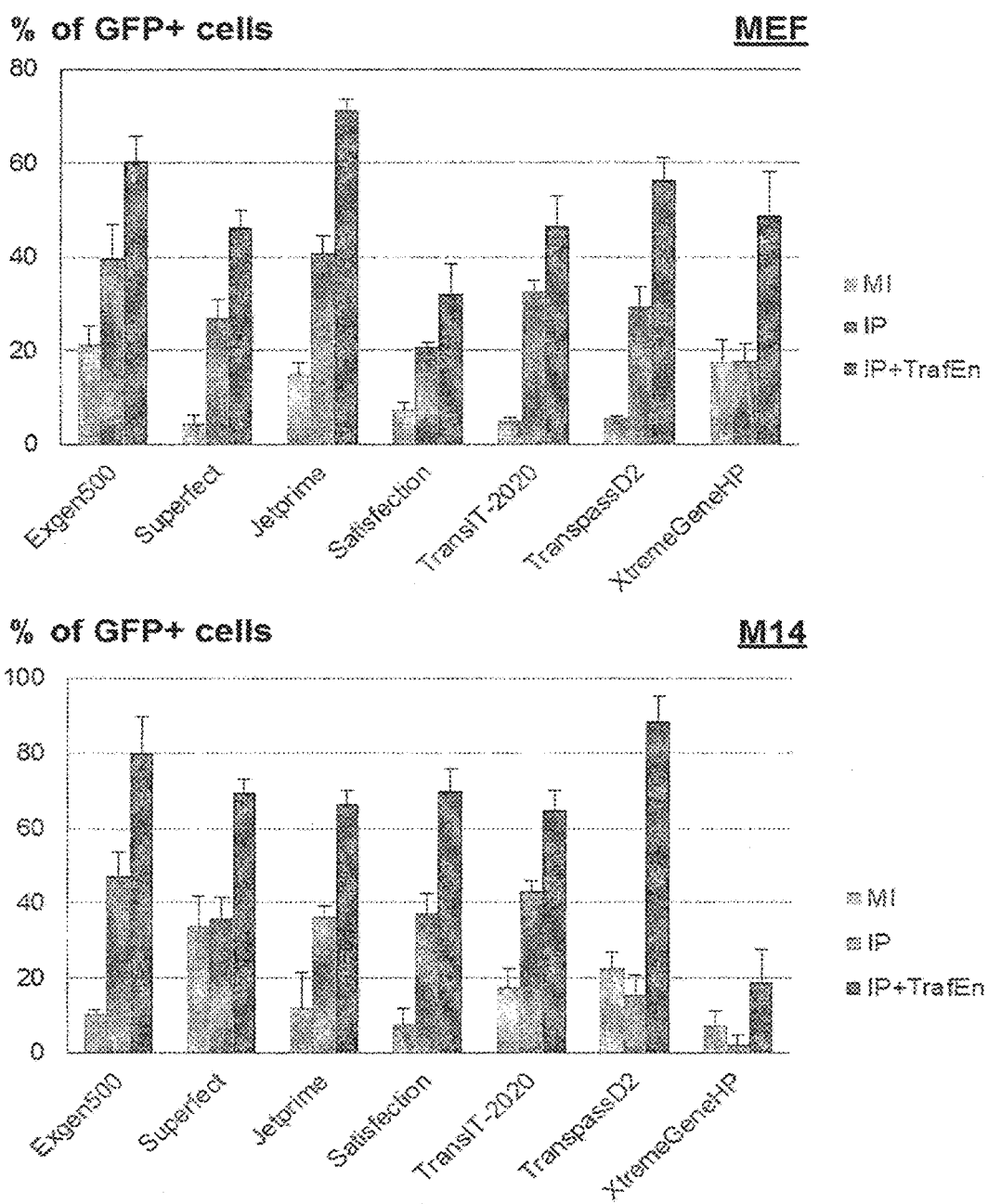

FIG. 45 shows the effect of TrafEn™ in the enhancement of polymer-based transfection. MEF and M14 cells were transfected with EV71-pIRES-eGFP expression vector complexed with various transfection reagents. Transfections were conducted using 2 protocols—MI and IP. MI refers to the manufacture's instruction. IP refers to an in-house protocol, which is the deposit mediated transfection described in the specification, for example in FIG. 39. IP+ TrafEn™ refers to the addition of TrafEn™ reagents in the culture media after transfection. The histograms here represent the percentage (%) of GFP+ cells for each procedure, each using a different transfection reagent.

Figure 46:
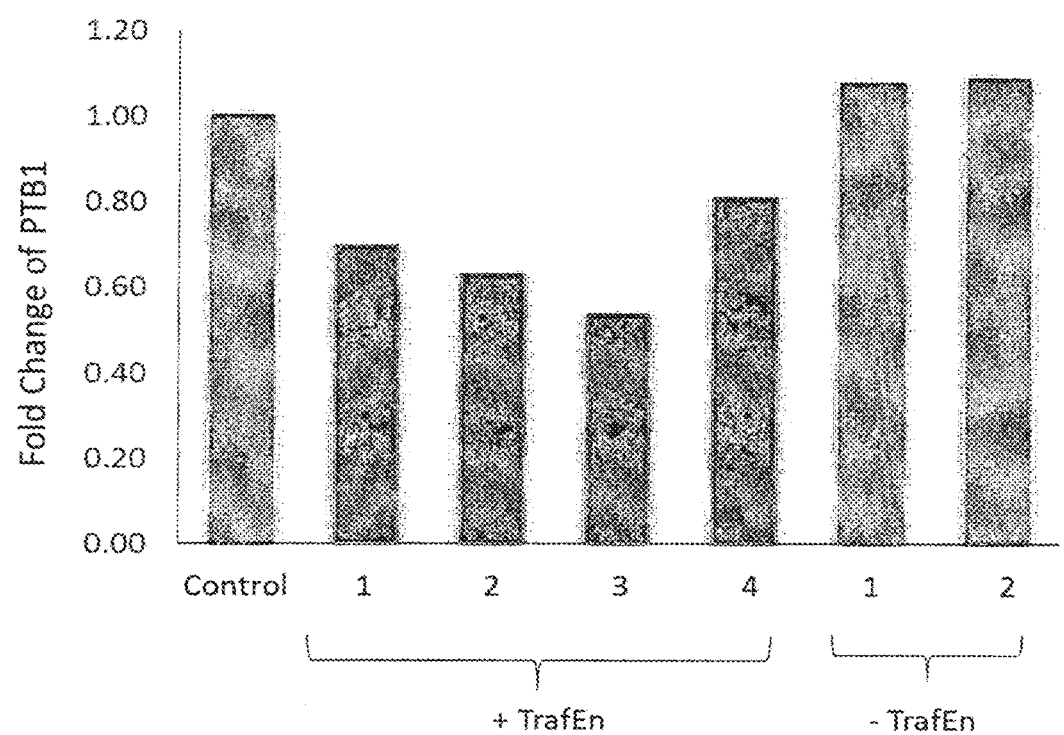

FIG. 46 shows histograms depicting the efficient knockdown of PTB1. HeLa cells were transfected with Scramble 30012 (Control), and PTB shRNA namely TR302218A 8865 (1), TR302218B 8866 (2), TR302218C 8867 (3), or TR302218D 8868 (4). The shRNAs were delivered by PEIMAX (N/P=10) in the presence or absence of TrafEn™ (DOPE/CHEMS+10 μM Tubastatin A). Three days post treatment cells were harvested for qPCR analysis. Graph present fold change of PTB1 to control after normalization to GAPDH.

Figure 47:
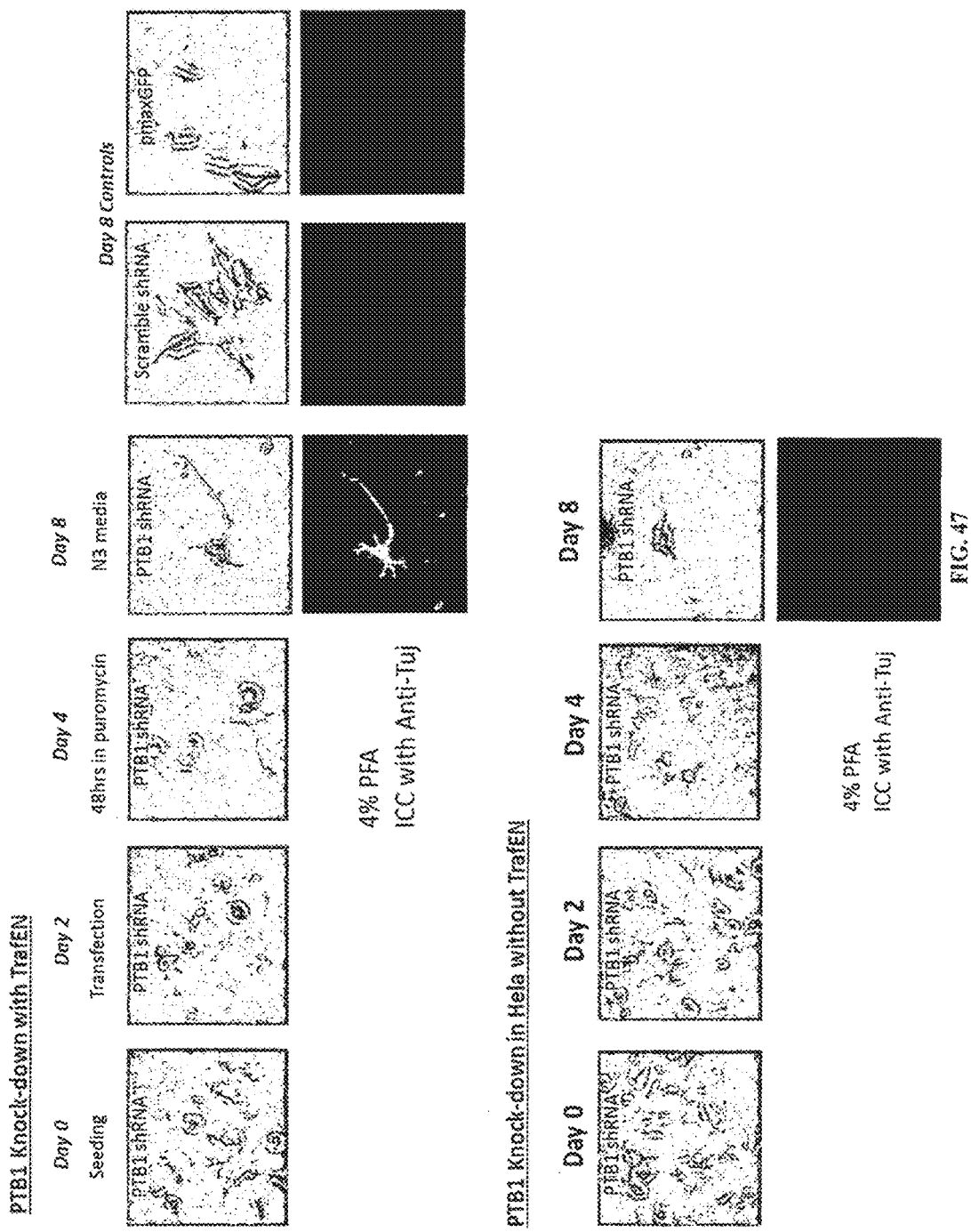

FIG. 47 shows micrographs depicting the efficient knockdown of PTB, resulting in rapid transdifferentiation. HeLa cells were transfected with Scramble 30012 (Control), PMAXGFP (Control), and TR302218C 8867. The shRNAs were delivered by PEIMAX (N/P=10) in the presence or absence of TrafEn™ (DOPE/CHEMS+10 μM Tubastatin A). Post transfection, cells were treated with Puromycin and culture in N3 media (Media for neuronal cells). Images were captured up to 8 days. Then, cells were fixed with 4% Formaldehyde and stained with Tuj antibody.

Figure 48:
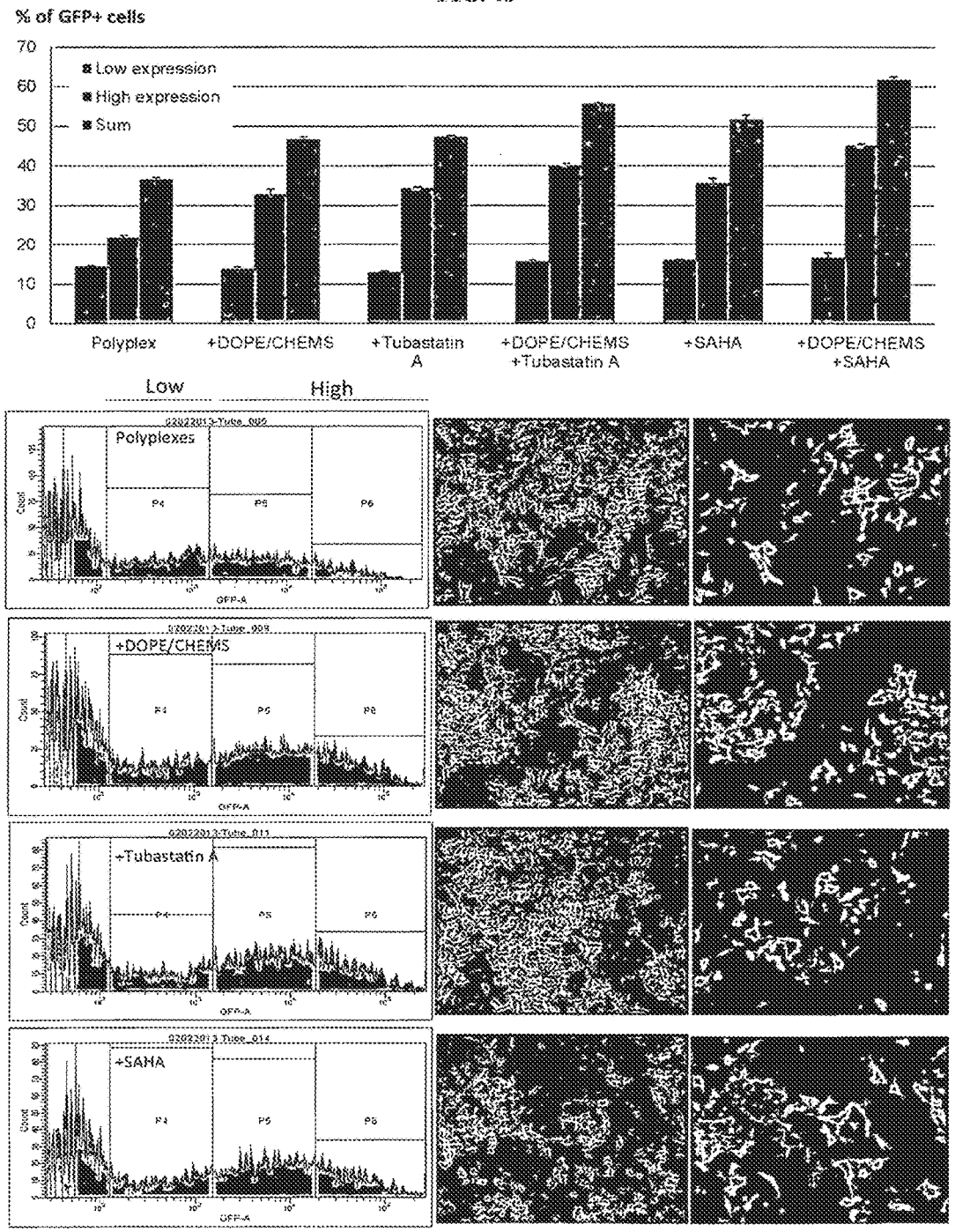
Figure 48:
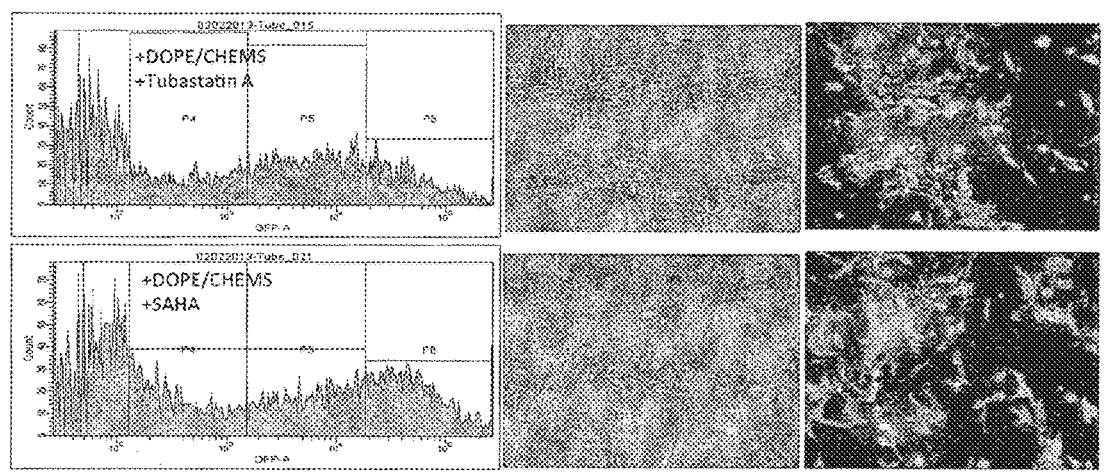

FIG. 48 shows graphs representing percentage (%) of cells showing low/high expression and the total % of GFP+ cells. Furthermore, representative images of the FACS analysis and transfected cells for each conditions are presented. Error bar represents the standard error mean (S.E.M.) of n=3. Statistical significance of transfection efficiencies between cells treated with DOPE/CHEMS+SAHA and DOPE/CHEMS or SAHA were obtained using two tailed student's t-test; *, $p<0.01$ the combinatorial effect of DOPE/CHEMS and SAHA or Tubastatin A in enhancing transfection. U251MG cells were transfected with PEIMAX complexed with 1.5 μg of PMAXGFP at N/P=10 in the absence or presence of DOPE/CHEMS and/or HDACi (10 μM Tubastatin A, 5 μM SAHA). After 24 h of transfection, culture media were replaced with fresh media with or without SAHA/Tubastatin A and further incubated for 48 h. Next, cells were harvested and GFP expressions were analysed by FACS analysis.

Figure 49:
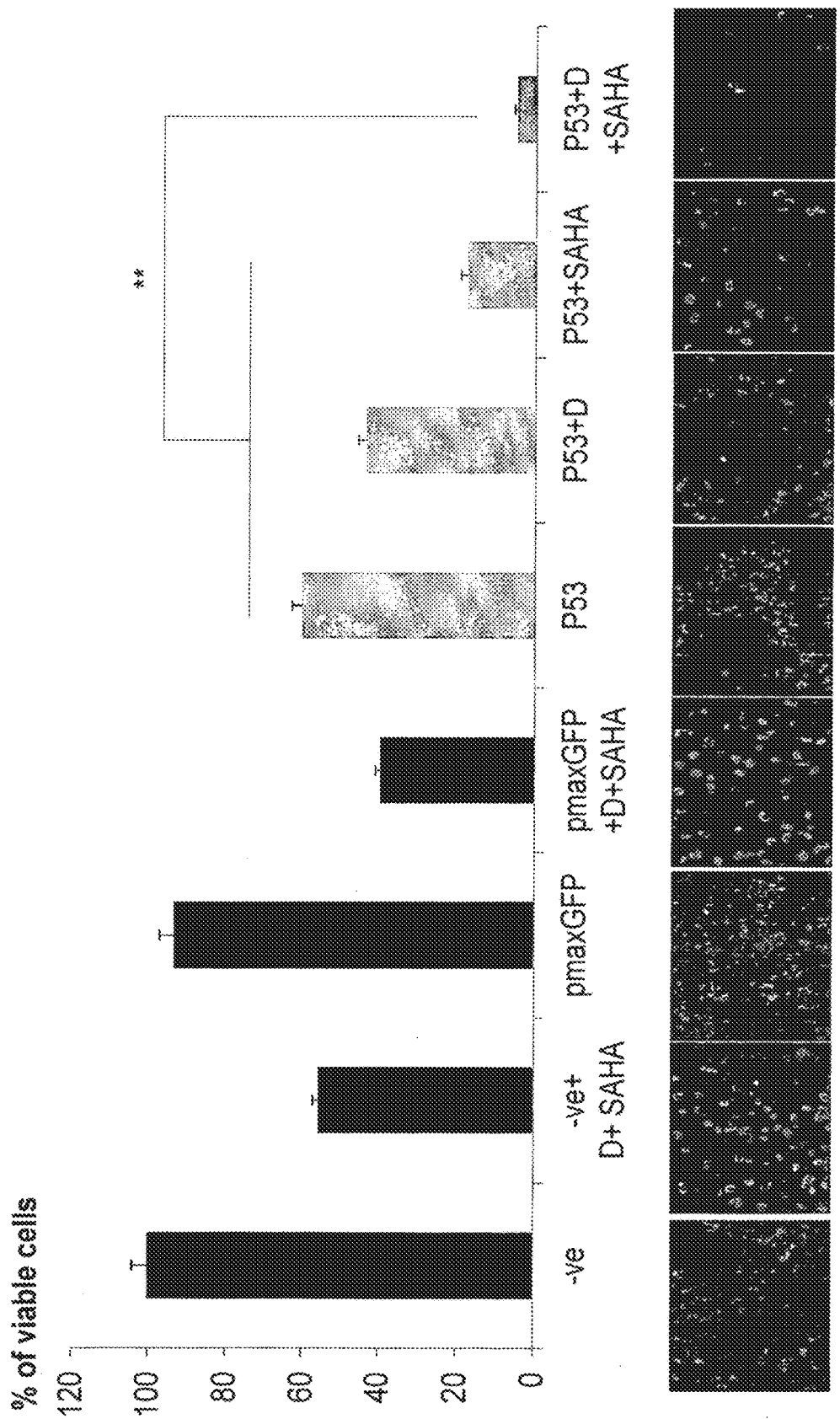

FIG. 49 shows fluorescent micrographs and histograms showing the synergistic effect of p53 and transfection enhancers. Cells were transfected with 1.5 μg of PMAXGFP or pEGFP-N1-p53 (p53). Transfection enhancers (DOPE/CHEMS [D] and 5 μM SAHA) were added to the culture media post transfection. After 24 h of transfection, culture media were replaced with fresh media with or without SAHA and further incubated for 48 h. Then, cells were fixed with 4% Formaldehyde and stained with Hoechst 33342. Fluorescent images were captured and nucleus number was counted with Image J. Percentage of viable cells represents % of cell to negative control (-ve). The lower panel contains representative images from each condition. Error bar represents the standard error mean (S.E.M.) of n=3. Unpaired, student t-test was performed to examine statistical significance between cells treated with P53, D and SAHA to cells treated with either one reagent. **, $p<0.001$.

Figure 50:
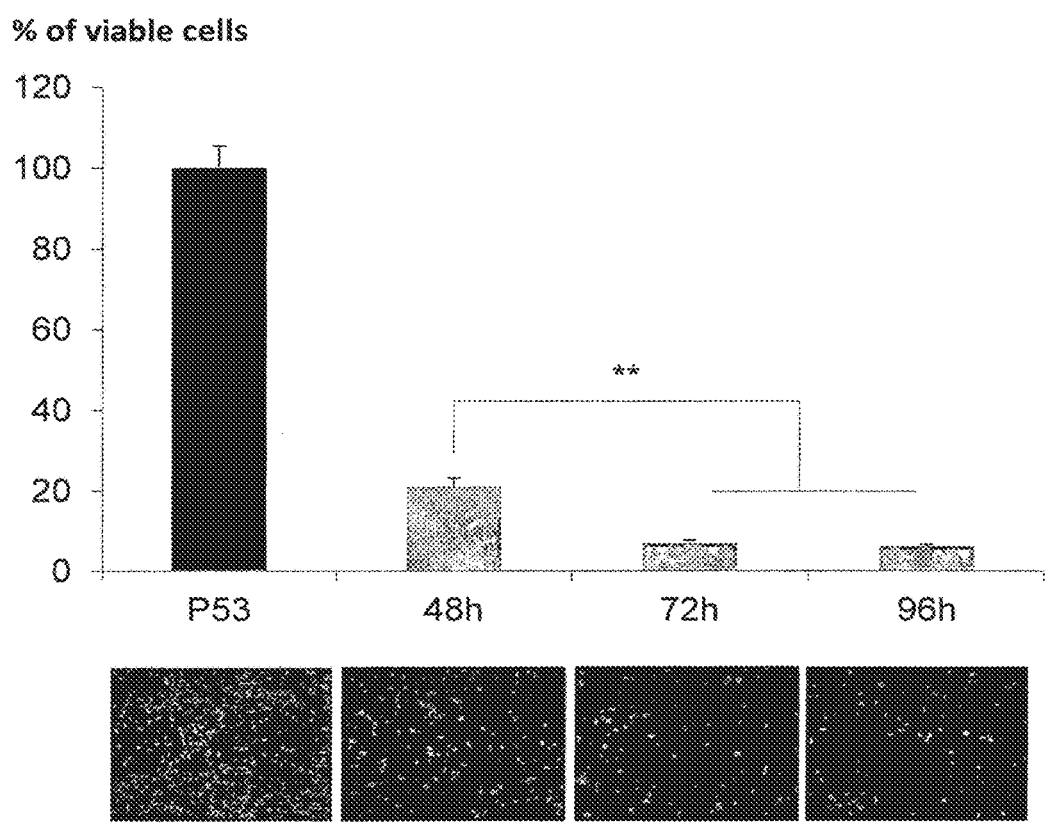

FIG. 50 shows a graph depicting the percentage (%) of viable cells, as well as fluorescent images of these cells, after prolonged incubation of U251MG cells with SAHA, showing that this did not increase cell death. Cells were transfected with pEGFP-N1-p53 (p53). Transfection enhancers (DOPE/CHEMS and 5 μM SAHA) were added to the culture media post transfection. The cells were further treated with SAHA for 48, 72 and 96 h. Next, cells were fixed with 4% Formaldehyde and stained with Hoechst 33342. Fluorescent images were captured and nucleus number was counted with Image J. Percentage of viable cells represents % of cell over cells transfected with p53 only. The lower panel contains representative images from each condition. Unpaired, student t-test was performed to examine statistical significance between cells treated with SAHA for 48 h and 72 or 96 h. **, $p<0.001$.

Figure 51:
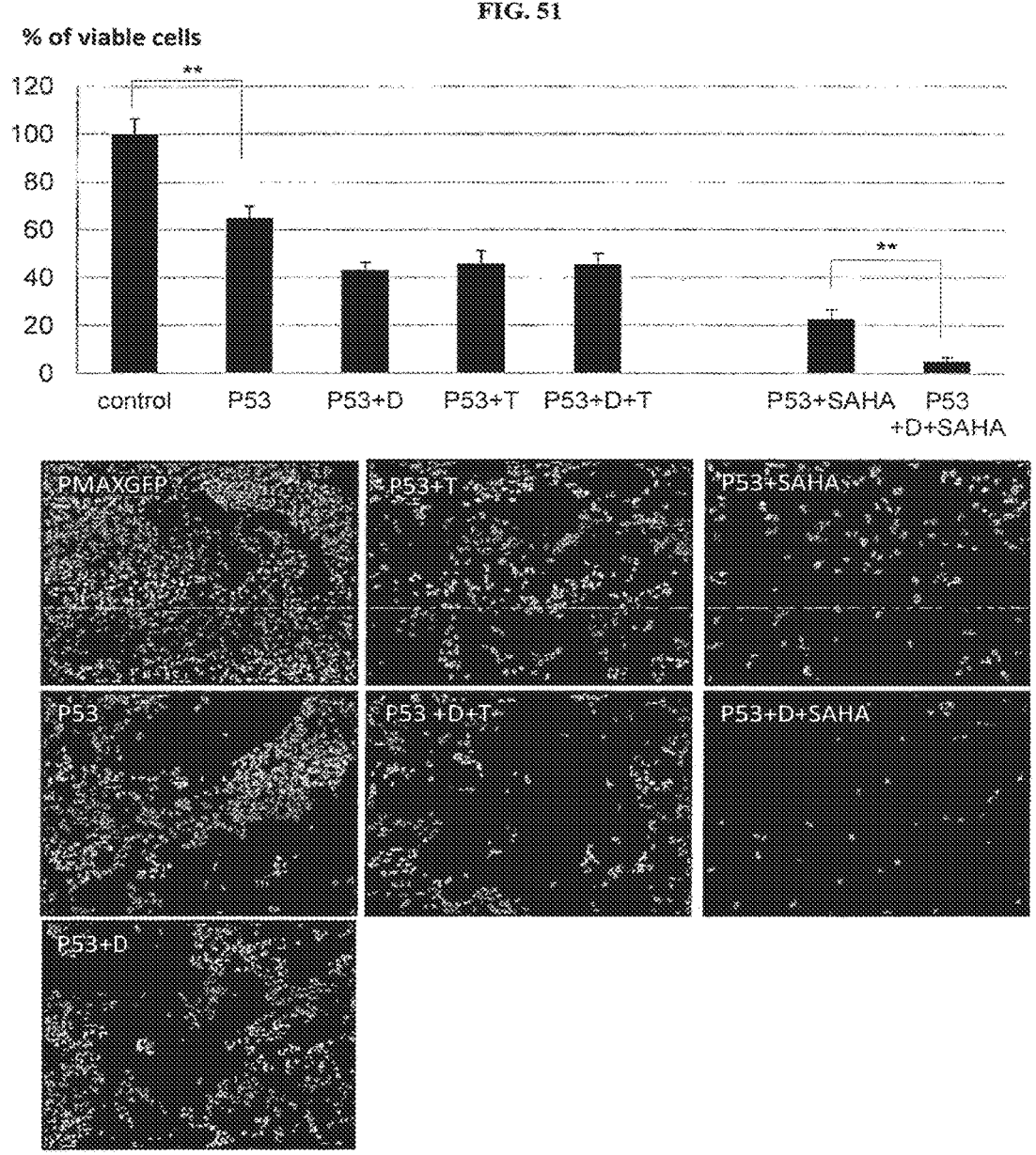

FIG. 51 shows a graph and accompanying fluorescent images, showing the synergistic cytotoxic effect of p53 with SAHA, but not Tubastatin A. Cells were transfected with PMAXGFP or pEGFP-N1-p53 (p53). Transfection enhancers (DOPE/CHEMS [D], 10 μM Tubastatin A [T] and 5 μM SAHA) were added to the culture media individually or combination post transfection. Culture media were replaced with fresh media with or without Tubastatin A or SAHA and further incubated for 48 h. Then, cells were fixed with 4% Formaldehyde and stained with Hoechst 33342. Fluorescent images were captured and nucleus number was counted with Image J. Percentage of viable cells represents % of cell to cells transfected with PMAXGFP. The lower panel consists of representative images from each condition. Error bar represents the standard error mean (S.E.M.) of n=3. Unpaired, student t-test was performed to examine statistical significance between 2 treatment conditions. **, $p<0.001$.

Figure 52:
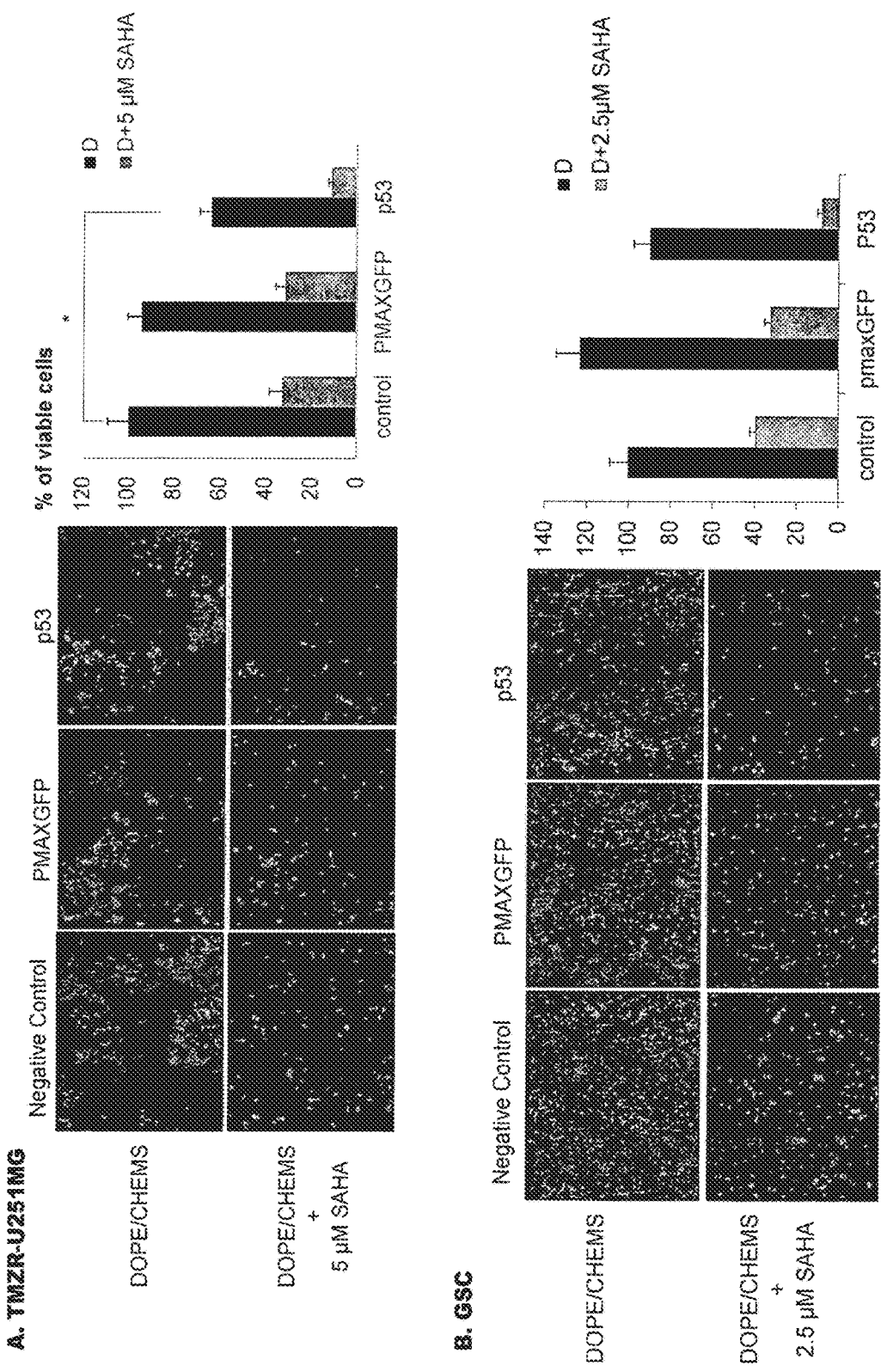

FIG. 52 shows fluorescent micrographs and histograms depicting the synergistic effect of p53 with SAHA in inducing significant cell death in both TMZR-U251MG and GSC. (A) TMZR-U251MG and (B) GSC cells were transfected with PMAXGFP and pEGFP-N1-p53 (p53) in the presence of DOPE/CHEMS [D] and SAHA individually or in combination. Twenty-two hours post transfection, the cell media was replaced with DMEM/10% FBS/40 μM TMZ for TMZR-U251MG and DMEM/serum replacement for GSC, with or without SAHA. Cells were further incubated for 48 h. Cells were fixed with 4% Formaldehyde and stained with Hoechst 33342. The images were analysed by Image J. Representative images are presented. Graphs present average of % of cells over control cells exposed to DOPE/CHEMS only (negative control+D). Error bar represents the standard error mean (S.E.M.) of n=3. Unpaired, student t-test was performed to examine statistical significance between control and p53 transfected cells. **, $p<0.001$.

Figure 53:
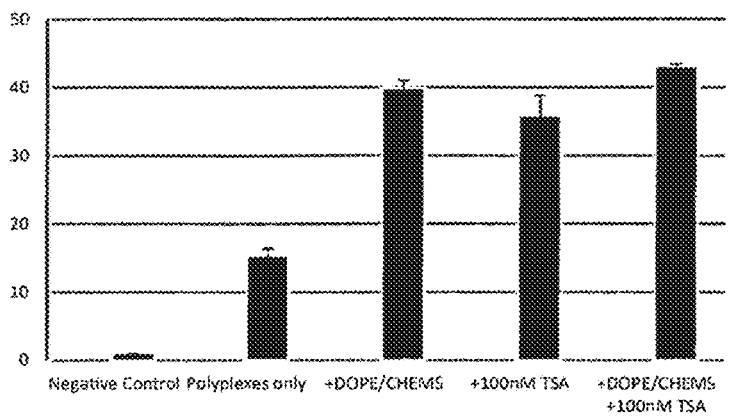
Figure 53:
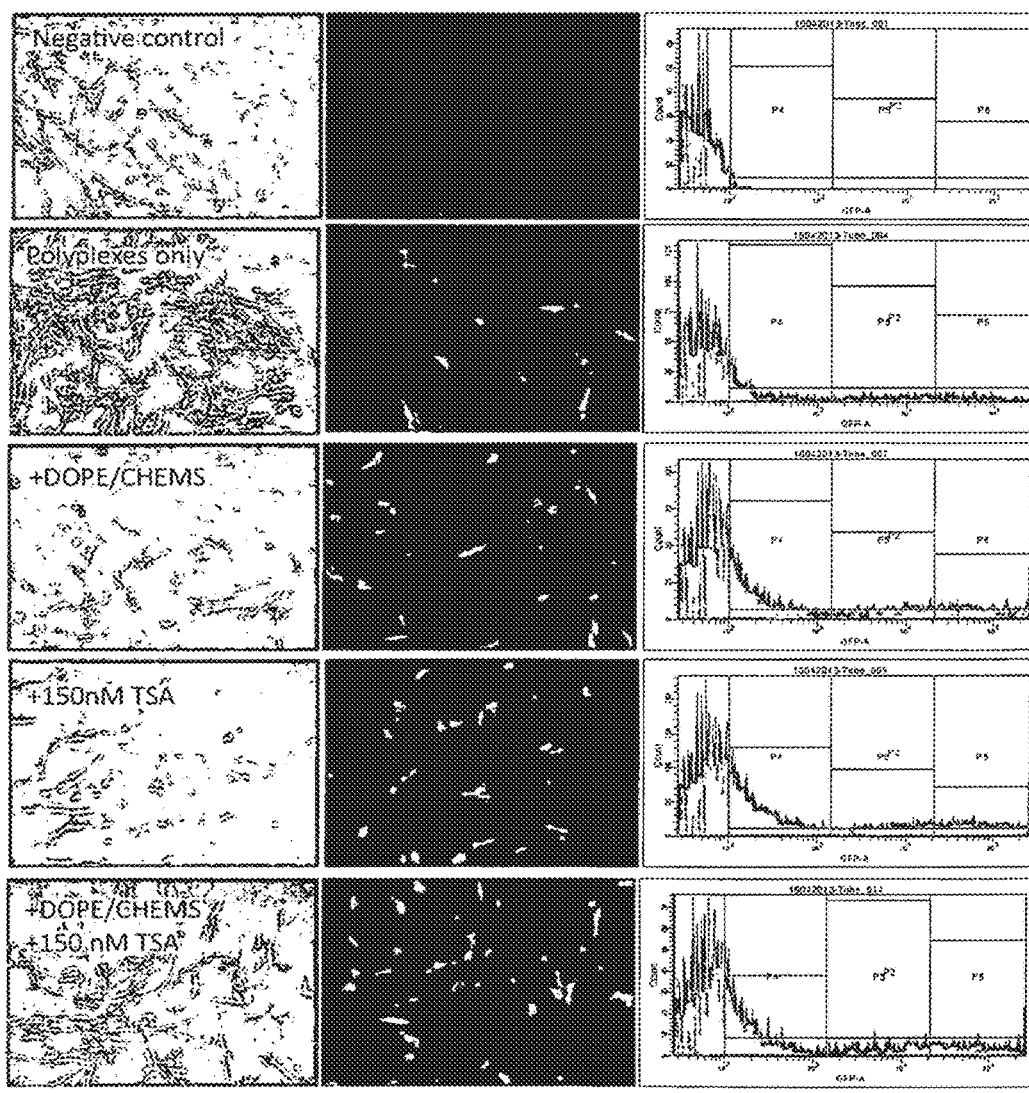

FIG. 53 shows fluorescent micrographs and histograms visualising the effect of DOPE/CHEMS and Trichostatin A (TSA) on the enhancement of transfection. The human fetal MSC cells were transfected with PEIMAX complexed with 1.5 μg of PMAXGFP at N/P=10 in the absence or presence of DOPE/CHEMS and/or HDACi (100 nM Trichostatin A). After 24 h of transfection, culture media were replaced with fresh media with or without Trichostatin A and further incubated for 48 h. Next, cells were harvested and GFP expressions were analysed by FACS analysis. Graph represents % of GFP+ cells. Error bar represents the standard error mean (S.E.M.) of n=3. Statistical significance of transfection efficiencies between cells exposed to polyplexes only and other conditions were obtained using two tailed student's t-test; *, p<0.01. Representative images of the transfected cells of each condition are presented.

Figure 54:
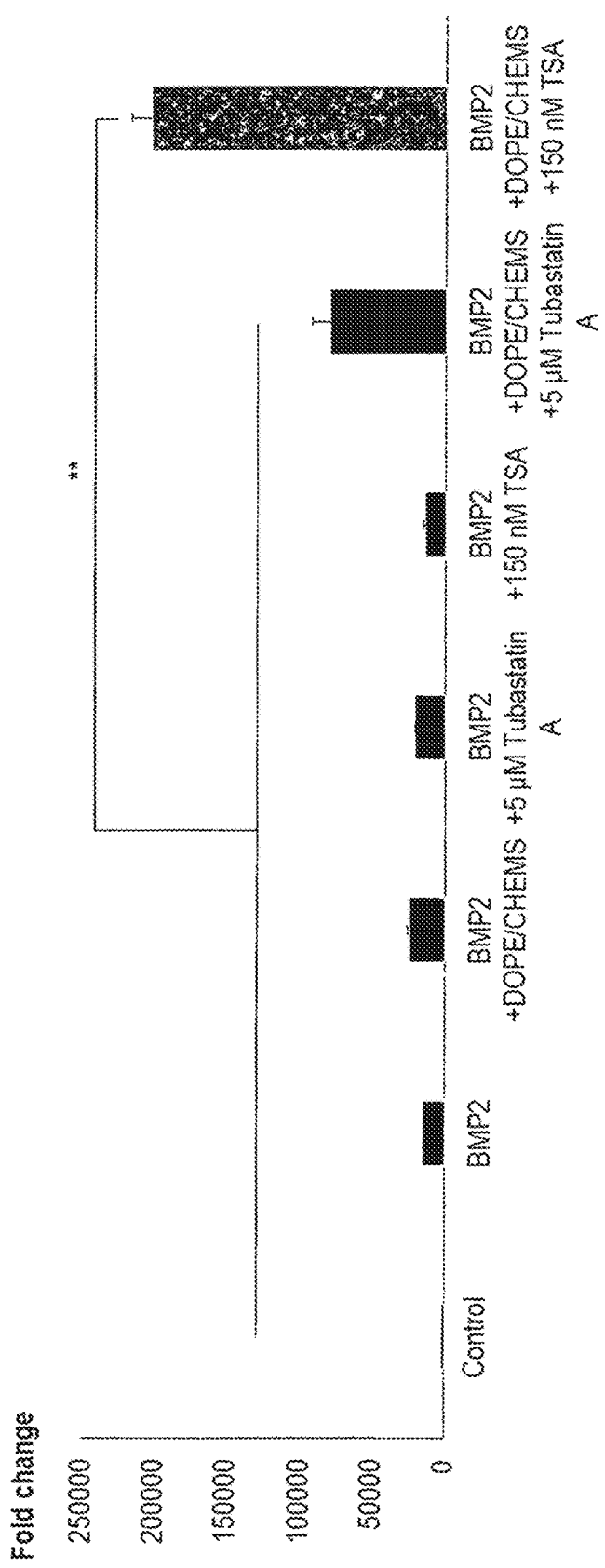

FIG. 54 depicts histograms depicting expression levels of BMP2 in human MSC under various treatment conditions. Human fetal MSC cells were transfected with PEIMAX complexed PMAXGFP (control) or PMAXGFP-BMP2 (human BMP2 cloned into PMAXGPF vector) at N/P=10 (BMP2). Post transfection, cells were treated with or without DOPE/CHEMS, 5 μM Tubastatin A, and 150 nM TSA in combination or individually. 24 hours post transfection, culture media was replaced with fresh media containing HDACi according. After 48 h of incubation, cells were trypsinized and total RNA were collected with RNeasy Mini Kit (Qiagen) to avoid DNA contamination. One microgram (μg) of the total RNA was reversed transcribed and the expression of BMP2 was measured using qPCR. The threshold cycles ($C_t$s) of BMP2 were normalized to the house-keeping gene GAPDH. Cells transfected with PEIMAX/PMAXGFP serves as a negative control (control). Graph presents fold change of BMP2 expression to the negative control. Error bar represents S.E.M of means (n=3). Unpaired, student t-test was used to test statistical significance between treatment conditions. *, p<0.01.

Figure 55:
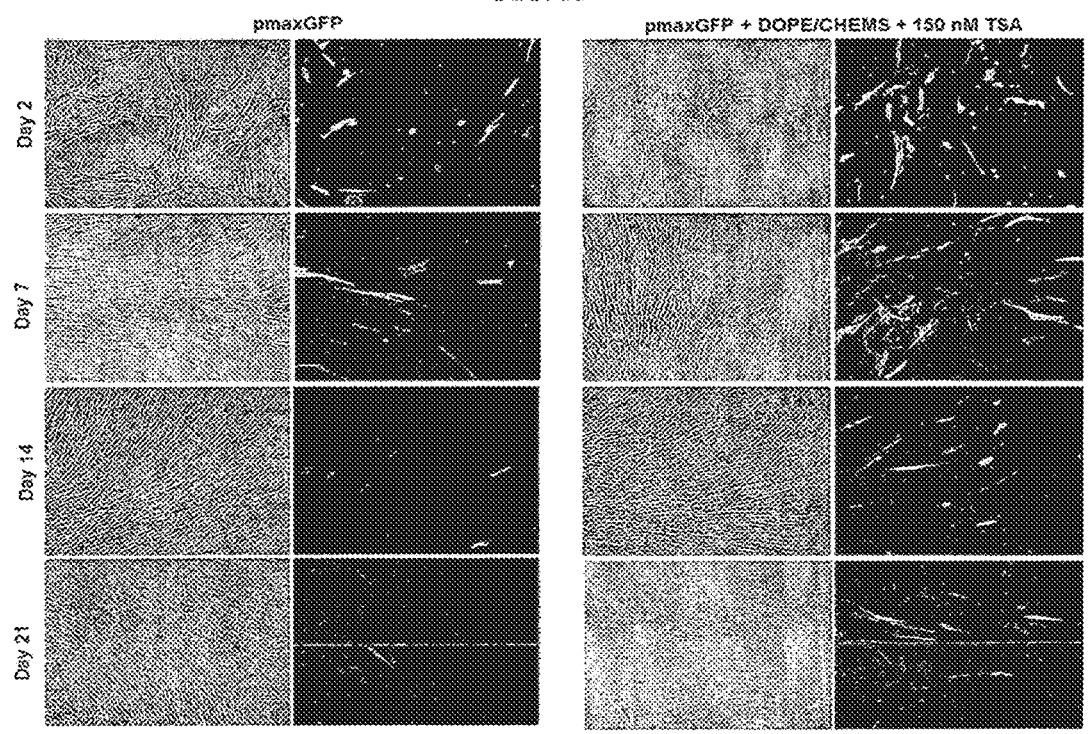

FIG. 55 shows bright field and fluorescent images of GFP Expression of in human MSC up to 21 days of incubation. Human fetal MSC cells were transfected with PEIMAX/PMAXGFP complex at N/P=10. Post transfection, the media was replaced with fresh culture media with or without DOPE/CHEMS and 150 nM TSA. Three days after transfection, media was replaced with fresh culture media. Bright field and fluorescent images were taken at Day 2, 7, 14 and 21 days post transfection. Representative imaged are presented.

Figure 56:
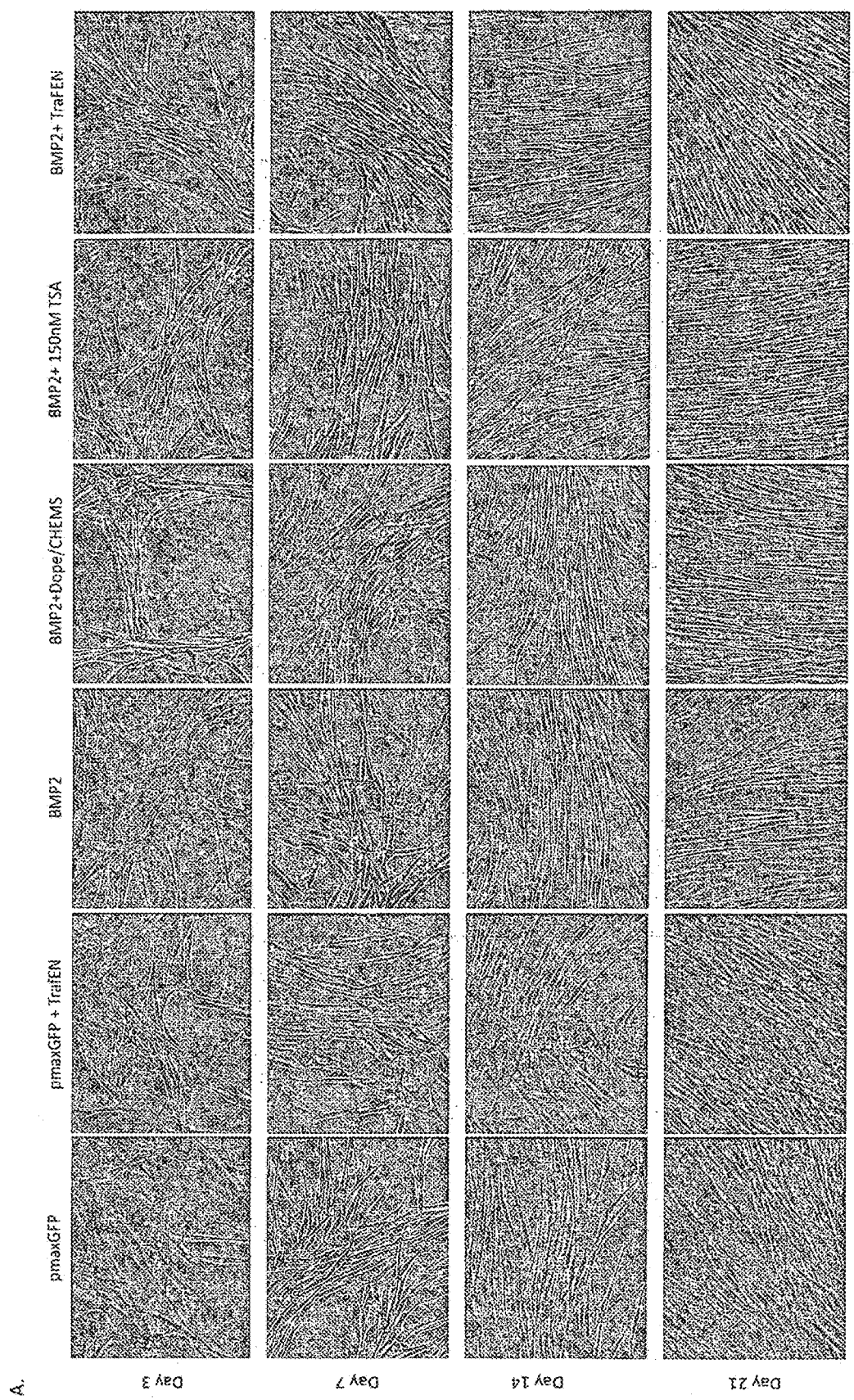
Figure 56:
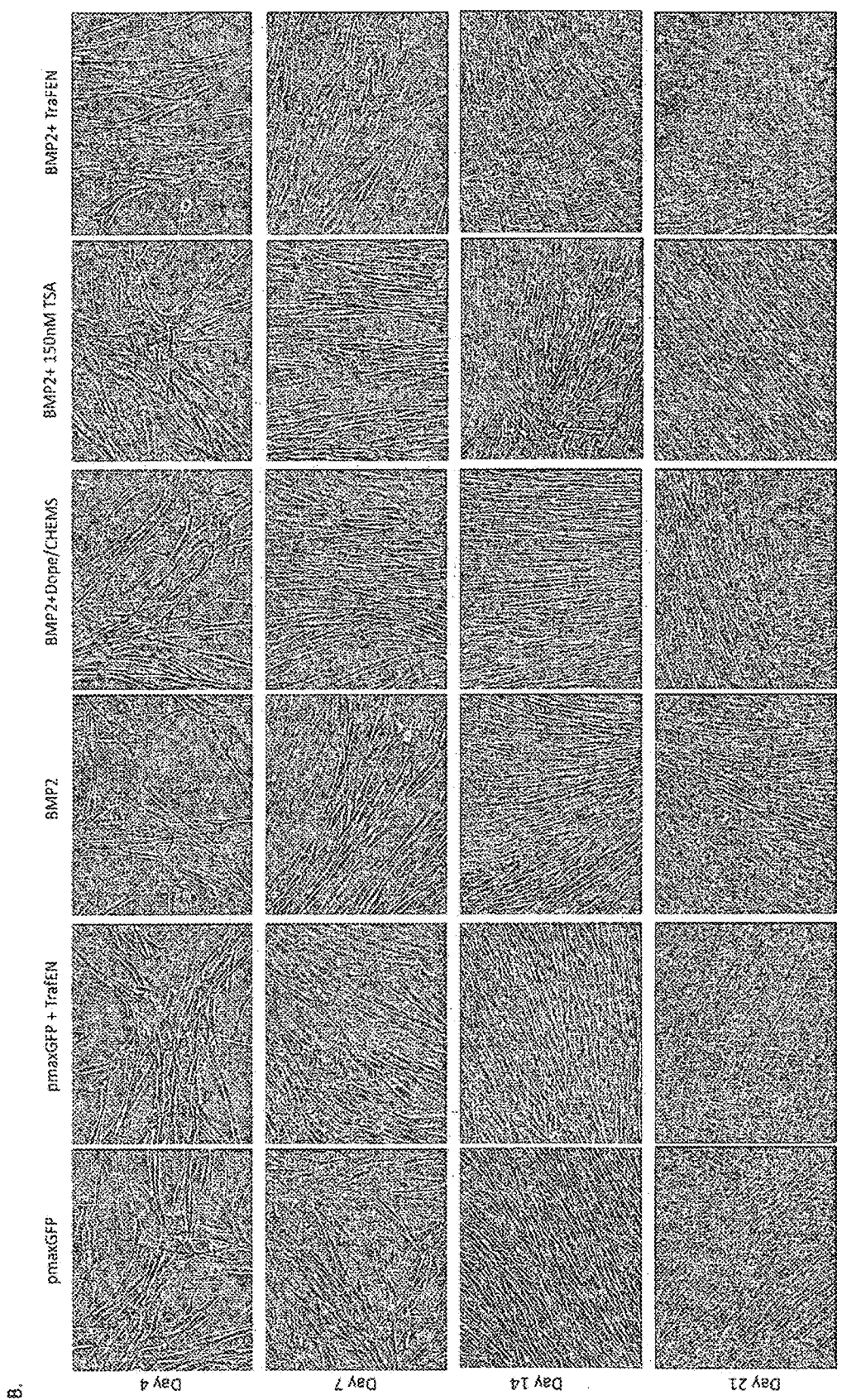

FIG. 56 shows bright field images of MSC cells from 3 up to 21 days post transfection. MSC cells were transfected with PEIMAX mediated delivery of PMAXGFP or PMAXGFP-BMP2. After transfection, cells were treated with DOPE/CHEMS and 150 nM TSA individually or in combination. 72 hours post transfection, culture media was replaced with (A) expansion media alpha-MEM/10% FBS or (B) osteogenic differentiation media (alpha-MEM supplemented with 10% FBS, 10 mM β-glycerophosphate, 10 nM dexamethasone, and 0.2 mM ascorbic acid. Cells were then further incubated and the respective media was replaced every 3 days.

Figure 57:
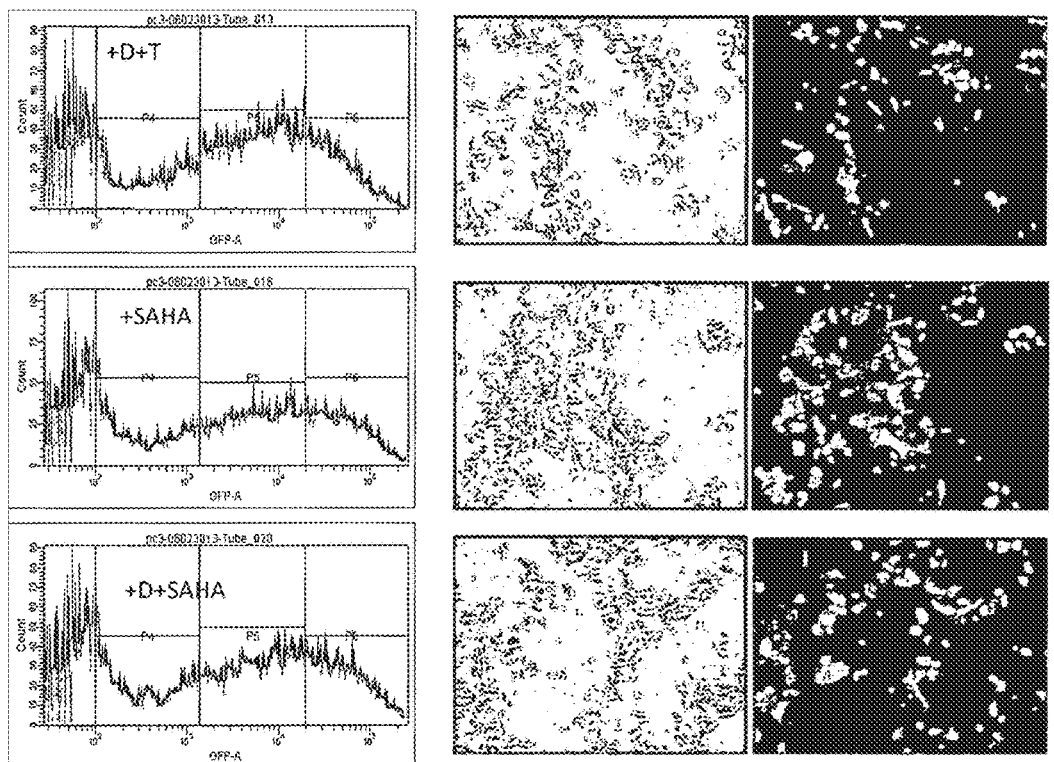

FIG. 57 shows micrograph images (bright field and fluorescent), as well as column graphs and FACS analysis graphs visualising the combinatorial effect of DOPE/CHEMS and SAHA or Tubastatin A in the enhancement of transfection. The PC3 cells were transfected with PEIMAX complexed with 1.5 μg of PMAXGFP at N/P=20 in the absence or presence of DOPE/CHEMS [D] and/or HDACi (20 μM Tubastatin A [T], 5 μM SAHA). After 24 h of transfection, culture media was replaced with fresh media with or without SAHA/Tubastatin A and further incubated for 48 h. Next, cells were harvested and GFP expression was analysed by FACS analysis. The column graph shows the percentage (%) of cells considered to be showing low/high expression of GFP and the total % of GFP+ cells. Representative images of the FACS analysis and transfected cells of each condition are presented. Error bar represents the standard error mean (S.E.M.) of n=3.

Figure 58:
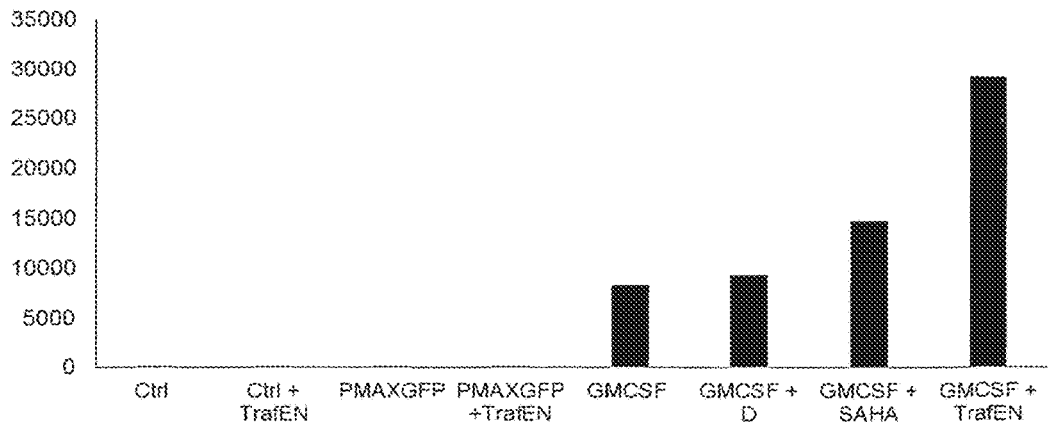

FIG. 58 shows histograms depicting the expression levels of GM-CSF in PC3 cells under various treatment conditions. Human PC3 cells were transfected with PEIMAX complexed PMAXGFP (control) or PMAXGFP-GM-CSF (human GM-CSF cloned into PMAXGPF vector, GMCSF) at N/P=20. Post transfection, cells were treated with or without DOPE/CHEMS [D] and 5 μm SAHA individually or in combination [TrafEn™]. 24 hours post transfection, culture media was replaced with fresh media containing HDACi accordingly. After 48 h of incubation, cells were trypsinized and the total RNA was collected individually using the RNeasy Mini Kit (Qiagen) to avoid DNA contamination. One microgram (μg) of total RNA was reverse-transcribed and the expression of GM-CSF was measured using qPCR. The threshold cycles ($C_t$s) of GM-CSF were normalized to the house-keeping gene GAPDH. Untransfected cells served as controls (Ctrl).

Figure 59:
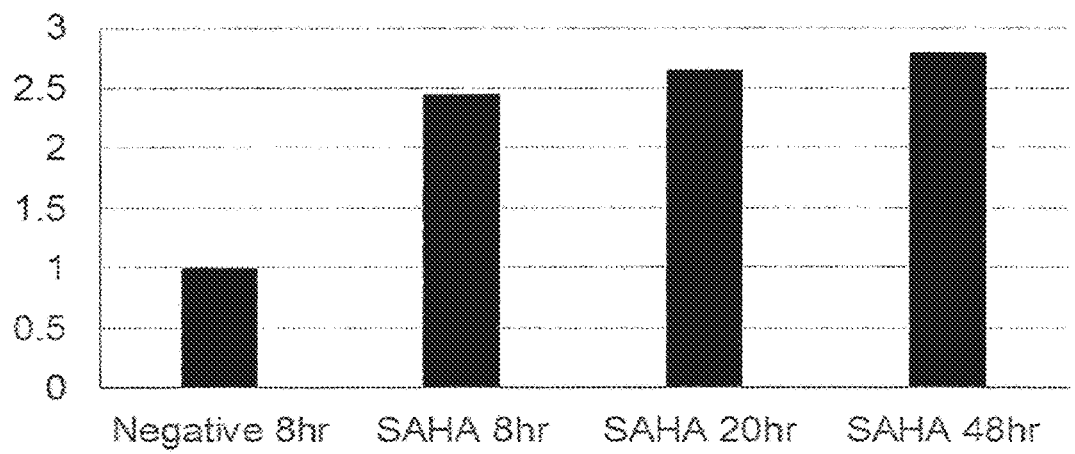
Figure 59:
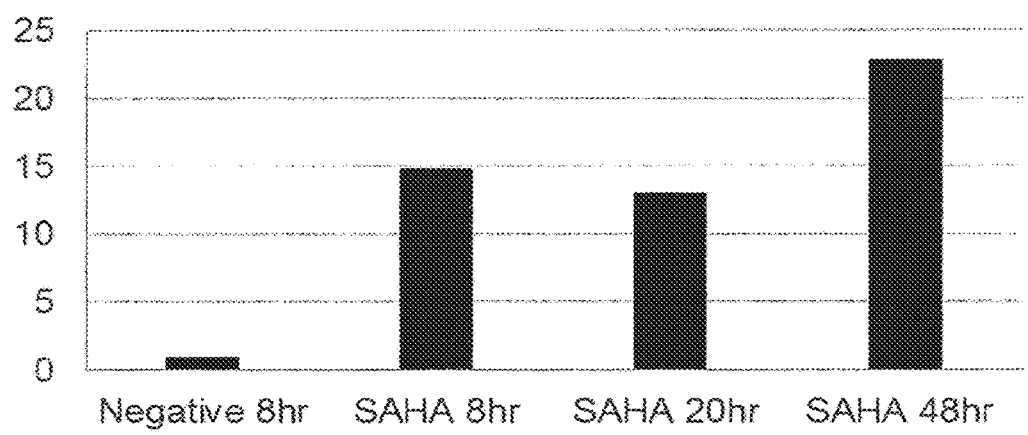

FIG. 59 shows histograms visualising that SAHA induced an up-regulation of MICA and NKG2D in PC3 cells. Human PC3 (prostate cancer) cells were treated with 5 μM SAHA for 8, 20 and 48 hours (hr). At the end of the incubation, the cells were collected and subjected to PCR analysis. Cells with no exposure to SAHA (Negative 8 hr) served as a control. The histogram here represented fold change to control after normalization with GAPDH.

Figure 60:
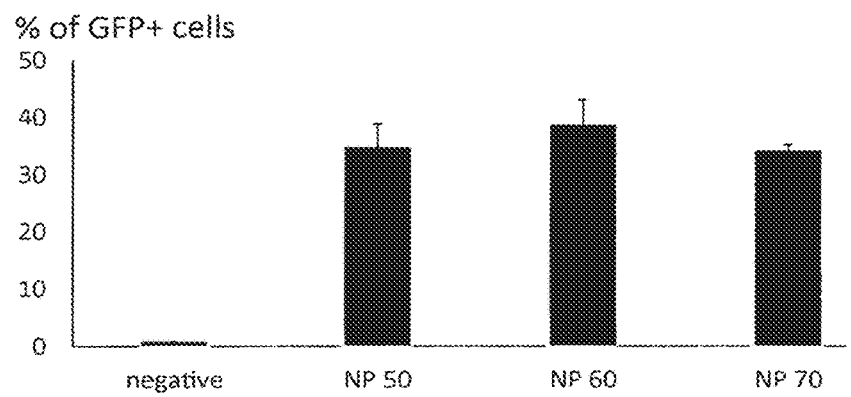
Figure 60:
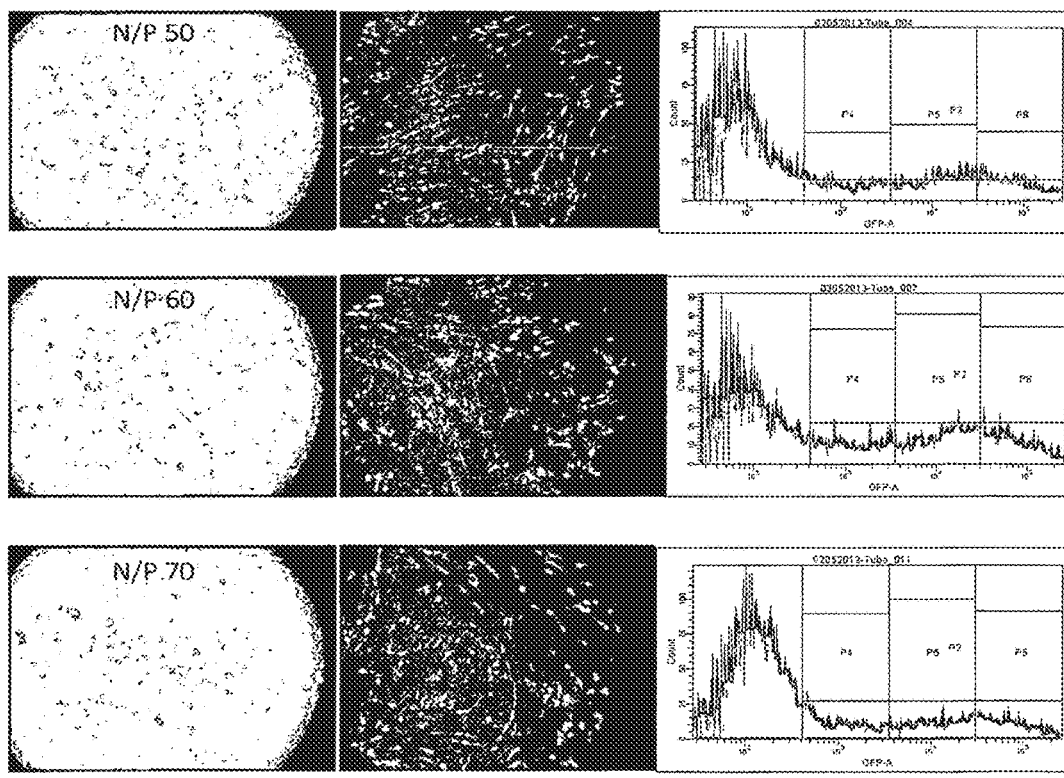

FIG. 60 show a high N/P ratio for transfection of HaF. Cells were transfected by PEIMAX/2 μg PMAXGFP at various N/P ratio using deposit mediated transfection protocol. Forty eight hour later, cells were trypsinized and analysed by flow cytometry. The percentage of cells expressed GFP is presented and error represents S.D. for n=3.

Figure 61:
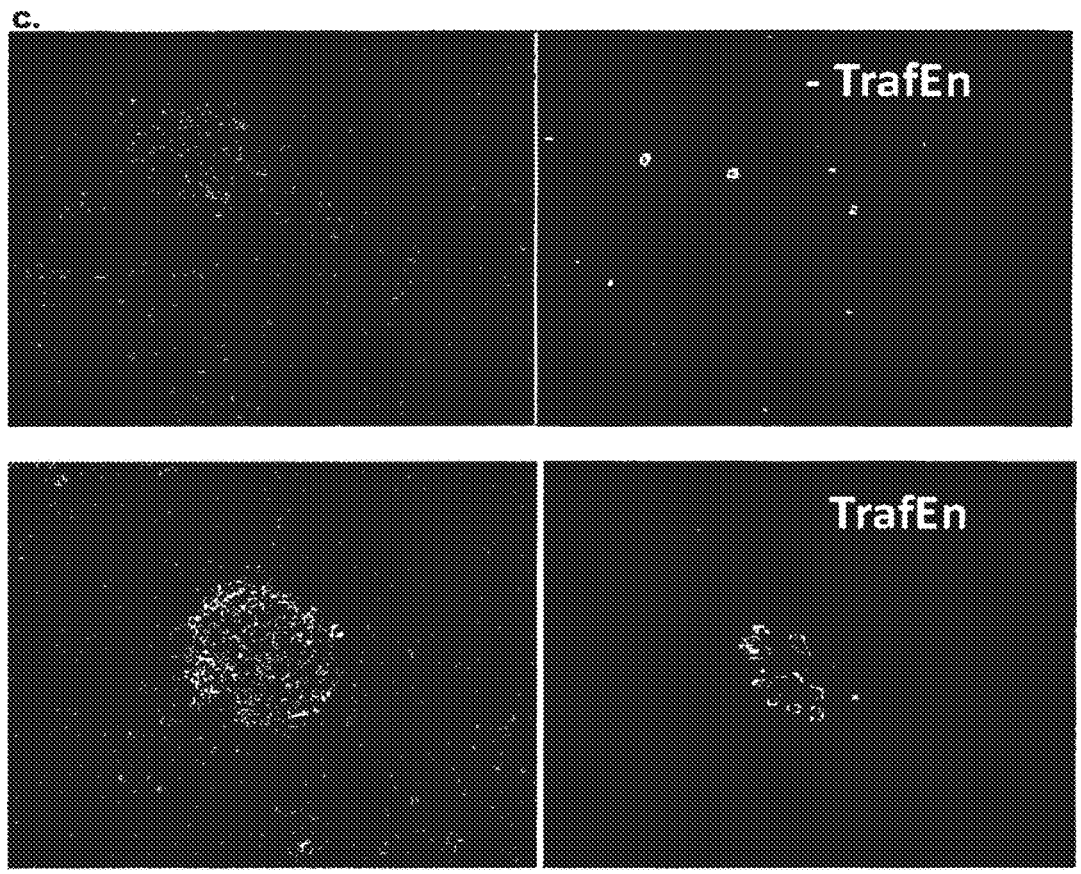

FIG. 61 show data showing that a high transfection resulted in efficient reprogramming of HaF. (A) Fibroblast cells were transfected with PEIMAX (N/P=50), Lipofectamine or Satisfection complexed to 2 μg PMAXGFP. After 48 h incubation, cells were trypsinized and analysed by flow cytometry analysis. Graph presents average % of GFP+ cells (n=3). Fluorescent images of the GFP+ cells are presented. (B, C) Fibroblast cells were transfected with PEIMAX complexed to 2 μg PMAXGFP or polycistronic OSKM (Addgene: 20328) at N/P=50. Next, the transfection mixture was replaced with culture media with or without TrafEn™ (DOPE/CHEMS+10 μM Tubastatin A). Two days later, the media were replaced with fresh culture media (10% FBS/DMEM). After 24 h incubation, total RNA were isolated with Qiagen RNAeasy kit and subjected to qPCR analysis. Graph presents expression of OSKM to control (cells transfected with PMAXGFP) after normalization to GAPDH. For a second set of experiment, cells were further incubated for 7 days. At the end of experiment, cells were fixed with 4% formaldehyde and stained with Oct4 antibody.

Figure 62:
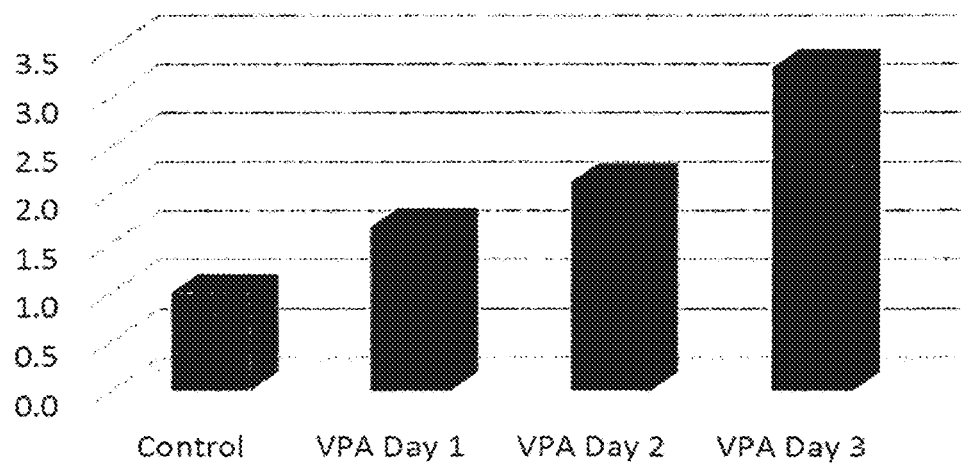
Figure 62:
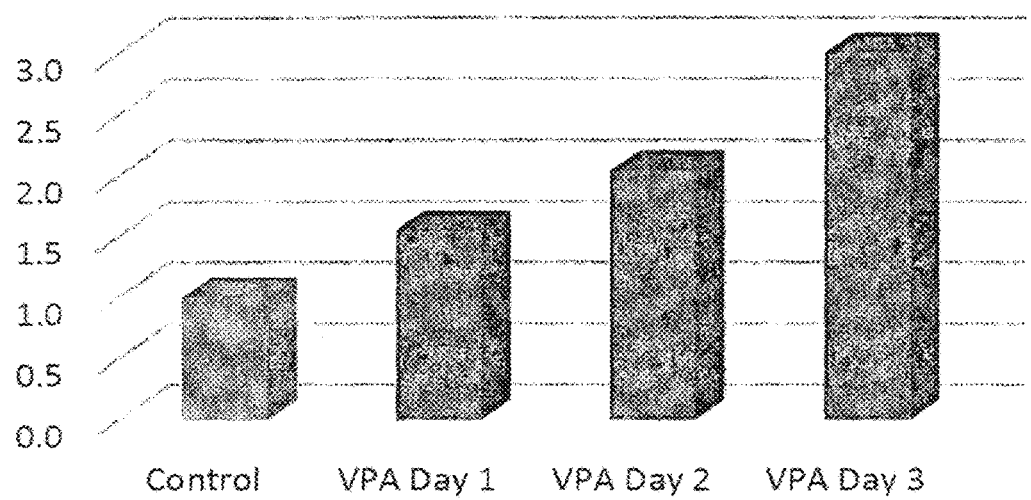

FIG. 62 shows histograms showing that VPA induced up-regulation of KLF4 and c-Myc in HaF. Fibroblast cells were treated with 1 mM VPA for up to 3 days. At the end of incubation, the cells were collected and subjected to PCR analysis. Cells with no exposure to VPA (3 days) serve as control. Graphs present fold change to control after normalization with GAPDH.

DEFINITION OF TERMS

As used herein, the term "nucleic acid" designates a molecule comprising one or more nucleotides, or an oligonucleotide, or a fragment thereof, including, without limitation, ribonucleic acid (RNA), messenger RNA (mRNA), DNA/RNA hybrids, non-natural or synthetic nucleic acids, short interfering RNA (siRNA), short hairpin RNA (shRNA), deoxyribonucleic acid (DNA), plasmid DNA (pDNA), antisense and sense oligonucleotides, nucleotides or combinations thereof. The nucleic acid may be single-stranded, or partially or completely double-stranded (duplex). Duplex nucleic acids may be homoduplex or heteroduplex. The term "ribonucleic acid" (RNA) refers to biomolecules that play an important role in the regulation, coding, decoding and expression of genes. Each ribonucleic acid consists of a nucleotide, either adenine (A), cytosine (C), guanine (G) or uracil (U), and a ribose sugar. A ribonucleic acid sequence comprises of a chain of these nucleic acids, resulting in a sugar-phosphate backbone. Concurrently, for the term "deoxyribonucleic acid" (DNA) refers to a biomolecule, consisting of either adenine (A), cytosine (C), guanine (G) or thymidine (T), attached to the sugar/phosphate to form the complete nucleotide.

As used herein, the term "isolated" means that a nucleotide sequence, for example a gene, primer, or oligonucleotide or other sequence is substantially or essentially free from other nucleic acids or other impurities.

As used herein, the term "amplicon", "amplified product" or "amplification product" refers to a product of an amplification reaction. An example of an amplicon is a nucleotide sequence produced as a result of PCR, real-time PCR, reverse transcription-PCR, competitive RT-PCR, ligase chain reaction (LCR), gap LCR, strand displacement amplification (SDA), nucleic acid sequence based amplification (NASBA), transcription-mediated amplification (TMA), rolling circle amplification (RCA) or the like.

The term "primer" is used herein to mean any single-stranded oligonucleotide sequence capable of being used as a primer in, for example, PCR or RCA technology. Thus, a "primer" according to the disclosure refers to a single-stranded oligonucleotide sequence that is capable of acting as a point of initiation for synthesis of a primer extension product that is substantially identical to the nucleic acid strand to be copied (for a forward primer) or substantially the reverse complement of the nucleic acid strand to be copied (for a reverse primer). A primer may be suitable for use in, for example, PCR technology. Single-stranded includes, for example, hairpin structures formed by single-stranded nucleotide sequences. The design of a primer, for example its length and specific sequence, depends on the nature of the target nucleotide sequence and on the conditions at which the primer is used, for example, temperature and ionic strength.

The primers may consist of the nucleotide sequences described herein, or may be 10, 15, 20, 25, 30, 35, 40, 45, 50, 75, 100 or more nucleotides which comprise or fall within the sequences described herein, provided they are suitable for specifically binding a target nucleic acid sequence, under stringent conditions. In one embodiment, the primer sequence is less than 35 nucleotides in length, for example the primer sequence is less than 34, 33, 32, 31, 30, 29, 28, 27, 26, 25, 24, 23, 22 21 20 19 18 17 16 15 14 13 12 11 or 10 nucleotides in length. Slight modifications of the primers or probes, in length or in sequence, can be carried out to maintain the specificity and sensitivity required under the given circumstances. In one embodiment of the present disclosure, probes and/or primers described herein may be extended in length by 1, 2, 3, 4 or 5 nucleotides or reduced in length by 1, 2, 3, 4 or 5 nucleotides, for example, in either direction. Primer sequences can be synthesized using any methods well known in the art.

As used herein, the terms "amplification" refers to an amplification reaction, for example an enzyme-mediated reaction used to amplify a specific target nucleotide sequence. By amplifying the target nucleotide sequence, the reaction produces many more copies of the target nucleotide sequence to produce an amplicon, amplified product or amplification product. One example of an amplification reaction is a "polymerase chain reaction' (PCR)". PCR is carried out with the aid of thermal cycler in a mixture containing a polymerase enzyme, a set of primers, for example a set of forward and reverse primers and any additional primers that may be required and four deoxynucleotide triphosphates—(dNTPs).

As used herein, the terms "therapeutic gene" and gene therapy refer to a therapy for genetic disorders, often similar to therapy for other disorders. Gene therapy may involve insertion of normal copies of a gene into the cells of people that is in vivo, with a specific genetic disorder. This therapy may involve replacing a deficient compound or blocking an overactive pathway. Gene therapy may also involve turning off genes. Genetic modification may also be used in ex vivo gene therapy. For example, human stem cells, immune cells or cancer cells, can be genetically modified for various applications. Cells are modified to induce differentiation, transdifferentiation or reprogramming. Also, cells may be modified to serve as vehicle to deliver therapeutic protein. For example, mesenchymal stem cells may be modified to overexpress BMP2.

The term "polyplex" refers to complexes of genetic material and a cationic species. The ratio of genetic material to cationic species (nucleic acid:polymer (N/P)) may be selected from the group consisting of from about 0 to about 1000, about 0 to about 900, about 0 to about 800, about 0 to about 700, about 0 to about 600, about 0 to about 500, about 0 to about 400, about 0 to about 300, about 0 to about 200, about 0 to about 100, about 0 to about 75, about 0 to about 50, about 0 to about 25, about 0 to about 20, about 0 to about 15, about 0 to about 10, and about 0 to about 5.

The term "anti-cancer drugs", also known as chemotherapeutic agents, refers to agents which used to treat cancers of the human body. There are different kinds of chemotherapeutics, which are defined into groups based on their method of action. Examples of the different groups of chemotherapeutics known in the art are as follows: alkylating antineoplastic agents, anti-metabolites, anti-microtubule agents, topoisomerase inhibitors and cytotoxic antibiotics. The agents can be administered to the patient intravenously, orally or intrathecally. Isolated limb perfusion is also a known delivery method for chemotherapeutics in certain cases.

The term "taxanes" refers to a class of are diterpenes produced by the plants of the genus *Taxus* (yews). Taxane based chemotherapeutic regimes are widely prescribed for cancer patients. Taxanes, which comprise of paclitaxel and docetaxel, promote microtubule stabilization, and disrupt transition from metaphase to anaphase. This blocks progression of cell division and prolonged activation of the mitotic checkpoint induces apoptosis or reversion to the G-phase, eventually causes cell death. Taxanes may be selected from a group consisting of cremophor EL® Taxoprexin®(Docosahexaenoic acid-paclitaxel), Xytotax™ (paclitaxel polyglumex), TOCOSOL® paclitaxel, BMS-184476, DJ-927, BMS-275183, RPR 109881A, Ortataxel, Genexol (co-polymer combination), LEP (liposomal-encapsulated paclitaxel) and taxol in vitamin E emulsion.

The term "epothilone" as used herein represents an emerging class of drugs for cancer treatment. The mechanism of action for epothilone class is similar to taxanes, which is the blockage of mitosis and induction of apoptosis. Nevertheless, Epithilones were shown to be more potent and milder side effects than taxanes. Additionally, their better water solubility characteristic enables the replacement of cremophors (solubilizing agents of paclitaxel) which was shown to affect cardiac function.

The term "histone deacetylase inhibitor" (HDACi) refers to a class of compounds that interfere with the function of histone deacetylase. HDACi is also known as epigenetic modifier. For example, by modifying the epigenetic pattern, SAHA and TSA have shown to exhibit various activities, such as immunomodulation and apoptosis. Although the clinical use of HDACi is widely associated with anti-cancer treatment, HDACi has also been investigated as therapeutic intervention for neurodegenerative disease, an anti-inflammatory and for the protection of heart muscle. More recently, HDACi has been demonstrated to promote self-renewal and enhance differentiation of stem cells, as well as increasing reprogramming efficiency of somatic cells. HDACs are also known to be involved in the maintenance and function of chromatin via regulation of acetylation state of histone. Advantageously, given such global effects on histone modulation, HDACi influences a broad repertoire of physiological processes, including transcription of genes involved in proliferation, differentiation, survival and DNA repair.

The term "TrafEn™" stands for trafficking enhancer and relates to two agents directing the genetic material or complex containing genetic material to a productive pathway for efficient transfection. In particular, TrafEn™ relates to transfecting a cell using comprising a first agent capable of directing the genetic material away from the acidic compartments and a second agent capable of stabilizing the microtubule or a network thereof. The application of TrafEn™ may be extended further to chemosensitize cells by rationally designing the composition to achieve a specific therapeutic effect. The first agent, as defined above, may also be termed "chemoRe-router".

A "subject" or an "individual" is a living multi-cellular vertebrate organism. In the context of this disclosure, the subject can be an experimental subject, such as a non-human animal, e.g., a mouse, a cotton rat, or a non-human primate. Alternatively, the subject can be a human subject.

The terms "biological material" or "biological sample" as used herein refers to any material or sample, which includes an analyte as defined herein. Such samples may, for example, include samples derived from or comprising stool, whole blood, serum, plasma, bone marrow, tears, saliva, nasal fluid, sputum, ear fluid, genital fluid, breast fluid, milk, colostrum, placental fluid, amniotic fluid, perspiration, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, e.g. from all suitable organs, e.g. the lung, the muscle, brain, liver, skin, pancreas, stomach, etc., a nucleated cell sample, a fluid associated with a mucosal surface, hair, or skin.

The terms "treatment", "therapeutic intervention" and "therapy" may be used interchangeably herein (unless the context indicates otherwise) and these terms refer to both therapeutic treatment and prophylactic or preventative measures, wherein the aim is to try and prevent or slow down (lessen) the targeted pathologic condition or disorder. In tumor treatment, the treatment may directly decrease the pathology of tumor cells, or render the tumor cells more susceptible to treatment by other therapeutic agents, e.g., radiation and/or chemotherapy. The aim or result of tumor treatment may include, for example, one or more of the following: (1) inhibition (i.e., reduction, slowing down or complete stopping) of tumor growth; (2) reduction or elimination of symptoms or tumor cells; (3) reduction in tumor size; (4) inhibition of tumor cell infiltration into adjacent peripheral organs and/or tissues; (5) inhibition of metastasis; (6) enhancement of anti-tumor immune response, which may, but does not have to, result in tumor regression or rejection; (7) increased survival time; and (8) decreased mortality at a given point of time following treatment. Treatment may entail treatment with a single agent or with a combination (more than two) of agents. An "agent" is used herein broadly to refer to, for example, a drug/compound or other means for treatment e.g. radiation treatment or surgery. Examples of treatment include surgical intervention, liver transplantation, immunotherapy, chemotherapy with a given drug or drug combination, radiation therapy, neo-adjuvant treatment, diet, vitamin therapy, hormone therapies, gene therapy, cell therapy, antibody therapy etc. The term "treatment" also includes experimental treatment e.g. during drug screening or clinical trials.

Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

DETAILED DESCRIPTION OF THE PRESENT INVENTION

Before the present inventions are described, it is to be understood that this invention is not limited to particular embodiments described, as such may vary. It is also to be understood that the terminology used herein is for purposes of describing particular embodiments only, and is not intended to be limiting, since the scope of the present invention will be limited only in the appended claims.

Attaining high transfection efficiencies when delivering genetic material, e.g. plasmid DNA and shRNA offers the potential for the treatment of a myriad of devastating disorders including, but not limited to, cancers, neurodegenerative diseases and inflammatory disease, for which there are currently few treatment options. Presently, low transfection and delivery efficiencies limit the application of drug-gene therapeutics. The development of galenics and methods for using this technology to enhance gene delivery ex vivo and in vivo represent an unmet need in this industry.

Advantageously, the present disclosure provides a unique composition of biocompatible reagents (TrafEn™), designed to drastically enhance the gene delivery and simultaneously chemosensitize the many types of hard-to-infect cells. The drug-gene combination described herein relates to a strategy, whereby a class of microtubule targeting chemosensitizers and a chemoRe-router increase the delivery of a therapeutic gene. The synergistic effect of TrafEn™ and the therapeutic gene are thought to result in a superior therapeutic effect. The formulation of chemosensitizers, as described further in the examples below, may contain an optimized mix of fusogenic molecules that specifically redirect carrier/DNA complexes away from the non-productive acidic compartment, re-rerouting them onto then microtubular networks stabilized by the use of chemosensitizers.

Accordingly, the present disclosure provides a composition for transfecting a cell with a genetic material, comprising a first agent capable of directing the genetic material away from an acidic compartment in a cell and a second agent capable of stabilizing the microtubule or a network thereof.

In one embodiment, the first agent may be capable of directing genetic material away from a non-productive acidic compartment of the cell. In another embodiment, the first agent may be, but is not limited to, a lipid, a peptide fusiongenic agent or a combination thereof.

In one embodiment, the lipid fusogenic agent may be selected from DOPE, CHEMS, DPPC and DOPC and combinations thereof.

In one embodiment, the peptide fusogenic agent may be at least any one of, but not limited to, haemagglutinin (HA2-peptide), influenza-derived fusogenic peptide diINF-7, T domain of Diphtheria toxin and polycationic peptides, such as polylysine and polyarginine, or combinations thereof.

In one embodiment, the aforementioned peptide fusogenic agent may be chemically modified by attachment of a lipid.

In one embodiment, the aforementioned peptide may be chemically modified by attachment of a biomolecule, such as a nucleic acid or a synthetic carrier, such as a cationic polymer.

In one embodiment, the second agent may be capable of enhancing tubulin acetylation. In another embodiment, the second agent may be capable of enhancing the sensitivity of the cell to a therapeutic agent and/or may be capable of modifying the host genetic status.

In one embodiment, the aforementioned second agent may be selected from a histone deacetylase inhibitor (HDACi), a tubulin binding agent (TBA) and siRNA that is capable of directly or indirectly affecting the microtubule network stability. The HDACi may be selected from Tubastatin A, belinostat, bufexamac, panobinostat, PCI-24781, SAHA (vorinostat), scriptaid, trichostatin A, valporic acid, B2, salermide, sirtinol and combinations thereof.

In one example, it is shown that the TBA of the second agent of the present invention may be selected from taxanes, epothilones, and a combination thereof. The taxanes may be paclitaxel, docetaxel or a combination thereof.

In a further example, the taxanes may be selected from a group consisting of cremophor EL® Taxoprexin® (Docosahexaenoic acid-paclitaxel), Xytotax™ (paclitaxel polyglumex), TOCOSOL® paclitaxel, BMS-184476, DJ-927, BMS-275183, RPR 109881A, Ortataxel, Genexol (co-polymer combination), LEP (liposomal-encapsulated paclitaxel) and taxol in vitamin E emulsion.

In one example, the epothilones may be patupilone, ixabepilone, BMS 310705, sagoilone, KOS-862, KOS-1584, or combinations thereof.

In one embodiment, the chemosensitizers may be histone deacetylase inhibitors (HDACi), tubulin binding agents, taxanes and siRNA, capable of directly or indirectly affecting the microtubule network stability.

Advantageously, the chemosensitizers used in the present disclosure are known to have anti-neoplastic, anti-inflammatory, anti-angiogenic or neuroprotective effects in vivo.

In one embodiment, the genetic material may be coupled to at least one cationic species. The cationic species may be selected from polyethylene imine, polycationic amphiphiles, DEAE-dextran, cationic polymers, their derivatives and combinations thereof. Furthermore, the cationic species may be a cationic polymer such as a dendimer, branched-polyethylenimine (BPEI), linear-polyethylenimine (LPEI), Poly (amindoamine) (PAMAM), XTREMEGENE HP® (DNA transfection reagent), and combinations thereof. In one embodiment, wherein the cationic species is LPEI.

In one embodiment, the nucleic acid:polymer (N/P) ratio cationic species to the genetic material may be selected from the group consisting of from about 0 to about 1000, about 0 to about 900 about 0 to about 800 about 0 to about 700 about 0 to about 600 about 0 to about 500 about 0 to about 400 about 0 to about 300 about 0 to about 200 about 0 to about 100 about 0 to about 75 about 0 to about 50 about 0 to about 25 between about 0 to about 15, between about 0 to about 10, and between about 0 to about 5. In one embodiment, the nucleic acid:polymer (N/P) ratio of genetic material to cationic species may be 20.

In one embodiment, the N/P ratio is the ratio of the cationic species to the genetic material forming polyplexes within the composition.

In another embodiment, the genetic material may be a nucleic acid sequence. In another embodiment, nucleic acid sequence may be selected from the group consisting of DNA, RNA, mRNA, ribozymes, antisense oligonucleotides, modified polynucleotides and combinations thereof.

In one embodiment, the cell is a differentiated or undifferentiated cell. In one embodiment, the cell may be selected from the group consisting of nervous systems cell, liver cell, hematopoiesis cell, peripheral blood cell, umbilical blood cell, bone marrow cell, tumour cell, ischemic tissue cell, T cells, B cells, skin cells and combinations thereof.

In one embodiment, the cell may be isolated from a biological sample. In one embodiment, the biological material may be selected from the group consisting of a sample of fresh tissue, frozen tissue, paraffin-preserved tissue and/or ethanol preserved tissue. In another embodiment, the biological material may be selected from the group consisting of whole blood or a component thereof, lymph, bile fluid, cerebrospinal fluid, bronchioalveolar lavage fluid, synovial fluid, semen, ascitic tumour fluid, breast milk, amniotic fluid, a buccal smear and pus.

In one embodiment, the first agent and the second agent may be provided to the cell simultaneously, separately or sequentially. In one embodiment, the first agent and the second agent may be provided within the first hour of transfection of the cell with the genetic material. Alternatively, the first agent and the second agent may be provided within about 2, 3, 4, 5, 6, 7, 8, 9, 10 hours of transfection of the cell with the genetic material In one embodiment, the second agent may be provided after the first agent. In one embodiment, the second agent may comprise a two or more therapeutic agents as described herein.

In one embodiment, the composition as described herein may be used in gene therapy.

In one embodiment, the composition as described herein may further comprise a therapeutic agent. The therapeutic agent may be chemotherapeutic agent. In one embodiment, the chemotherapeutic agent may be selected from the group consisting of taxanes, paclitaxel, docetaxel and epothilones, and combinations thereof.

In one embodiment there is provided a method of treating a patient in need of gene therapy comprising administering a genetic material and a composition as described herein.

In another embodiment, there is provided the use of a composition as described herein in the manufacture of a medicament for treating a disease, selected from a group consisting of cancer, SMA, bone cancers, leukemia, blood cancers, sickle cell disease, Wiskott-Aldrich Syndrome, HIV, genetic disease, diabetes, monogenic, infectious neurological, ocular, inflammatory, cardiac and neurodegenerative diseases.

In a further embodiment, the composition as described herein may be used for gene marking.

In one embodiment, there is provided a method of delivering a genetic material into a cell comprising the step of administering the genetic material with the composition as described herein. The method may be performed in vitro or ex vivo or in situ.

In one embodiment, here is provided a composition comprising a first agent, as defined herein, and a second agent, as defined herein.

In another embodiment, there is provided a kit comprising a first agent, as defined herein, and a second agent, as defined herein, a therapeutic agent as defined herein and instructions for use.

The present disclosure further encompasses therapeutic genes or genetic material. As exemplified in the examples below, this genetic material may comprise of, but is not limited to, nucleic acid sequences, encoding for any one gene or part thereof, which upon entering the cell having then a therapeutic effect upon the target gene by possibly enhancing expression or by possibly decreasing expression by interacting with the target sequence. It should be understood that the genetic material, including therapeutic genes, may differ from any exact sequences illustrated and described herein. Thus, the invention contemplates deletions, additions and substitutions to the sequences shown, so long as the sequences function in accordance with the methods of the invention. For the purpose of the present invention, any method of quantifying genetic material is appropriate for use in the context of the invention and many are known in the art. For example, the genetic material may be isolated using techniques known to the art, e.g. restriction enzymatic digest, polymerase chain reactions (PCR), agarose gel electrophoresis, size exclusion chromatography and many more. Furthermore, the isolated genetic material may be quantified using methods known in the art, that may be, but are not limited to, spectrophotometric analysis, fluorescent labelling, quantitative PCR (qPCR, also known as real-time PCR), and e.g. DNA microarray (CHIP) analysis for the determination of gene expression levels after transfection. All the methods disclosed may be used consecutively in any possible order.

The composition as described herein may be used in many different applications, all of which have/pertain to the use of TrafEn™ as a unique approach, wherein the simultaneous effects of both genes and drugs (e.g., HDACi) with microtubule modifying activities and/or epigenetic modifying activities may be useful for all the areas described below.

Cell therapy refers to the process of introducing cells to restore normal function; which was lost due to age, disease, damage, or congenital defects. There are many forms of cell-based therapy, including stem cells and immune cells and cancer cells. Additionally, HDACi is known to effect processes in stem cell differentiation and reprogramming of somatic cells into induced pluripotent stem cells (iPSCs), broadening the application of TrafEn™ in cell based therapy. These cell based therapies may be utilised, but are not limited to, the application of stem cells, e.g. negative or positive selection for the segregation of modified populations, and/or controlling the growth of stem cells and their progeny, e.g. when inserting a suicide gene into the stem cells population to enable the use of external stimuli to eradicate uncontrolled cell proliferation. Further applications for this invention may also be modifying stem cells to delivery gene product, which depending on the application, may require long-term or transient expression of therapeutic gene. Cases like wound healing, bone regeneration, angiogenesis, and repair of central nervous system injury, transient expression would be preferable examples. On the other hand, to correct genetic disease, persistent gene expression is required.

Another possible application of this invention is modulating differentiation in stem cells via a transfer of genes mediated by this invention. Another potential application of gene transfer to stem cells is to provide genetic signals, improving the outcome of differentiation protocols know in the art. The possibilities of directing cell differentiation through gain—(plasmid DNA) or lost—of function (shRNA, siRNA, miRNA), lead to a more pure population of differentiated cells, thus becoming a particularly attractive example of this invention, as the clinical applicability of differentiating and reprogramming cells in cell based therapy is known to be driving the exploration of the use of various types of stem cells, which may be, but are not limited to, induced pluripotent stem cells, mesenchymal stem cells, neural stem cells, iPSCs, ESCs, human embryonic stem cells (hESCs), ASCs, hematopoietic (HSCs) and mesenchymal stem cells (MSCs), Neural stem cells (NSCs), immune cells (boosting of T-cell function), cancer cells (for cancer vaccinations) and genetically modified variations thereof, neurons, microglia, astrocytes Possible applications of the composition as described herein for the treatment and therapy, e.g. cell based and gene therapy/therapeutics of any one of, but not limited to, the following diseases: SMA (via iPS cell based therapy), bone cancers, leukemia, blood cancers, cancers (anti-angiogenic, stopping cell growth), HSC therapies for sickle cell disease and Wiskott-Aldrich Syndrome, gene treatment for cancer, HIV infection and genetic disease, repair damaged tissues, diabetes (T1D and T2D), cardiac disease, neurodegenerative diseases, for example, Parkinson's disease.

The composition as described herein may also be used additionally as a method for reprogramming cells, and or transdifferentiation of cells. Genetic tools known in the art have been established to initiate reprogramming process in various cell types.

Furthermore, it has been suggested that HDACi may play a possible role in promoting transdifferentiation. It has been shown in the art that HDACi induced expression of SOX9 in hepatocytes, which normally lack SOX9. The aberrant expression of SOX9 induced expression of COL2A1 and COMP1, which is usually found during chondrogenesis. These observations demonstrate redeployment of a typical developmental process to an atypical setting may be initiated by treatment of cells with HDACi.

EXPERIMENTAL SECTION

Example 1

Mild Centrifugation Improved Transfection Efficiency and Reduced Cytotoxicity in Neuronal Cells To establish an optimal protocol for transfection of neuronal cells, cellular toxicity to bolus transfection, where the cells were exposed to a defined composition of polyplex for a period of time, was first investigated. Increasing N/P ratios of polyplex was found to reduce cell viability of native Neuro2A and NG-108 cells even in the presence of serum (FIG. 11). We hypothesized that cytotoxicity at high N/P ratio was due to prolonged exposure of cells to toxic free polymer, and shortening the period of incubation should reduce toxicity. However, transfection efficiency was significantly reduced with shorter periods of incubation (15 min or 1 h, FIG. 12a). Mild centrifugation was previously reported to improve transfection. Next, this approach was explored as an attempt to improve transfection at short incubation periods. As hypothesized, shorter incubation (15 min) coupled with mild centrifugation resulted in transfection efficiency comparable to bolus transfection (FIG. 12b). As previously reported, it was found that LPEI/pDNA polyplex aggregate and deposit extensively in salt containing physiological media (FIG. 13), which may explain the beneficial effect of mild centrifugation in transfection.

Example 2

Polyplex Formed Aggregates and were Sedimented by Mild Centrifugation

Expectedly, dynamic light scattering studies showed that nanosized LPEI/pDNA (~100 nm) rapidly increased in size when placed in DMEM (FIG. 13a), consistent with low colloidal stability and the formation of aggregates in high salt conditions (Wightman, L., et al. J Gene Med, 2001. 3(4): p. 362-72; Mishra, S., P. Webster, and M. E. Davis. Eur J Cell Biol, 2004. 83(3): p. 97-111). The deposition of these large aggregates over time was likely to account for the presence of distinct particulates found on the surface of cell culture plates after the incubation of LPEI/pDNA polyplexes in Dulbecco's minimum essential medium DMEM (but not in HEPES) (FIG. 13b). These large heterogeneous particulates (>0.5 µM) on the surface of the wells were observed even in the absence of cells, ruling out the possibility of cellular artefacts. In order to quantify the amount of pDNA in the supernatant, pDNA was efficiently released from the polyplexes and measured by qPCR. After centrifugation, the amount of pDNA in the supernatant was significantly reduced, indicative of the sedimentation of polyplexes in DMEM (FIG. 38). Collectively, these observations were indicative of the sedimentation of aggregated polyplexes onto the substrate over time and the deposition of these aggregates was enhanced by mild centrifugation.

Example 3

Centrifugation Enhanced Transfection Resulted in Efficient Gene Delivery into Native but not Differentiated Neuronal Cells This approach was then applied to transfect differentiated Neuro2A and NG-108 cells. Both cell-lines were pharmacologically induced to differentiate and showed elaborate neurite outgrowths prior to transfection (FIG. 5b). Intriguingly, both differentiated cell types were poorly transfected as compared to the same native cells (FIG. 5a, b). Indeed, most of the EGFP positive cells demonstrated undifferentiated phenotype, where only ~3% of the EGFP positive cells were found to bear neurites twice the body length (FIG. 5c). Increasing the N/P ratio (from 10 to 50) did not increase the efficiency of transfection. Similar to native cells, negligible toxicity was observed in differentiated cells post-transfection (FIG. 14). Collectively, these observations demonstrated that differentiated neuronal cells were refractory to transfection with LPEI/pDNA polyplex as compared to the matched native cells.

Example 4

Cellular Binding and Internalization of Polyplex was not Affected after Neuronal Differentiation To assess if DNA uptake was affected upon neuronal differentiation, the total amount of DNA associated with the cells was measured by quantitative real-time PCR (qPCR) in differentiated and native cells. To quantify the amount of pDNA associated with cells, pDNA was efficiently released from the polyplex and measured by quantitative real-time PCR (qPCR) (FIG. 15b, c). The lysis solution used to release pDNA from polyplex did not affect the qPCR reaction (FIG. 15a). Comparable amounts of DNA (~$10^6$ copies/cell) were associated with native and differentiated cells over time (FIG. 16), indicative that the polyplex associated equally well regardless of the differentiation state of the cells. To examine whether the polyplex were internalized in differentiated cells, cells were transfected with Rhodamine-pDNA. The fluorescence of extracellular polyplex was effectively quenched using trypan blue (FIG. 17). Intriguingly, intracellular fluorescent signal intensities were detected at significant levels in both native and differentiated cells (FIG. 6a). This observation was further confirmed by qPCR, showing comparable amounts of pDNA internalized in native and differentiated cells 4, 24 and 48 h post-transfection (FIG. 6b). Extracellular pDNA was effectively removed by pAA/DNase treatment prior to qPCR measurements (FIG. 18). These results suggested that cellular association/uptake of aggregated polyplex were not significantly different after neuronal differentiation.

Example 5

Polyplex Internalization in Native, but not Differentiated Neuronal Cells, Involved PKC To test the hypothesis that distinct biochemical mechanisms may be involved in the uptake of polyplex in native and differentiated cells, we examined the contributions of various signalling pathways pharmacologically. Dynasore, an inhibitor of dynamin GTPase activity, significantly inhibited the uptake of polyplex in differentiated and native Neuro2A cells. Filipin III, a cholesterol sequestration agent, did not affect polyplex uptake in either phenotypes. Intriguingly, Rottlerin, a protein kinase C inhibitor, reduced the uptake of polyplex significantly in native but not in differentiated cells (FIG. 7a). The effects of these inhibitors on expression of the transgene were similarly correlated (FIGS. 7b and c). The effect of PKC inhibition on transfection was further confirmed with another PKC inhibitor, GÖ6983 (FIG. 19). Similar observations were also made with NG-108 cells (FIG. 20). The differential involvement of PKC in the internalization of polyplex is consistent with the suggestion that cellular trafficking mechanisms have altered upon neuronal differentiation.

Example 6

Sedimented Polyplex were Bioavailable and Mediated Efficient Transfection

Particle size is thought to affect endosomal uptake, intracellular transport and nuclear entry, and the size dependency may differ in different cell types and applications. To address the contribution of size to transfection, pre-complexed LPEI/pDNA in DMEM was first passed through a 0.22 µm filter. The filtrates were then used to transfect cells (see experimental design in FIG. 39). Interestingly, the removal of polyplex aggregates from the transfection solutions almost completely abolished transfection (FIG. 40a). In contrast, filtrates of LPEI/pDNA pre-complexed in HEPES (average size of polyplex<200 nm) could efficiently transfect cells after incubation in DMEM (FIG. 41). Furthermore, a second filtering step upon incubation of HEPES filtrates in DMEM abolished the transfection. These findings supported the hypothesis that polyplexes aggregate only in high salt medium and are critical for efficient transfection. In parallel, the amount of pDNA in the filtrates were significantly reduced, suggesting that large, aggregated polyplexes (>200 nm) has been effectively removed by filtration (FIG. 42). Next, the hypothesis was tested that suggested aggregated polyplexes deposited on the surface of the substrate could efficiently transfect cells. Aggregated polyplex was first sedimented by mild centrifugation onto the surface of the wells, the supernatant removed and the wells were washed with media. Neuro2A cells were then seeded directly onto these surfaces pre-loaded with sedimented polyplex aggregates. Interestingly, the cells were efficiently transfected, suggesting that these sedimented aggregates were highly bioavailable (FIG. 40a) and the percentage of cells transfected correlated to the amount of pDNA in the polyplex (FIG. 40b). The above observations led us to the question as to how such large aggregates were internalized by cells. It has been proposed that surface immobilized LPEI/pDNA polyplexes mediate transfection by releasing significant amounts of nanosized polyplexes into the media, thus allowing the polyplexes to be internalized by the cells. To test the hypothesis that surface deposited aggregates release significant amounts of pDNA into the media, the distribution of pDNA in the culture system was measured over a period of 48 h. In the presence or absence of cells, the amount of pDNA released into the media was <1% of the total amount of pDNA found in the well throughout the 48 h period of incubation, suggesting that pDNA was not efficiently released from the surface bound aggregate (FIG. 43).

Example 7

Intracellular Plasmid DNA was Localized to Acidic Compartment in Differentiated Neuronal Cells A comparison of the intracellular behaviours of LPEI/DNA polyplex and adenovirus in primary neurons demonstrated that the polyplex, but not adenovirus, was found to be sequestered in acidic compartment, possibly accounting for the poor transfection efficiency of polyplex. As transfection was found to be highly efficient in native but not differentiated cells (FIG. 5a), we hypothesized that changes in intracellular trafficking of polyplex may be a critical reason. To test this hypothesis, we exploited the pH sensitive property of fluorescein to examine the intracellular localization of polyplex.

After extracellular fluorescence was quenched by ethidium bromide (EtBr), distinct fluorescence was observed in majority of native cells but significantly reduced in differentiated cells when transfected with polyplex containing FITC-pDNA (FIG. 8a). To verify that pDNA was taken up into the cells, polyplex containing Rhodamine-pDNA (pH insensitive) was similarly transfected into both native and differentiated cells. Rhodamine-pDNA was observed in majority of both native and differentiated cells; further supporting the observation that both phenotypes internalized polyplex efficiently (FIG. 6). Percentage of cells containing FITC- or Rhodamine-pDNA was comparable in native cells while FITC/Rho ratio was significantly lower in differentiated cells; indicating quenching of intracellular FITC (FIG. 8b). Taken together, these data suggested the sequestration of polyplex in acidic compartments in differentiated but not native cells. To test whether this is a general phenomenon, similar experiments were performed on differentiated NG-108 cells as well as primary cortical neurons. Consistently, quenching of FITC was observed (FIGS. 21 and 22); suggesting polyplex trafficking to acidic compartment may be an important factor contributing to the poor transfection of differentiated neurons.

To validate the trafficking of pDNA to acidic compartment in differentiated cells, co-localization of pDNA with lysosensor green labelled acidic compartment was visualized using confocal imaging. Localization of Rhodamine-pDNA to the acidic compartment was observed 4 h post transfection and increased over time (24 h) in both Neuro2A (FIG. 8c, d) and NG-108 cells (FIG. 23). It is worthy to note that the total pixel count of labelled acidic compartment per cell was significantly higher in differentiated cells (FIG. 24). These results suggested that intracellular trafficking of polyplex to acidic compartments directly or indirectly in differentiated neurons may in part contribute to the poor transfection efficiency.

Example 8

Escape of Polyplex from Acidic Compartment Enhanced Transfection in Differentiated Cells It was hypothesized that facilitating the escape of polyplex from the acidic compartment may increase transfection efficiency. Addition of pH sensitive DOPE/CHEMS resulted in a 10-fold augmentation of transfection efficiency in differentiated neurons (FIGS. 9a and b). To investigate the fusogenic effect of DOPE/CHMES, trafficking of polyplex to acidic compartment was examined with labelled pDNA. As expected, the amount of DNA localized in the acidic compartment was drastically reduced after treatment with DOPE/CHEMS (FIGS. 9c and d), similar to the intracellular localization profile observed in native cells. Real-time tracking of the release of polyplex from the compartment (FIG. 25) clearly revealed the ability of DOPE/CHEM in facilitating the escape of polyplex from the acidic compartments. In addition, the effect of DOPE/CHEMS was found to be temporal, where the optimal effect was achieved when the chemical was added immediately after centrifugation (FIG. 26). Evidently, the localization of polyplex to acidic compartment in differentiated neurons led to poor transfection, which can be improved by enhancing endosomal escape of polyplex using fusogenic lipids.

It is also worthy to note that chloroquine, a lysosomotropic compound known to inhibit fusion of the endosome and reduce enzymatic degradation of DNA by buffering the vesicular interior, did not show cumulative enhancement of transfection. Similar observations were found with PLUS™ reagent and INF7 fusogenic peptide (FIG. 27) when these reagents were added to the culture post-transfection. Additionally, LPEI mediated delivery of pDNA pre-complexed with PLUS reagents and INF7 fusogenic peptide did not improve transfection in differentiated neuronal cells (FIG. 28).

Example 9

Enhanced Microtubule Mediated Trafficking and Endosomal Escape of Polyplex Enabled the Efficient Transfection of Differentiated Cells Microtubule mediated transportation is known to play a role in the polymer/pDNA trafficking to the nucleus. Armed with the capability in releasing polyplex from the acidic compartments, we next explored the influence of chemotherapeutic mediators of intracellular trafficking as a strategy to further enhance transfection efficiency. In particular, Tubastatin A, a histone deacetylase-6 (HDAC6) inhibitor that enhances microtubule mediated intracellular transport of cargo, was evaluated. The co-administration of DOPE/CHEMS and Tubastatin A resulted in a highly significant increase in the number of EGFP positive differentiated Neuro2A (~70%) (FIG. 10a and b). A time course study revealed that minimal exposure of cells to DOPE/CHEMS and Tubastatin A for 12 h is required for high transfection efficiency (FIG. 29). Interestingly, the combinatorial effect of DOPE/CHEMS and Tubastatin A was found to be carrier dependent, enhancement in transfection occurred when LPEI, PAMAM, and XTREMEGENE XP but not Fugene HD was used (FIG. 30). Additionally, Trichostatin A, an alternative HDAC inhibitor (HDACi), greatly enhanced transfection efficiency in the presence of DOPE/CHEMS (FIG. 31). Next, the strategy of mild centrifugation to sediment aggregated polyplex with the co-administration of DOPE/CHEM and Tubastatin A, was evaluated on primary cortical neurons. Remarkably, close to 75% of these post-mitotic cortical neurons were transfected (FIG. 10c and d) without significant cytotoxicity (FIG. 32a). It should be noted that optimal transfection occurred only when reagents were co-administered within the first hour of transfection (FIG. 32b). To further confirm the significance of microtubular stabilization for efficient transfection, the effect of paclitaxel and various HDACi on tubulin acetylation and transfection was examined. In line with previous reports, HDAC6targeting small molecules (Tubastatin A, TSA, Varinostat/SAHA) and paclitaxel but not Entinostat, Tacedenaline markedly enhanced tubulin acetylation (FIG. 33). Additive effect on transfection was observed when cells were treated with DOPE/CHEMS and small molecules that induced tubulin acetylation (FIG. 34). All together, these data suggested the endosomal escape and microtubular stabilization enhanced transfection through a concerted mechanism.

Enhancement of transgene expression is achieved by TrafEn™ combinations acting on the endosomal trafficking and the stabilization of microtubular network. The effect of TrafEn™ on transfection enhancement has been examined in various conditions including—cell types, gene carriers, genetic material and HDACi.

Example 10

Effect of TrafEn™ Differed in Various Cell Types

It is known that various cell types and even cell lines from the same tissue origin displayed differential transfection efficiencies. Extending the TrafEn™ principle findings, significant enhancements of transfection were also observed with several cell types (FIG. 44), lending further evidence that the coordinated endosomal release and the stabilization of microtubule network contribute significantly to transfection efficiency. Additionally, this approach can produce cell line models of the same tissue of origin with comparable expression levels of transgene by controlling transfection efficiencies.

Example 11

TrafEn™ Enhanced Transfection of Various Commercial Gene Carriers

The combinatorial effect of DOPE/CHEMS and Tubastatin A was also found to enhance the transfection efficiencies of a number of commercially available polymers beside LPEI (FIG. 45). All commercial reagents, except XTREMEGENE HP, performed poorly when the transfection experiment was conducted with manufacturer's protocol. Transfection enhancements were observed when the manufacturer's protocol was replaced with the deposit mediated transfection workflow. Further enhancement was achieved with addition of TrafEn™reagent. Enhancement of transfection by facilitating endosomal escape and microtubule trafficking of the various polymers suggested the transfection mechanisms of different carriers may be similar.

Example 12

TrafEn™ Enhanced Transfection of shRNA

Genetic manipulations may be accomplished by either gene overexpression using plasmid DNA (pDNA) or gene knockdown with short hairpin RNA (shRNA). To date, a library of shRNA had been designed to suppress the expression of desired genes in mammalian cells. For example, repression of PTB with shRNA was reported to elicit cellular reprogramming and transdifferentiate a multiple cell types to neuronal like cells. To demonstrate the TrafEn™ effect on gene knockdown, a case study showing efficient repression of the RNA binding polypyrimidine-tract-binding (PTB) protein in the presence of TrafEn™ is presented. The mRNA level of PTB1 in HeLa cells (cervical cancer cell line) were examined after transfection. Evidently, the knockdown efficiency is more efficient in the presence of TrafEn™ (Bars 1 to 4, FIG. 46). The efficient gene knockdown contributed to the rapid transdifferentiation process where neuronal like cells were observed after 8 days of treatment (FIG. 47).

Example 13

Gene-drug Combinatorial Strategy

Figure 1:
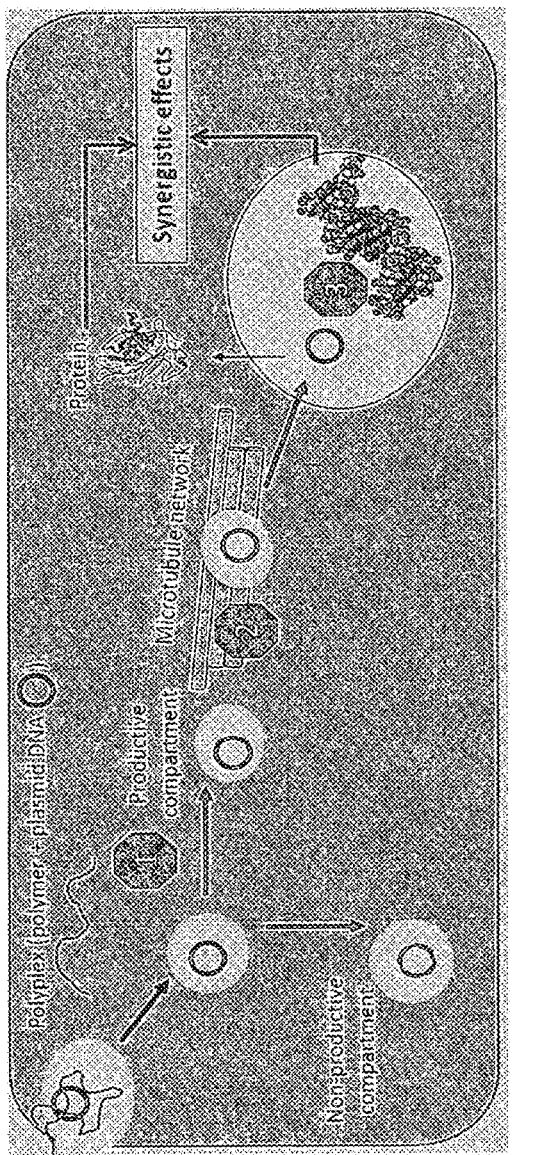
FIG. 1 shows a schematic of the possible effects of TrafEn™. It contains an optimized mix of chemoRe-router that specifically re-directs polyplexes away from the acidic compartment (step 1) and re-routing onto microtubular networks stabilized by the use of chemosensitizers (step 2) (e.g., histone deacetylase inhibitor (HDACi), taxanes). The chemosensitizers synergize with the gene product to achieve beneficial therapeutic effects (step 3). TrafEn™ may also be used to improve intracellular trafficking of therapeutic material.

By coupling the effect of the time-dependent rerouting from non-productive endosomal pathway using DOPE/CHEMS with a microtubular network stabilizer HDAC6 inhibitor, enhancement of transfection has been demonstrated in a number of cell types. Some HDAC inhibitors such as Trichostatin A (TSA) and Varinostat (SAHA)

enhance transfection by targeting microtubule and at the same time exert epigenetic modification activities. The effects of these substances on the histone and non-histone acetylation status have implications in various clinical applications. For example, HDACi has been used as chemosensitizer to increase cytotoxic effect of a therapeutic agent for cancer (A), to induce differentiation of stem cell (B), to increase immunogenicity of cancer vaccine (C) and to enhance reprogramming process (D). The realization of the broad clinical applications of HDACi has led to studies which explore the possibility of a drug-gene combinatorial effect DOPE/CHEMS and HDAC6 inhibitor work together to enhance transfection efficiency (1 and 2, FIG. 1) and HDACi may augment the effect of the transgene through epigenetic modification (3, FIG. 1). In other words, the gene-drug combinatorial strategy simultaneously increases transgene expression and the synergistic effect/s of HDACi may further accentuate the therapeutic effect.

Example 14

Synergistic Effect of p53 Overexpression and SAHA to Induce High Cytotoxicity

It is known that treatment with single anti-cancer agents such as gene therapy and HDACi alone often demonstrate limited clinical benefit for patients with solid tumour. For instance, anti-cancer regime with single therapeutic agent such as p53 replacement therapy and SAHA has shown poor clinical outcome, prompting the development of novel combination regime with other cancer therapeutics. p53 is known to be involved in numerous functions including the regulation of cell cycle, DNA repair and activation of apoptosis. The efficacy of p53 replacement therapy has been tested in glioma, which 30-60% of this cancer were found to display mutations in p53. Despite the many preclinical and clinical studies conducted to date, none has progressed beyond phase I trials. On the other hand, SAHA has shown moderate clinical benefits as monotherapies but has garnered much excitement in combination therapy. SAHA has been shown to exert potent anti-tumour effects in a broad variety of cancer cells at concentrations that have minimal toxic effects on normal cells. Although the underlying anticancer mechanisms of SAHA are still unclear, it is likely that it exerts epigenetic modification that altered gene expressions resulting in growth arrest, migration inhibition and cell death. A study has shown SAHA induced up-regulation of pro-apoptotic genes (Bax, Bim, Bmf, Bik, cytochrome C and Smac) and down-regulation of anti-apoptotic genes (XIAP and survivin). Other study has shown that the susceptibility of SAHA induced cell death was regulated by p53. These observations suggest a possible synergistic effect of SAHA with p53, and thus, suggest a possible combinatorial gene-drug effect. To illustrate the synergistic effect of the gene-drug combination (TrafEn™), the therapeutic outcome of combined p53 and HDACi treatment was examined in U251MG glioma cell line (U251MG). The strategy presented here demonstrates the combinatorial effect of enhanced p53 transfection efficiency by DOPE/CHEMS and SAHA, which the latter compound may also produce an epigenetic effect. First, the effect of DOPE/CHEMS and SAHA on transfection enhancement was confirmed in U251MG glioma cells (p53 mutant) (FIG. 48). Following transfection, treatment of cells with single or combination of the various reagents (DOPE/CHEMS, Tubastatin A and SAHA) resulted in significant enhancement in transfection efficiency. Interestingly, in all cases, the percentage (%) of cells expressing high level of GFP (as determined by the RFU) was increased significantly in the presence of transfection enhancers. The co-administration of DOPE/CHEMS and Tubastatin A/SAHA displayed superior effect over treatment with single reagent. Next, the combinatorial effect of p53 with the transfection enhancers was examined. Compared to the negative control (−ve), the cell viabilities were affected to various extent (FIG. 49). Significant reduction in cell number was observed with p53 but not PMAXGFP overexpression, suggesting that cell death was p53 dependent (possibly through apoptotic pathway as suggested by other studies. Further increment of cell death with p53 was found in the presence of DOPE/CHEMS, a non-toxic fusogenic lipid, thus, providing evidence of enhanced killing of cells by improving transfection efficiency. While transfection efficiencies of U251MG treated with DOPE/CHEMS or SAHA were comparable (FIG. 48), combination of p53 and SAHA resulted in more cell death of U251MG cells. This observation is consistent with the reported chemosensitizing effect of SAHA on anti-cancer action. Intriguingly, p53 delivery to cells in the presence of DOPE/CHEMS and SAHA exhibited superior cytotoxic effect (with ~95% reduction of cell number) over other conditions where transfection enhancers were added individually. This data supported our hypothesis that the anti-cancer drug and transgene product synergise with each other, augmenting the therapeutic outcome. Furthermore, increasing the duration of incubation with SAHA did not further reduce the cell number (FIG. 50). Next, the effect of Tubastatin A (cytosolic HDAC6 specific inhibitor) was compared with SAHA to further confirm the contribution of the epigenetic modulation of SAHA on p53 induced cell death (FIG. 51). Unlike SAHA, Tubastatin A did not result in greater reduction of cell number as compared to DOPE/CHEMS. As expected, transfection of p53 with Tubastatin A and DOPE/CHEMS did not contribute to the drug-gene combinatorial effect as observed with the use of SAHA.

Accumulating evidence suggests that glioma heterogeneity likely is the key reason to treatment failure. To date, two subpopulations, known as TMZ resistant cells and cancer stem cells, have been identified. Both of the subpopulations have developed genetic mechanisms that exhibited aggressive cancer phenotypes such as migration and resistance to TMZ. The cancer stem cells hypothesis is well recognized as a challenge for treatment, due to resistance. These cells exhibit stem cell-like characteristics and are capable to generate heterogeneous tumour masses. Recent studies support the presence of small number of cancer stem cells in glioma (GSC). As these cells are resistant to radiotherapy and chemotherapy, they are sufficient to generate recurrent tumour. Next, the synergistic effect of the gene-drug combination using p53, DOPE/CHEMS and SAHA was examined in U251MG cells resistant to 40 μM TMZ (TMZR-U251MG) and GSC (FIG. 52). Evidently, the strategy has superior cytotoxic effect, resulting in 89.1% and 91.7% reduction in cell number of TMZR-U251MG and GCS respectively. Interestingly, overexpression of p53 alone resulted in significant cell death in TMZR-U251MG but has no effect in GSC. This has not been reported and is the first time that the effect of overexpression of p53 was examined in the parental, TMZ resistant cells and GS.

Example 15

Synergistic Effect of BMP2 Overexpression and TSA to Induce Osteogenic Differentiation To realize the clinical application of stem cells, technologies must be established, to direct stem cells to differentiate in a regulated manner, to circumvent immunogenicity of non-autologous stem cells-derived cells and to function as drug delivery vehicles and to regulate the growth of cells post-transplantation. Gene delivery is a potential tool to deliver biological signals to address these challenges. The applications of TrafEn™ gene-drug combination in stem cells technologies was illustrated with mesenchymal stem cells (MSCs).

To examine the drug-gene combination effect, we first examined the effect of TSA (HDAC6 inhibitor and epigenetic modifier) in transfecting MSC (FIG. 53). The addition of DOPE/CHEMS and TSA individually led to significant enhancement of transfection but no further enhancement was observed in when used in combination. Next, the expression levels of BMP2 in the presence or absence of DOPE/CHEMS and/or HDACi (TSA, Tubastatin A) in MSC were quantified using qPCR to test a drug-gene combinatorial effect (FIG. 54). Significant increase in the expression level of BMP2 was observed 3 day post transfection (~13,000 fold over the negative control) with PMAXGFP-BMP2 (BMP2). The addition of DOPE/CHEMS (BMP2+DOPE/CHEMS) or Tubastatin A (BMP2+5 µM Tubastatin A) enhanced BMP2 expression by ~20,000 fold. Surprisingly, treatment with TSA did not further enhance BMP2 expression (BMP2+150 nM TSA). Intriguingly, combination of DOPE/CHEMS and TSA elicited a far superior effect on BMP2 overexpression (~200,000 fold as compared to control) than the combination of DOPE/CHEMS and Tubastatin A (~80,000 fold). These unanticipated results are suggestive of a distinct function of TSA beyond merely stabilizing the tubulin network in enhancing BMP2 expression and that this can serve as an opportunity to identify novel effects of gene-drug combinations by using specific HDACi. It is worthy to note that prolonged expression of transgene of up to 21 day in MSC culture was observed with cells were treated with DOPE/CHEMS and TSA (FIG. 55). This finding indicates potential efficient cell therapy with prolonged released of therapeutic product. While further characterization and functional analysis are required to validate BMP2 release and osteogenesis, we observed extensive calcium deposition at the end of the study in cells maintained in osteogenesis defined media (FIG. 56B) but not in expansion media (FIG. 56A).

Example 16

Synergistic Effect of GM-CSF Overexpression and SAHA to Improve Immunogenicity of Cancer Cells Cancer vaccine can be generated from the genetically modified tumour cells, either autologous (removed from patients during surgery) or allogeneic (established cancer cell lines). After genetic modification, cells are inactivated by radiation and injected to the patients subcutaneously or intradermally to induce recipient's immune response against the tumour cells. Utilization of allogeneic cells, such as existing cell lines, provides a sustained and unlimited source of well-characterized cells, which can be standardized for large-scale production. It may also provide single batch for clinical lot for comparative analysis of clinical result and eliminates the need to continuous harvest patient's cancer cell. Furthermore, there is no longer the requirement of tailor-made individual cancer vaccine, which may increase cost and labour. To date, the most advanced cell line based cancer vaccine is GVAX, comprising PC3 cells modified with GM-CSF gene for metastatic prostate cancer treatment. Modified PC3 cells are able to activate antigen-presenting cells (APC) and induce immune response. HDACi, on the other hand, can augment the immunogenicity of tumour cells by increasing expression of major histocompatibility complex (MHC) class I and II proteins, co-stimulatory/adhesion molecules. Moreover, treatment with HDACi such as SAHA and TSA has been found to associate with enhanced presentation of MICA and MICB on the surface of cancer cells but not normal cells. MICA and MICB induce activation of immunoreceptor, natural killer cell protein group 2D (NKG2D), resulting in the increased susceptibility of cancer cells to natural killer cells (NK cells; CD4 and CD8 T cells). Here, we aim to examine the combination of GM-CSF and SAHA in augmentation of the immunogenicity of PC3 cells. This TrafEn™ gene-drug strategy may generate PC3 cancer vaccines, that are capable to activate both APC and NK cells.

The effect of SAHA (HDAC6 inhibitor and epigenetic modifier) in transfecting PC3 was first examined (FIG. 57). The addition of DOPE/CHEMS, Tubastatin A and TSA individually led to significant enhancement of transfection but no further enhancement was observed in when used in combination. Next, the expression levels of GM-CSF in the presence or absence of DOPE/CHEMS and/or SAHA in PC3 were quantified using qPCR to test a drug-gene combinatorial effect (FIG. 58). Significant increase in the expression level of GM-CSF was observed 3 days post transfection (~8,000 fold over the control, ctrl) with PMAXGFP-GM-CSF (GMCSF). The addition of DOPE/CHEMS (GMCSF+DOPE/CHEMS) or SAHA (GMCSF+5 µM SAHA) enhanced GMCSF expression by ~9000 and ~14,000 fold, respectively. Intriguingly, combination of DOPE/CHEMS and SAHA elicited a far superior effect on GM-CSF overexpression (~30,000 fold as compared to ctrl). These unanticipated results are suggestive of a distinct function of SAHA beyond merely stabilizing the tubulin network in enhancing GM-CSF expression. In addition to the increment with GM-CSF expression with TrafEn™, SAHA induced up-regulation of MICA and NKG2D up to 48 hours of treatment (FIG. 59). This observation is in line with the report on the effect of SAHA on multiple cell lines. Increased expression of MICA and NKG2D were responsible for the activation of NK cells. Together, these data suggest the TrafEn™ gene-drug combination as a promising strategy to generate cancer vaccine that activates both APC (GM-CSF) and NK cells (MICA).

Example 17

Synergistic Effect of OSKM Overexpression and VPA/Tubastatin A to Increase Reprogramming Efficiency of Human Fibroblast Reprogramming describes the process of cellular state conversions, including switch of differentiated cells into a less differentiated state. Genetic tools have been established to initiate reprogramming process in various cell types. For instance, the Yamanaka et al. successfully identified four transfection factors, Oct4, Sox2, Klf4, and cMyc, sufficiently generated iPSCs from fibroblast. There are several concerns in the clinical use of reprogrammed cell sources. The use of viral vectors may introduce risk of tumourigenesis and immunogenesis. Another concern is the risk of tumourigenesis induced by transgene integration. In particular, overexpression of c-Myc, a well-known oncogene, and its reactivation could cause tumour formation. Removal of c-Myc from the reprogramming cocktail greatly reduces the reprogramming efficiency. Interestingly, the functions of both cMyc and Klf4 can be compensated by treating cells with HDACi such as Valproic acid (VPA).

High N/P ratio of PEIMAX is required for transfection of human adult fibroblast (HaF) (FIG. 60). Increased N/P (from 50-70) did not result in further improvement of transfection suggest the presence of intracellular transfection barrier. Addition of TrafEn™ (PEIMAX-N/P=50, DOPE/CHEMS+ 1.0 µM Tubastatin A) resulted in drastic increment in the percentage of cells expressed GFP, ~70%. Conversely, transfection event was not detected with Lipofectamine and Satisfection mediated transfection (FIG. 61A). Using the TrafEn™ formulation to deliver the polycistronic expression vector (Addgene: 20328), expression levels of cMyc, KLF4, SOX2, OCT4 were found to be ~4000, ~4500, ~4800 and ~5400 fold higher as compared to the control (PMAXGFP). In the absence of TrafEn™, OSKM levels were ~1000 fold as compared to the control (FIG. 61B). The high level of expressions may contribute to the rapid formation of iPSC like colonies. Nine days after transfection, colonies were observed in cell culture transfected with TrafEn™ galenics (FIG. 61C). Meanwhile, the effect of VPA on the induction of the expressions of cMyc and KLF4 was explored (FIG. 62). Gradual increment of the expressions of both cMyc and KLF4 were observed up to 72 h. Taken together, these data suggest the TrafEn™ gene-drug combination as a promising strategy to induce efficient reprogramming process in human adult fibroblast using non-viral based method.

DISCUSSION

To our knowledge, this is the first report that demonstrated an unexpectedly high efficiency in transfecting differentiated neuronal cell-lines and primary cortical neurons using a non-viral carrier. The rational strategy involved mild centrifugation of aggregated polyplex, facilitating endosomal escape and enhancing microtubule trafficking. The choice of matched native and differentiated neuronal cell models and development of reliable quantitative tools greatly facilitated the identification and mitigation of the hitherto unrecognized transfection barriers in differentiated neurons using a non-viral carrier.

Differentiated neurons are sensitive to physical stress and alterations in cellular environment, making transfection of these cells a significant challenge. By limiting exposure of the cells to polyplex and by mild centrifugation, transfection efficiency and cell viability were significantly increased. Mild centrifugation is thought to deposit aggregated polyplex, which is formed in the high salt media (FIGS. 13 and 38-43). It is likely that polyplex is inherently unstable in the high salt media. The deposited polyplexes on the substrate was not released at significant levels into the media (FIG. 43), an observation incongruent to previous reports. Thus, deposited polyplex may be taken up directly from cell surface or the cell culture substrate, consistent with recent results showing the critical involvements of endocytic processes in neuronal migration, motility and adhesion to substrates. The critical role of deposited aggregated polyplex in mediating efficient transfection was discussed under the supplementary section (FIGS. 13 and 38-43).

Considerable efforts have been made to better understand the mechanisms of uptake and intracellular trafficking of non-viral carriers. Uptake of LPEI-polyplex has been shown to involve multiple pathways including caveolae and clathrin-mediated endocytosis. The precise size limits of clathrin- and caveolin-mediated endocytosis are currently unclear (120-500 nm). Recent evidences demonstrated the uptake of even larger LPEI-polyplex by a rottlerin-sensitive and unselective macropinocytotic pathway resulting in successful transfection of mammalian cells. Unexpectedly, the uptake of DNA in the native but not differentiated neuronal cells was sensitivity to PKC, indicative of alterations in the uptake pathway/s and intracellular trafficking of polyplex, which may have contributed to the differential localization of polyplex into acidic compartment.

In contrast to previous reports, the quantitative uptake of DNA is comparable between native and differentiated neuronal cells. Despite similar levels of uptake, differentiated neuronal cells were poorly transfected. This finding is consistent with previous reports, where attempts to increase transfection in differentiated neurons by enhancing uptake using polymers modified with RGD, HIV TAT, Tet-1, HGP have met with only modest improvements. Intriguingly, a differential localization of polyplex was observed between native and differentiated neuronal cells. Consistent with previous reports, polyplex was sequestered in acidic compartment in differentiated neurons. LPEI is thought to exert "proton sponge effect" but LPEI-polyplex was found to be entrapped within the acidic compartment on neuronal differentiation and the addition of DOPE/CHEMS released the labelled DNA from this compartment. The dramatic enhancement of endosomal escape of labelled pDNA and transfection efficiency by DOPE/CHEMS is unexpected and is consistent with the idea that endosomal escape of polyplex is critical. The pH-dependent destabilization of DOPE/CHEMS within the acidic endosomal environment is thought to result in membrane phase transition resulting in membrane fusion and eventually releasing the contents into the cytosol. It is worthy to note that other commercial endosome targeting reagents including chloroquine have no effect on transfection efficiency.

It has been shown that polyplex, similar to some viruses, utilizes the microtubule network to traffic through cytoplasm to the nucleus. Thus, stabilization of microtubule results in greater recruitment of dynein and kinesin motors, which enhances transfection. The capability to facilitate efficient endosomal escape using fusogenic lipids along with stabilization of the microtubule network serves as an attractive synergistic strategy for enhancing polymer-mediated transfection. Indeed, synergistic effect was observed when microtubule stabilization was induced. Evidently, with this rational approach, high transfection efficiency in differentiated neuronal cells and primary neurons has now been achieved. Intriguingly, the effect of fusogenic lipid and Tubastatin A enhanced transfection is synergistic and temporally controlled, suggesting that intracellular trafficking of polyplex is tightly controlled in differentiated neurons. Polyplex may be required to be released in the early stages of endocytosis and intracellularly trafficked to prevent degradation of DNA or transportation of polyplex to a non-productive pathway.

By rationally mitigating the contributions of the barriers using the combinatorial reagents and strategy described herein, it may not be surprising that other cationic polymers and derivatives may now be successfully used for neuronal transfection in vitro and in vivo, by exploiting colloidal stable polyplex that promote self-assembled supramolecular ensembles on cell membrane and directed targeting of selective intracellular trafficking pathways. In line with this suggestion, significant transfection enhancements have been observed with other cationic polymers (e.g., dendrimers and BPEI) and with non-neuronal cell types that are well known to be recalcitrant to cationic polymer based gene delivery (FIG. 30, FIG. 44 and FIG. 45). It is also worthy to note that the use of fusogenic reagent and HDAC inhibitor did not cause long-term effect on global cellular processes.

The elucidation of limiting barriers to transfection led to a rational approach of highly efficient gene delivery into differentiated neuronal cells in vitro. By re-routing the endosomal-released polyplex using pH sensitive lipids and enhancing microtubule mediated trafficking, high levels of transfection were achieved in differentiated neuronal cells and primary cortical neurons. These hitherto unrecognized changes in the trafficking of aggregated polyplex may provide a possible explanation for the differences in the transfection efficiencies of native and differentiated neurons. Thus, this study provides useful insights for the rational design of synthetic non-viral carriers and optimized galenics for gene transfection using cationic polymers into differentiated neuronal cells in vitro.

Fusogenic agents, for example 1,2-Dioleoyl-sn-glycero-3-phosphoethanolamine (DOPE)/cholesteryl hemisuccinate (CHEMS), improved gene delivery. Fusogenic agents facilitate endosomal escape through the pH-dependent destabilization of DOPE/CHEMS within the acidic endosomal environment, resulting in membrane phase transition and membrane fusion. As shown in further examples, DOPE/CHEM specifically re-directs carrier/DNA complexes away from the non-productive acidic compartment, thus leading to enhanced transfection efficiency. Fusogenic agents with properties similar to DOPE include Dipalmitoylphosphatidylcholine (DPPC) and 1,2-Dioleoyl-sn-glycero-3-Phosphatidylcholine (DOPC). Some peptides were found to have fusogenic property as well, such as haemagglutinin (HA2-peptide), influenza-derived fusogenic peptide diINF-7, T domain of Diphtheria toxin and polycationic peptides, such as polylysine and polyarginine.

Figure 3:
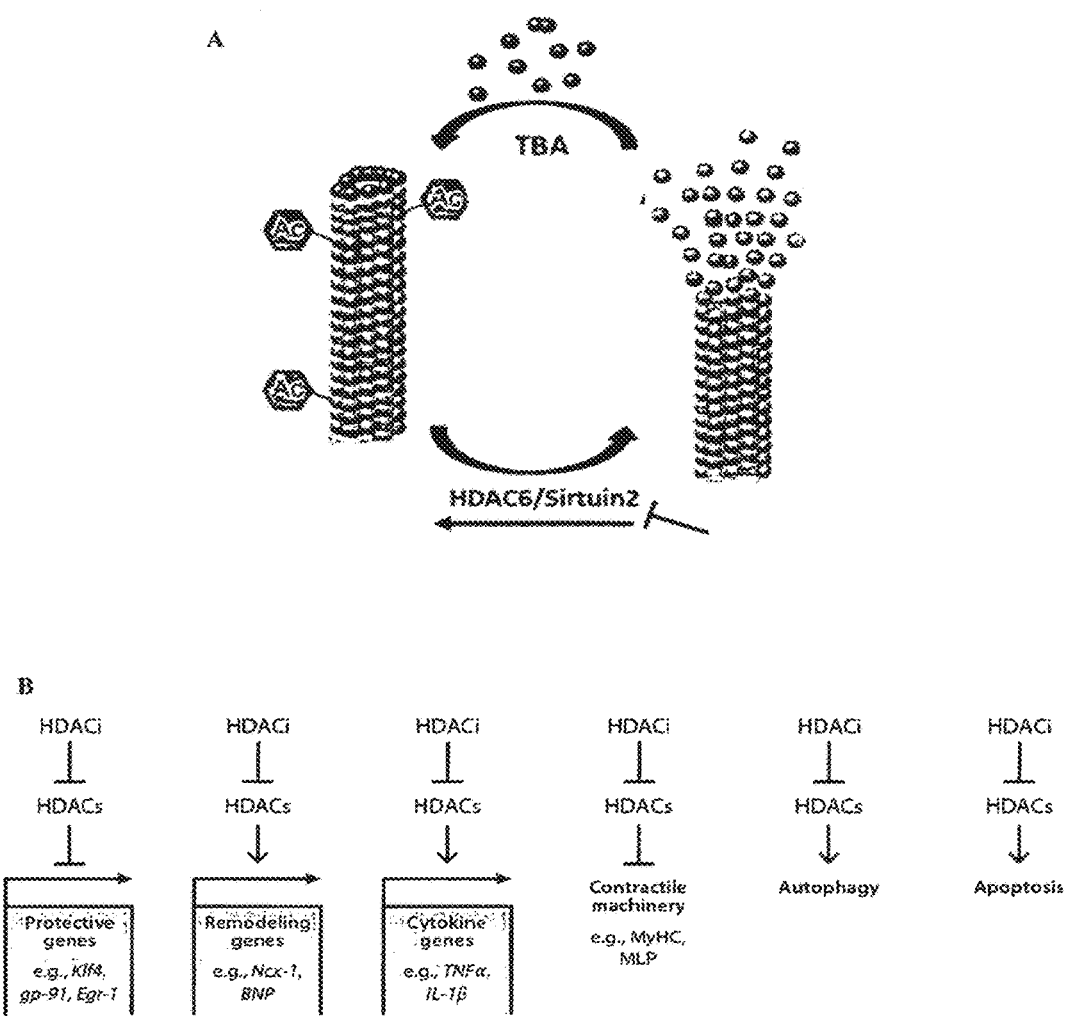
FIG. 3 shows the effects of a microtubular network modifier. (A) shows that microtubule dynamicity is inhibited by tubulin acetylation or tubulin binding agents (TBA).

The use of microtubule-targeting agent and epigenetic modifiers as first- and second line treatments in patients with various diseases is known in the art. The disclosure further encompasses the use of microtubule-targeting agents and epigenetic modifiers. Here, a microtubule-targeting chemosensitizer (Mt-C) is categorized as tubulin binding agents (TBA) and histone deacetylase inhibitors (HDACi) (FIG. 3).

The two major classes of tubulin binding agents are known in the art, taxanes and epothilones. TBA can suppress microtubule dynamics, leading to mitotic block and apoptosis. Taxanes may include paclitaxel (Taxol), docetaxel (Taxotere) or combinations thereof. Epothilones, like taxanes, are known in the art to prevent cell division by inducing cell cycle arrest at the G2-M transition phase, resulting in cytotoxicity and, in due course, cell death. Epothilone analogues known in the art are patupilone, ixabepilone, BMS 310705, sagopilone, KOS-862, and KOS-1584.

Table 1 below shows HDACi which have an inhibitory effect on HDAC/Sirtuin. HDACi, as known in the art, have been shown to have microtubule-targeting and/or epigenetic modification activities. HDACi inhibit HDAC6 and Sirtuin2 to promote acetylation of microtubules, resulting in the stabilization of the microtubule network. Acetylation has been repeatedly alleged to be associated with stability of microtubules, where the phrase 'acetylated microtubules' is often used synonymously with 'stable microtubules'. Similar to the effect of TBA, HDACi are known to arrest microtubule dynamics and exerts anti-cancer effect. Some HDACi, like vorinostat, inhibit multiple HDAC (HDAC1, 2, 3 and 6) and exhibit various activities, such as immunomodulation and apoptosis. HDACs are involved in the maintenance and function of chromatin via regulation of acetylation state of histone. Additionally, it is known that HDACi are known to have diverse functions, as the HDAC family influences a broad repertoire of physiological processes, including transcription of genes involved in proliferation, differentiation, survival and DNA repair. More recently, HDACi have been demonstrated to promote self-renewal of hematopoietic stem cells, enhance differentiation of neural stem cells and increase efficiency of reprogramming of somatic cells.

TABLE 1

HDACi with inhibitory effect on HDAC/Sirtuin. Developmental status of the inhibitors on various diseases was presented.

| HDAC inhibitor | Class | Type of disease | Developmental status | Targeted class of HDAC | Targeted HDAC/Sirtuin | IC50 (uM) |
|---|---|---|---|---|---|---|
| Apicidin | Peptide | NA | Tool compound | Class I | 1 | 0.02 |
|  |  |  |  |  | 2 | 0.02 |
|  |  |  |  |  | 3 | 0.02 |
| Belinostat (PXD101) | HA | Cutaneous T-cell lymphoma | Phase II clinical | Class I, IIb | 1 | 0.25 |
|  |  |  |  |  | 2 | 0.25 |
|  |  | Acute myeloid leukemia | Phase I/II |  | 3 | 0.2 |
|  |  |  |  |  | 6 | 0.41 |
| BML-210 | Benzamide | NA | tool compound | Class I | 1 | 14.99 |
|  |  |  |  |  | 2 | 10.91 |
|  |  |  |  |  | 3 | 2.62 |
| CHR-2845 | HA | Hematological disease | Phase I | Class I | NA | NA |
|  |  | Lymphoid malignancies | Phase I |  |  |  |
| Bufexamac | Non-steroidal | NA | Approved drug (Paraderm ®, Parfenac ®) | Class I, IIb | 3 | 341 |
|  |  |  |  |  | 6 | 10.7 |
|  |  |  |  |  | 8 | 235 |
|  |  |  |  |  | 10 | 12.3 |
| Dacinostat (NVP-LAQ824) | HA | NA | Phase I | Class I, IIb | 1 | 0.01 |
|  |  |  |  |  | 2 | 0.02 |
|  |  |  |  |  | 3 | 0.1 |
|  |  |  |  |  | 6 | 0.23 |
|  |  |  |  |  | 10 | 0.58 |
| Entinostat (MS-275; SNDX-275) | Benzamide | Refractory Hodgkin's lymphoma | Phase II | Class I | 1 | 6.23 |
|  |  |  |  |  | 2 | 8.31 |
|  |  | ER+ breast cancer | Phase II |  | 3 | 4.56 |
|  |  | immunosuppressive - infectious disease | Phase I |  | 8 | 201.36 |

TABLE 1-continued

HDACi with inhibitory effect on HDAC/Sirtuin. Developmental status of the inhibitors on various diseases was presented.

| HDAC inhibitor | Class | Type of disease | Developmental status | Targeted class of HDAC | Targeted HDAC/ Sirtuin | IC50 (uM) |
|---|---|---|---|---|---|---|
| JNJ-26481585 | HA | Acute myeloid leukemia | Phase I | Class I | NA | NA |
| | | Precursor cell lymphoblastic leukemia-lymphoma | Phase I | | | |
| | | BCR-ABL positive chronic myelogenous leukemia | Phase I | | | |
| MC-1293 | HA | NA | tool compound | Class I | 3 | 288 |
| Mocetinostat (MGCD-0103) | Benzamide | Follicular lymphoma | Phase II | Class I | 1 | 15.49 |
| | | | | | 2 | 17.59 |
| | | | | | 3 | 6.72 |
| Panobinostat (LBH-589) | HA | Classical Hodgkin's lymphoma | Phase III | Class I, IIb | 1 | 0.1 |
| | | Relapsed/Refractory Classical Hodgkin's lymphoma | Phase II | | 2 | 0.13 |
| | | Multiple myeloma | Phase I | | 3 | 0.27 |
| | | Primary myelofibrosis | Phase II | | 6 | 1.29 |
| | | Post-polycythemia vera myelofibrosis | Phase II | | 10 | 0.54 |
| | | Post-essential thrombocytopenia myelofibrosis | Phase II | | | |
| PCI-24781 | HA | Soft tissue sarcoma | Phase I/II clinical | Class I, IIb | 1 | 0.02 |
| | | | | | 2 | 0.03 |
| | | | | | 3 | 0.05 |
| | | | | | 6 | 0.05 |
| | | | | | 10 | 0.03 |
| PCI-34051 | HA | Anti-cancer | Pre-clinical | Class I | 8 | 2.3 |
| Romidepsin (FK228; FR901228) | Peptide | Cutaneous T-cell lymphoma | Phase II Approved drug(Istodax ®) | Class I | 1 | 0.08 |
| | | | | | 2 | 0.01 |
| | | | | | 3 | 0.02 |
| Resminostat | Hydroxamate | Hepatocellular carcinoma | Phase II | Class I, II | NA | NA |
| | | Hodgkin's lymphoma | Phase I | | | |
| SAHA (vorinostat) | NA | cutaneous T-cell lymphoma | Phase I | Class I, IIb | 1 | 0.29 |
| | | Refractory large B-cell lymphoma | Phase II | | | |
| | | Stage IIIA non-small cell lung cancer, | Phase I/II | | | |
| | | Stage IIIB non-small cell lung cancer | Phase I/II | | | |
| | | Multiple myeloma | Phase III | | 2 | 0.37 |
| | | Acute/chronic myeloid leukemia | Phase I | | | |
| | | Acute promyelocytic leukemia | Phase I | | | |
| | | Myelodysplastic syndromes | Phase I | | | |
| | | Relapsed/Refractory multiple myeloma | Phase I | | 3 | 0.39 |
| | | Acute myeloid leukemia | Phase II | | | |
| | | Brain and central nervous system tumor | Phase I | | | |
| | | Lymphoma | Phase I | | | |
| | | Unspecified childhood solid tumor | Phase I | | 6 | 0.21 |
| | | Sarcoma | Phase II | | | |
| | | Relapsed/Refractory multiple myeloma | Phase II | | | |
| | | Carcinoma, non-small cell lung cancer | Phase II | | | |
| Scriptaid | HA | NA | tool compound | Class I. II | 1 | 1.37 |
| | | | | | 2 | 1.51 |
| | | | | | 3 | 4.24 |
| | | | | | 6 | 0.25 |
| Tacedinaline | Benzamide | Multiple Myeloma and Plasma Cell Neoplasm | Phase II | Class I | 1 | 13.08 |
| | | | | | 2 | 12.84 |
| | | | | | 3 | 5.39 |
| Trichostatin A | HA | Systemic lupus erythematous | Phase I | Class I, IIb | 1 | 0.006 |
| | | | | | 2 | 0.007 |
| | | Rheumatoid arthritis | Phase I | | 3 | 0.02 |
| | | | | | 6 | 0.06 |

TABLE 1-continued

HDACi with inhibitory effect on HDAC/Sirtuin. Developmental status of the inhibitors on various diseases was presented.

| HDAC inhibitor | Class | Type of disease | Developmental status | Targeted class of HDAC | Targeted HDAC/Sirtuin | IC50 (uM) |
|---|---|---|---|---|---|---|
| Valproic Acid | Fatty acid | Neuroectodermal tumor<br>Brain metastases<br>Advanced cancer | Phase I<br>Approved drug(Depakote ®,<br>Depakene ®,<br>Depacon ®,<br>Stavzor ®) | Class I, IIb | 1<br>2<br>3<br>6 | 442.18<br>485<br>4177<br>11784 |
| B2 | NA | Neurodegenerative disease | Pre-clinical | Class III | SIRT2 | 35 |
| Salermide | Amide | Anti-cancer | Pre-clinical | Class III | SIRT1<br>SIRT2 | NA |
| Sirtinol | Amide | Anti-cancer | Pre-clinical | Class III | SIRT2 | 40 |

Grey code represents possible microtubule stabilization effect of inhibitor and its application in TrafEn ™-Gene combination strategy.
HA: hydroxamic acid.

HDAC6 inhibition is known to affect microtubule dynamics in non-neuronal cells and neurite outgrowth in neuronal cells. Thus, the possibility of long-term effect of Tubastatin A on cellular processes of neuronal cells including microtubule dynamics, neurogenesis and global cellular metabolism deserve careful elucidation. Evidently, treatment with Tubastatin A results in transient effect (<24 h) on tubulin acetylation (FIG. 35). Moreover, the transfection paradigm described herein did not result in sustained alteration on neurite outgrowth (FIG. 36) and global metabolism (FIG. 37) of the neuronal cells.

MSC are a heterogeneous subset of adult stromal stem cells that can be isolated and expanded ex vivo, and can appropriately differentiate into cells of the residing tissues, repair the damaged tissues and restore normal functions. Other than their differentiation potential to osteogenic, chondrogenic, and adipogenic cell types, studies have demonstrated the capability of MSC to generate neurons, kidney and other cell types too. Viral mediated delivery of BMP2 expression vector have been developed to drive such stem cells into osteogenic cells by providing genetic signals to improve the outcome of differentiation protocol. In addition to the use of MSC as a cell source to generate differentiating cells, it has been tested to act as gene/drug delivery vehicles. MSCs were genetically modified with BMP2 to facilitate tissue repair. On the other hand, an emerging approach to enhance differentiation of MSC is the direct treatment with HDACi. It has been suggested in numerous reports that HDACi such as TSA, SAHA and valproic acid can promote osteogenic differentiation of MSC. These HDACi induced epigenetic alterations resulting in the up-regulations of osteogenic promoting factors such as BMP2, RUNX, osterix, and osteopontin. To date, the synergistic effect of BMP2 transfection and TSA has yet to be tested.

Methods

Cell Culture

Neuro2A (ATCC: CCL-131TM) stably expressed GFRα2a cells and rat primary cortical neurons' were cultured and maintained as described previously (Yoong, L. F., G. Wan, and H. P. Too. Mol Cell Neurosci, 2009. 41(4): p. 464-73; Zhou, L. and H. P. Too. PLoS One, 2011. 6(6): p. e21680). Non-neuronal cells comprise <0.5% of the cell population of neurons grow in Neurobasal-B27 (Brewer, G. J., et al. J Neurosci Res, 1993. 35(5): p. 567-76). On DIV 3 (3 days in vitro), primary neurons were transfected. For transfection of differentiated neuronal cells, Neuro2A and NG-108 cells were differentiated with 50 ng/ml glial cell-line derived neurotrophic factor (GDNF; Biosource, Camarillo, Calif.), 10 µM all trans retinoic acid (RA) or 10 µM Forskolin (FSK; Sigma, St. Louis, Mo.) in Dulbecco's Modified Eagle Media (DMEM) supplemented with 1% Fetal Bovine Serum (FBS) for 48 h prior transfection.

Generation of TrafEn™

Firstly, the lipid components (e.g. DOPE and CHEMS) were dissolved in chloroform. These components were mixed at a certain ratio (DOPE:CHEMS), depending on the intended applications and type of lipid used to form the fusogenic liposome. The solvent was then evaporated, thus facilitating the formation of a lipid film comprising DOPE/CHEMS at the bottom of glass tube. The lipid film was reconstituted in 25 mM HEPES buffer by vigorous shaking, after which the lipid solution was sonicated for 2 min in a bath-type sonicator. This lipid solution construes the first agent. The TrafEn™ composition is then prepared by combining the first agent and a second agent, as defined in the disclosure. The TrafEn™ composition referenced also envisions the usage of fusogenic peptides instead of fusogenic liposomes.

Transfection Procedure

Plasmid DNA expressing EGFP was purified according to manufacturer's instruction (Geneaid Biotech, Taiwan). LPEI (25-kDa; Polyscience, USA) was added to pDNA in 25 mM HEPES buffer at different N/P ratios and incubated at room temperature for 15 min. LPEI/pDNA complex was then added to complete media (1:10) to prepare the transfection mixture (pDNA at 2 µg/ml). For bulk transfection (with or without centrifugation), cells were seeded 24 h prior to transfection. The transfection mixture was added to cells in culture and centrifuged at 280 g for 5 min. The transfection mixture was then replaced with complete media and the cells were further incubated. For transfection of differentiated cells, transfection mixture was replaced with DMEM (1% FBS) containing corresponding differentiation reagent. Transfection efficiency (percentage of EGFP positive cells) was quantified, either through manual counting or fluorescence-activated cell sorting (FACS) analysis after incubation for indicated periods.

For studies using inhibitors, cells were incubated with Dynasore (30 µg/ml), Filipin III (5 µg/ml) or Rottlerin (2.5 µg/ml) in DMEM (0.5% FBS) for 45 min prior transfection. Cells were further incubated in DMEM (0.5% FBS) containing corresponding inhibitors post transfection. At the concentrations used, there was no evidence of cell death.

To improve transfection in differentiated neurons, DOPE/CHEMS and Tubastatin A (Bio Vision, San Francisco, USA) were used. Lipid film comprising DOPE/CHEMS (9:2 molar ratio) (Polar Avanti Lipid, Alabaster), was formed at the bottom of glass tube after evaporation of the solvent, chloroform. The lipid film was reconstituted in 25 mM HEPES buffer and sonicated for 2 min in a bath-type sonicator (Brandson 2200). The lipid solution was added to the cell culture at various indicated time post transfection. One hour post transfection, Tubastatin A (5 or 16 µM) was added to the culture media. The inhibitor containing media were replaced by fresh media 24 h later.

Flow Cytometry Analysis

After transfection, the cells were trypsinized, centrifuged and re-suspended in PBS. Cell clumps were removed by filtering through a 40 µm mesh. The percentage of cells expressing EGFP was quantified by FACS analysis (BD FACSCanto, BD Biosciences) and the raw data analyzed using WinMDI (V2.9). At least 10,000 cells were analysed per sample.

Real-time qPCR for Quantification of DNA

To quantify DNA internalized by the cells, the supernatant was removed and the cells were washed once with 1×PBS and incubated in DMEM containing pAA/DNAse for 2 h at 4° C. Next, the cells were trypsinized and treated with pAA/urea lysis buffer. Efficiency of DNA release by pAA/urea lysis buffer and pAA/DNase was evaluated (Supplementary FIGS. 15 & 18). Quantification of DNA after incubation of Trypsin with deposited polyplex alone revealed insignificant amount of pDNA detected in the trypsin fraction (data not shown). Primers specific for EGFP, forward primer (5'-3', GACCACTACCAGCAGAACACC; SEQ ID NO:1) and reverse primer (5'-3', GACCATGT-GATCGCGCTT; SEQ ID NO:2) were used. PCR quantification of the pDNA was performed as previously described (Yoong, L.F., G. Wan, and H.P. Too. Mol Cell Neurosci, 2009. 41(4): p. 464-73). The absolute amount of pDNA was determined using plasmid standards by interpolation.

Imaging Studies

FITC- and Rhodamine-pDNA were prepared according to manufacturer recommendation (Minis Bio, USA). Expression of EGFP was observed in cells transfected with fluorescently labeled pDNA (data not shown). FITC- or Rhodamine-pDNA was used for visualization of internalized polyplex and extracellular fluorescence of the labeled pDNA was quenched with EtBr (20 µg/ml) or 0.4% trypan blue respectively 4 h post transfection. Cell images were taken before and after quenching with an inverted Zeiss microscope equipped with fluorescence detection (Zeiss cell observer Z1) and processed (Axio Vision Rel. 4.7). Quenching efficiency of trypan blue was examined (Supplementary FIG. 7). To study co-localization of Rhodamine-pDNA and the acidic compartment, cells were incubated with lysotracker green DND-26 (50 nM) for 5 min Image was captured with a Zeiss confocal microscopy (LSM710, Oberkochen, Germany). Co-localized pixel was analysed with Zeiss ZEN software (v2010).

Cell Viability Assay

To access the influence of LPEI mediated transfection on cellular viability of native and differentiated neuronal cells, Neuro2A and NG-108 cells were differentiated with GDNF (50 ng/ml) or RA (10 µM) and Fsk (10 µM) in the 96-well plates 48 h prior transfection. Cells were then exposed to LPEI/pDNA (at various N/P ratios) for 15 min or 4 h. With or without centrifugation at 280 g for 5 min, transfection mixtures were replaced with complete medium and incubated for 48 h. Culture medium was replaced with 100 µl DMEM and 20 µl of CellTiter 96 Aqueous One Solution Cell Proliferation Assay (Promega, Singapore). Following 1 h incubation at 37°, the absorbance at 490 nm was recorded using a 96-well Microplate reader (Model 680, Biorad).

DNA Release Assay

The DNA was collected through the following procedures: (1) to quantify DNA in supernatant, the supernatant was treated with pAA/urea lysis buffer to release DNA; (2) to quantify DNA associated with cells, the supernatant was removed and the cells were washed once with 1×PBS before being harvested by trypsinization and treated with pAA/urea lysis buffer; (3) to quantify DNA internalized by the cells, the supernatant was removed and the cells were washed once with 1×PBS and incubated in DMEM containing pAA/DNAse for 2 h at 4° C. Next, the cells were trypsinized and treated at 95° C. for 30 min with pAA/urea lysis buffer-polyacrylic acid (pAA, Sigma, Mw: 8000; 10 ng of pAA/ng of pDNA; 32 carboxyl groups in pAA/1 phosphate group in pDNA), 0.5 M sodium chloride, 10 mM sodium phosphate and 4 M urea. pAA was used as a competitive reagent for displacement of pDNA from LPEI. The efficiency of pDNA dissociation was visualized/quantified using two different approaches—DNA retardation assay and qPCR. DNA complexes were electrophoresed (100 V, 20 min) in 0.8% agarose gel, stained with ethidium bromide and visualized on a UV transilluminator.

Removal of Surface Bound pDNA

After transfection, cells (in 6-well plate) were incubated with 400 µl serum free DMEM containing pAA (10 ng pAA/ng pDNA), 10 mM $CaCl_2$, 6 mM $MgCl_2$ and 4 unit/ml deoxyribonuclease I (DNAse) for 2 h at 4° C. This formulation was optimized for complete release and degradation of surface bound pDNA. Plasmid DNA complexed with LPEI was displaced by pAA and degraded by DNAse I in the presence of $CaCl_2$ and $MgCl_2$. Incubation at 4° C. prevented internalization of DNAse by the cells. RT-qPCR and imaging studies confirmed the efficient removal of surface bound pDNA using this approach (Supplementary FIG. 18).

Dynamic Light Scattering

LPEI/pDNA (N/P=20) were prepared in 25 mM HEPES or DMEM. Particle size was measured by dynamic light scattering using Zetasizer Nano (Malvern, Worcestershire, United States).

Deposit Mediated Transfection

For deposit-mediated transfection, the transfection mixture was transferred to the culture plate (pre-coated with complete media for 24 h) and incubated for the indicated periods (with or without centrifugation). The transfection mixture was removed and cells were seeded. Transfection efficiency (percentage of EGFP positive cells) was quantified, either through manual counting or through FACS analysis 48 h post transfection.

Immunocytochemistry

Control and 10 µM differentiated Neuro2a Cells were fixed with 4% formaldehyde in 1×PBS for 20 min at room temperature and subsequently permeabilized in 0.5% Triton-X100 in 1×PBS. Then, the samples fixed cells were blocked with normal goat serum (1:10; Dako, Glostrup, Denmark) in 0.1% Triton X-100/1×PBS for 30 min at 37° C. The cells were then incubated with primary antibodies against acetylated α-Tubulin (Sigma Aldrich T7451, 1:200 dilution) or TuJ (R&D Systems MAB1195, 1:50 dilution) in 0.1% TritonX-100/1% BSA/1×PBS at 37° C. for 2 h and washed three times in 1×PBS. Subsequently, the cells were incubated with goat anti-mouse fluorescent secondary antibody (AlexaFluor 488/596; Invitrogen, CA) diluted 1:200 in 0.1% Triton X-100/1% BSA/1×PBS for 2 h at 37° C. The cells were washed three times in 1×PBS and mounted. Image acquisition was performed using the Zeiss LSM710 with Axio Observer.Z1 confocal microscope system (Oberkochen, Germany). All images were taken with identical laser and optical settings.

Metabolites Assay by LC-MS

Cells (cultured in 6-well plate, ~1 million cells) were rapidly rinsed by 2 mL of ice cold HPLC water. Then, the metabolic states of the cells were quenched by subjecting the culture plate to liquid nitrogen after aspiration of the HPLC water. After 1 min incubation, 250 µL of ice cold methanol:chloroform (9:1 ratio) was added to each well for extraction purpose and cells were scraped with a cell scraper (Greenpia Tech.) (Lorenz, M. A., C. F. Burant, and R. T. Kennedy. Anal Chem, 2011. 83(9): p. 3406-14). Extracts were transferred to 1.5 mL micro-centrifuge tubes containing 0.1 mm glass beads (Biospec Product). To release the metabolites efficiently, the samples were subjected to Mini-Beadbeater (Bio Spec Products Inc.) for 2 min. After which, the extracts were pelleted by centrifugation for 3 min at 16 000 g. The supernatants were transferred to autosampler vials (Agilent tech.) and assayed.

The UPLC (Waters ACQUITY UPLC)—(TOF) MS (Bruker micrOTOF II) platform was used to analyse the metabolites. To scan 50-800 m/z in negative mode with −500 V end plate voltage and 4500 V capillary voltage, electrospray ionization was used and (TOF) mass spectrometry was operated. One bar of nebulizer gas was provided. The drying gas rate and dry gas temperature was adjusted at 9 mL/min and 200° C. respectively. From the acquired data (50-800 m/z), a range of m/z (0.06 m/z width, the average m/z distribution width with the MS instrument in use) was extracted). Subsequently, the retention time was determined for each intermediate and the peak area was integrated for each metabolite using manufacturer's software.

Relative amount of each metabolite to ATP was calculated. ATP was used as normalizer as it was the most abundant metabolite and stable across samples at each time point with coefficient variation less than 5%. After normalization, relative fold change of metabolite to the negative control at each time point was calculated.

The invention claimed is:

1. An in vitro method for enhancing intracellular trafficking of genetic material in a cell, the method comprising:
   a) transfecting the cell with the genetic material,
   b) adding to the cell a first agent simultaneously, separately or sequentially with a second agent within 1, 2, 3, 4, or 5 hours of transfecting the cell with the genetic material under a),
   wherein the first agent directs the genetic material transfected under a) away from the acidic compartments in the cell, and wherein the second agent stabilizes the microtubule or a network thereof, wherein the first agent comprises a lipid fusogenic agent or a peptide fusogenic agent, wherein the second agent is selected from a group consisting of a histone deacetylase inhibitor (HDACi), a tubulin binding agent (TBA), a siRNA that directly or indirectly affects the microtubule network stability, and combinations thereof, and wherein the genetic material is a nucleic acid.

2. The method according to claim 1, wherein the lipid fusogenic agent is selected from the group consisting of DOPE, CHEMS, DPPC and DOPC and combinations thereof.

3. The method according to claim 1, wherein the peptide fusogenic agent is selected from the group consisting of haemagglutinin (HA2-peptide), influenza-derived fusogenic peptide diINF-7, T domain of Diphtheria toxin, polycationic peptides, polylysine, polyarginine, and combinations thereof; or
   wherein the peptide fusogenic agent is modified by an attachment of a compound selected from the group comprising of biomolecules, lipids, nucleic acids and synthetic carriers.

4. The method according to claim 1, wherein the HDACi is selected from the group consisting of Tubastatin A, belinostat, bufexamac, panobinostat, PCI-24781, SAHA (vorinostat), scriptaid, trichostatin A, valproic acid, salermide, sirtinol, and combinations thereof.

5. The method according to claim 1, wherein the TBA is selected from the group consisting of taxanes, epothilones, and a combination thereof.

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 1
gaccactacc agcagaacac c                                          21

<210> SEQ ID NO 2
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 2
gaccatgtga tcgcgctt                                              18

6. The method according to claim 5, wherein the taxanes are selected from the group consisting of paclitaxel, docetaxel, and a combination thereof; and wherein the epothilones are selected from the group consisting of patupilone, ixabepilone, BMS 310705, sagopilone, KOS-862, KOS-1584, and combinations thereof.

7. The method according to claim 1, wherein the genetic material is coupled to at least one cationic species.

8. The method according to claim 7, wherein the cationic species is selected from the group consisting of polyethylene imine, polycationic amphiphiles, DEAE-dextran, cationic polymers, their derivatives, and combinations thereof.

9. The method according to claim 8, wherein the cationic species is cationic polymers selected from the group consisting of dendimers, branched-polyethylenimine (BPEI), linear-polyethylenimine (LPEI), Poly(amidoamine)(PA-MAM), XTREMEGENE XPHP®, and combinations thereof.

10. The method according to claim 7, wherein the nucleic acid:
polymer (N/P) ratio of genetic material to cationic species is selected from the group consisting of about 0 to about 1000, about 0 to about 500, about 0 to about 100, about 0 to about 50 and about 0 to about 20; and wherein the N/P ratio is the ratio of the genetic material to the cationic species forming polyplexes within the composition.

11. The method according to claim 1, wherein the nucleic acid is selected from the group consisting of DNA, RNA, mRNA, ribozymes, antisense oligonucleotides, modified polynucleotides and combinations thereof.

12. The method according to claim 1, wherein the cell is an undifferentiated cell.

13. The method according to claim 1, wherein the cell is selected from the group consisting of a nervous system cell, a liver cell, a hematopoiesis cell, a peripheral blood cell, an umbilical blood cell, a bone marrow cell, a tumour cell, an ischemic tissue cell, a skin cell, a stem cell, and a cancer cell line.

14. The method according to claim 13, wherein the cancer cell line is selected from the group consisting of U87MG (ATCC no. HTB-14), U251MG (CLS ID) no. 300385), MCF7 (ATCC no. HTB-22), MDA-MB-231 (ATCC no. HTB-26), MCF10a (ATCC no. CLR-10317), RAW 264.7 (ATCC no. TIB-71), PC3 (ATCC no. CRL-1435), M14 (Pubmed ID: 12354931), MEF (ATCC no. SCRC-1040), Neuro2A (ATCC no. CCL-131), NG-108 (ATCC no. HB-12317) and HeLa (ATCC no. CCL-2).

15. The method according to claim 1, wherein the second agent is to be provided after the first agent.

16. The method according to claim 1, wherein the second agent further comprises a therapeutic agent.

17. The method according to claim 16, wherein the therapeutic agent is a chemotherapeutic agent selected from the group consisting of paclitaxel, docetaxel and epothilones, and combinations thereof.

18. The method according to claim 1, wherein the cell is a differentiated cell.

* * * * *